US005661006A

United States Patent [19]

Brown et al.

[11] Patent Number: 5,661,006
[45] Date of Patent: Aug. 26, 1997

[54] DNA ENCODING THE CANINE CORONAVIRUS SPIKE PROTEIN

[75] Inventors: Thomas David Kay Brown, Needingworth; Brian Colin Horsburgh, Cambridge, both of England

[73] Assignee: Akzo Nobel N.V., Arnhem, Netherlands

[21] Appl. No.: 308,872

[22] Filed: Sep. 19, 1994

Related U.S. Application Data

[63] Continuation of Ser. No. 42,846, Apr. 5, 1993, abandoned, which is a continuation of Ser. No. 872,641, Apr. 24, 1992, abandoned.

[30] Foreign Application Priority Data

Apr. 25, 1991 [EP] European Pat. Off. ............ 91 303 737

[51] Int. Cl.$^6$ .......................... C12P 21/02; C07H 21/00; C12N 15/50; C12N 15/63; C12N 15/06

[52] U.S. Cl. ............................... 435/69.3; 935/9; 935/10; 935/11; 935/12; 435/320.1; 435/252.3; 536/23.72

[58] Field of Search ....................... 935/9–12; 424/221.1; 435/69.3, 320.1, 252.3; 536/23.72

[56] References Cited

U.S. PATENT DOCUMENTS

| | | |
|---|---|---|
| 4,470,967 | 9/1984 | Gough et al. . |
| 4,554,101 | 11/1985 | Hopp . |
| 4,722,848 | 2/1988 | Paoletti et al. . |
| 4,904,468 | 2/1990 | Gill et al. . |
| 5,202,430 | 4/1993 | Briar et al. . |

FOREIGN PATENT DOCUMENTS

| | | |
|---|---|---|
| 0138242 | 4/1985 | European Pat. Off. . |
| 0278541 | 8/1988 | European Pat. Off. . |
| 0295057 | 12/1988 | European Pat. Off. . |
| 0344872 | 12/1989 | European Pat. Off. . |
| 0376744 | 7/1990 | European Pat. Off. . |
| WO9111525 | 8/1991 | WIPO . |

OTHER PUBLICATIONS

Sambrook et al. Molecular Cloning, a Laboratory Manual. 2nd edition 1989 see pp. 1.1–1.20 and 17.1–17.16 and 17.37–17.41.

Bowie et al. Science 247:1306–1310.

Talbot et al. J. Virol. 62(8):3032–36 Aug. 1988.

Rasschaert et al. J. Gen. Virol. 68:1883–1890 1987.

Jaye et al. Nucleic Acids Research 11(8):2325–2335 1983.

Wood et al. PNAS 82:1585–88 Mar. 1985.

Lathe, R. J. Mol. Biol. 183:1–12 1985.

Horzinek et al. Infection and Immunity 37:1148–55 1982.

Young and Davis PNAS 80:1194–98 Mar. 1983.

R.J. DeGroot et al. J. Gen. Virol. 68:2639–2646 1987.

Jacobs et al. Virus Research 8:363–371 1987.

Lenstra et al. Molecular Immunology 26(1):7–15 1989.

Luckow et al. Biotechnology 6:47–55 1988.

Binns et al. J. Gen. Virol. 66:719–26 1985.

Harlow, Ed et al. (Editors), "Antobodies, A Laboratory Manual", published by Cold Spring Harbor Laboratory, see p. 61 1988.

Bae, T. et al., "Differentiation of Transmissible Gastroenteritis Virus from Porcine Respiratory Coronavirus and Other Antigenically Related Coronaviruses by Using cDNA Probes Specific for the 5' Region of the S Glycoprotein Gene", *Journal of Clinical Microbiology*, vol. 29, No. 1, Jan., 1991, pp. 215–218.

Hohdatsu et al., "Characterization of Monoclonal Antibodies against Feline Infectious Peritonitis Virus Type II and Antigenic Relationship Between Feline, Porcine, and Canine Coronaviruses", *Archives of Virology*, vol. 117, Nos. 1, 2 and 13, Mar. 1991, pp. 85–95.

*Primary Examiner*—Anthony C. Caputa
*Attorney, Agent, or Firm*—Mary E. Gormley; William M. Blackstone

[57] ABSTRACT

The invention is related to a nucleic acid sequence &coding a Canine coronavirus (CCV) spike protein. Such a protein can be used for the immunization of dogs against CCV infection. The nucleic acid sequence encoding the CCV spike protein can be applied for the preparation of the spike protein by means of genetic engineering techniques or can be applied for the preparation of vector vaccines.

9 Claims, 4 Drawing Sheets

DNA ENCODING THE CANINE CORONAVIRUS SPIKE PROTEIN

This is a continuation of U.S. application Ser. No. 08/042,846, filed Apr. 5, 1993, now abandoned, which is a continuation of U.S. application Ser. No. 07/872,641, filed Apr. 24, 1992, now abandoned.

FIELD OF THE INVENTION

The present invention is concerned with a nucleic acid sequence encoding a CCV spike protein, a recombinant vector or recombinant vector virus comprising such a nucleic acid sequence, a host cell transformed with such a recombinant vector or infected with the recombinant vector virus, as well as a vaccine against CCV infection in dogs.

BACKGROUND OF THE INVENTION

Canine coronavirus (CCV) is a member of the distinct viral family of Coronavirus. Viruses belonging to this genus are known to infect a variety of animal species including man. They cause diverse diseases, such as gastro-enteritis (in swine, turkeys, mice, calves, dogs, cats and man), salivary gland infection (in rodents), respiratory disease(in man, swine, avians and dogs) and encephalitis (in young swine).

CCV was first isolated from military dogs in Germany in 1971 and has found to be highly contagious and it spreads rapidly among susceptible dogs. Usually, the CCV is ingested on materials contaminated by infectious feces. Oral infection leads to viral replication in epithelial cells of the small intestine and CCV has also been found in the intestinal lymph nodes.

The signs of the disease can develop 1–3 days following infection and include vomiting, diarrhoea, anorexia, depression and dehydration. The persistence and severity of signs is often related to stress and the presence of other viruses, parasites or bacteria. Whereas the enteric symptoms are dominant, respiratory signs including nasal and ocular discharge have also been reported.

Dogs are the only known host of the CCV. Although CCV inoculation of cats and pigs results in infection, no clinical disease will be caused by CCV in these species. There is no evidence that humans, cattle and mice are susceptible to CCV.

Cross protection studies have shown that the Coronaviruses induce little or no immunity to each other. For example, experimental infection of dogs with transmissible gastro-enteritis virus (TGEV) of pigs or feline infectious peritonitis virus (FIPV) of cat does not protect them against the effects of a subsequent CCV infection.

Coronaviruses consist of a group of enveloped viruses containing a genome consisting of a single-stranded RNA of about 30 kb. This genome encodes inter alia three important structural proteins: a spike protein (S), a membrane protein (M) and a nucleocapsid protein (N). The glycosylated spike protein $S_o$ is cleaved to form $S_1$ and $S_2$ in some coronaviruses. Two or three copies of each of $S_1$ and $S_2$ form a characteristic CCV surface structure, the spike or peplomer. The spike protein and its constituent polypeptides thereof play an important role in inducing a virus neutralizing immune response in infected animals.

SUMMARY OF THE INVENTION

Conventional CCV vaccines comprise chemically inactivated virus vaccines or modified live-virus vaccines. However, inactivated vaccines require additional immunizations, disadvantageously contain adjuvants and are expensive to produce. Further, some infectious virus particles may survive the inactivation process and may cause disease after administration to the animal.

In general, attenuated live virus vaccines are preferred because they evoke an immune response often based on both humoral and cellular reactions. Up to now, such vaccines based on CCV strains can only be prepared by serial passage of virulent strains in tissue culture. However, because of this treatment uncontrolled mutations are introduced into the viral genome, resulting in a population of virus particles heterogeneous in their virulence and immunizing properties. In addition it is well known that such traditional attenuated live virus vaccines can revert to virulence resulting in disease of the inoculated animals and the possible spread of the pathogen to other animals.

Improved vaccines might be constructed, based on recombinant DNA technology, which only contain the necessary and relevant CCV immunogenic material capable of eliciting an immune response against the CCV pathogens, or which contain the genetic information encoding said material, and do not display above-mentioned disadvantages of the live or inactivated vaccines.

According to the present invention, an isolated and purified nucleic acid sequence encoding a polypeptide having one or more immunogenic determinants of a CCV spike protein is provided which can be applied for the preparation of a vaccine for the immunization of dogs against CCV infection.

"Nucleic acid sequence" as used herein refers to a polymeric form of nucleotides of any length, both to ribonucleic acid sequences and to deoxy ribonucleic acid sequences. In principle, this term refers to the primary structure of the molecule. Thus, this term includes double and single stranded DNA, as well as double and single stranded RNA, and modifications thereof.

In general, the term "polypeptide" refers to a molecular chain of amino acids with a biological activity, does not refer to a specific length of the product and if required can be modified in vivo or in vitro, for example by glycosylation, amidation, carboxylation or phosphorylation; thus inter alia, peptides, oligopeptides and proteins are included.

The term "polypeptide having one or more immuno-genic determinants of a CCV spike protein" refers to a polypeptide having one or more epitopes capable of eliciting a protective immune response in a dog against CCV infection or disease.

DETAILED DESCRIPTION OF THE INVENTION

Figure 1:
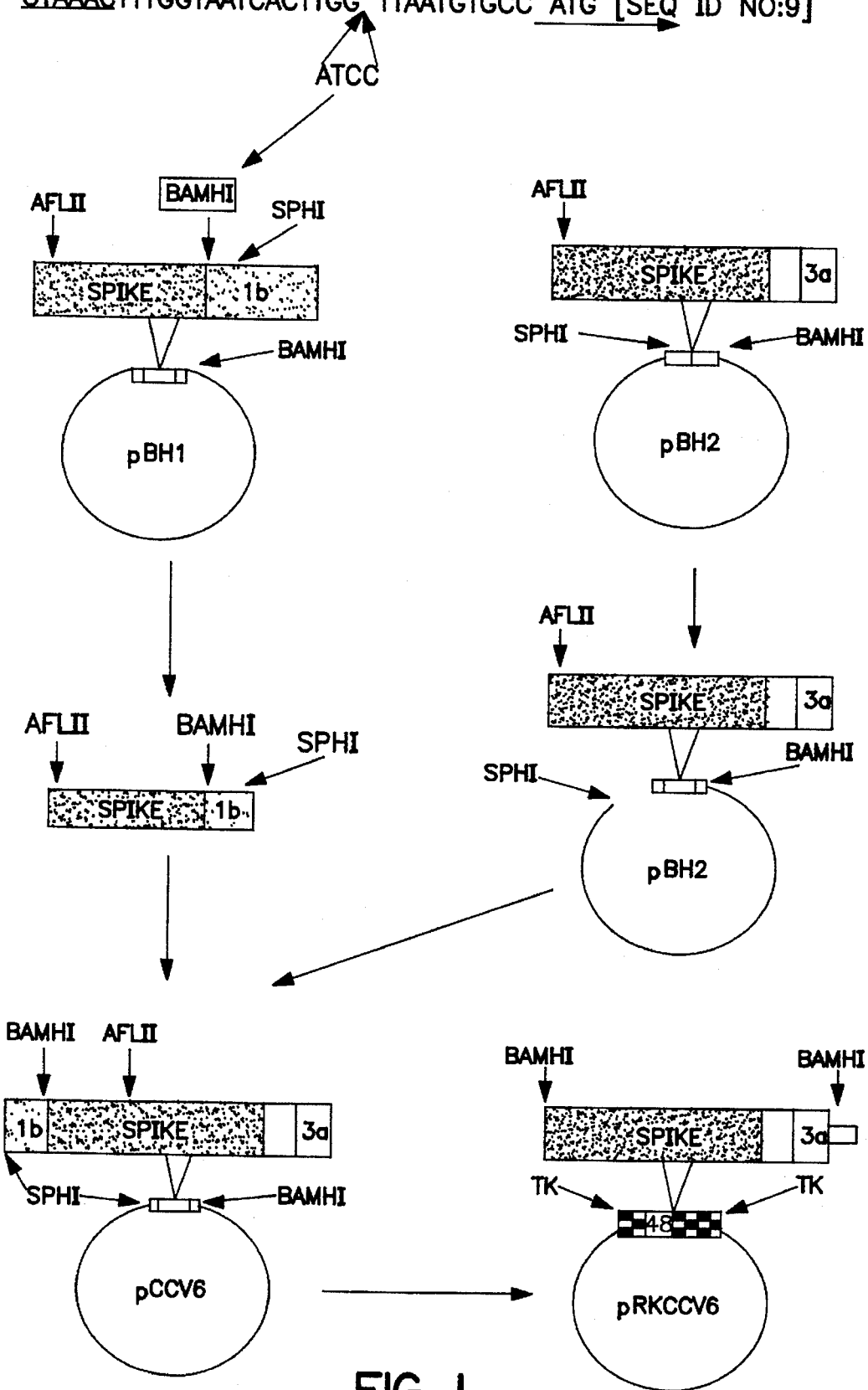
FIG. 1 shows the cloning strategy for the construction of the plasmid pRKCCV6 from plasmids pBH1 and pBH2.

In particular, the present invention provides a nucleic acid sequence encoding a polypeptide having one or more .immunogenic determinants of the CCV spike protein which has an amino acid sequence shown in SEQ ID NO: 2, 4 or 6.

Also included within the scope of the present invention are nucleic acid sequences encoding a functional variant of the polypeptide shown in SEQ ID NO: 2, 4 or 6. These functional variants are polypeptides having an amino acid sequence derived from the amino acid sequence specifically disclosed in SEQ ID NO: 2, 4 or 6 but retain one or more immunogenic determinants of a CCV spike protein, i.e. said variants having one or more epitopes capable of eliciting a protective immune response in a dog against CCV infection or disease.

It will be understood that for the particular polypeptide embraced herein, derived from the CCV-6, Insavc-1 or Liverpool C54 strain, natural variations can exist between individual viruses or strains of canine coronaviruses. These variations may be demonstrated by (an) amino acid difference(s) in the overall sequence or by deletions, substitutions, insertions, inversions or additions of (an) amino acid(s) in said sequence. Amino acid substitutions from which can be expected that they do not essentially alter biological and immunological activities, have been described. Amino acid replacements between related amino acids or replacements which have occurred frequently in evolution are, inter alia Ser/Ala, Ser/Gly, Asp/Gly, Asp/Asn, Ile/Val (see Dayhof, M. D., Atlas of protein sequence and structure, Nat. Biomed. Res. Found., Washington D.C., 1978, vol. 5, suppl. 3). Based on this information Lipman and Pearson developed a method for rapid and sensitive protein comparison (Science 227, 1435–1441, 1985) and determining the functional similarity between homologous polypeptides. Nucleic acid sequences encoding such homologous functional variants are included within the scope of this invention. Moreover, the potential exists to use recombinant DNA technology for the preparation of nucleic acid sequences encoding these various functional variants.

Nucleic acid sequences according to the invention may be derived from isolates of CCV strains such as CCV-6, Insavc-1 (EP 396,193), CCV 1–71 (ATCC VR-809) or CCV TN449 (ATCC VR-2068).

In another aspect of the invention nucleic acid sequences described above are provided which can be used for the preparation of a vaccine to protect cats against FIPV infection.

The information provided in SEQ ID NO: 1–6 allows a person skilled in the art to isolate and identify the nucleic acid sequences encoding the various functional variant polypeptides mentioned-above having corresponding immunological characteristics with the CCV spike protein specifically disclosed herein. The generally applied Southern blotting technique or colony hybridization can be used for that purpose (Experiments in Molecular Biology, ed. R. J. Slater, Clifton, U.S.A., 1986; Singer-Sam, J. et al., Proc. Natl. Acad. Sci. 80, 802–806, 1983; Maniatis T. et al., Molecular Cloning, A laboratory Manual, second edition, Cold Spring Harbor Laboratory Press, USA, 1989). For example, RNA or cDNA derived from a specific CCV strain is electrophoresed and transferred, or "blotted" thereafter onto a piece of nitrocellulose filter. It is now possible to identify CCV spike protein nucleic acid sequences on the filter by hybridization to a defined labeled DNA fragment or "probe", i.e. a (synthetic) poly- or oligonucleotide sequence fragment of the nucleic acid sequence shown in SEQ ID NO: 1, 3 or 5 which under specific conditions of salt concentration and temperature hybridizes to the homologous nucleic acid sequences present on the filter. After washing the filter, hybridized material may be detected by autoradiography. The corresponding DNA fragment can now be eluted from the agarose gel and used to direct the synthesis of a functional variant of the polypeptide disclosed in SEQ ID NO: 2, 4 or 6.

Therefore, a preferred functional variant according to the invention is a polypeptide comprising one or more immunogenic determinants of a CCV spike protein and is encoded by a nucleic acid sequence which hybridizes to the DNA sequence shown in SEQ ID NO: 1, 3 or 5.

In another way CCV cDNA may be cloned into a λgt11 phage as described by Huynh et al. (In: D. Glover (ed.), DNA Cloning: A Practical Approach, IRL Press Oxford, 49–78, 1985) and expressed in a bacterial host. Recombinant phages can then be screened with polyclonal serum raised against the purified CCV spike protein disclosed in SEQ ID NO: 2, 4 or 6 determining the presence of corresponding immunological regions of the variant polypeptide. The production of the polyclonal serum to be used herein elicited against the CCV spike protein is described below.

As is well known in the art, the degeneracy of the genetic code permits substitution of bases in a codon resulting in an other codon but still coding for the same amino acid, e.g. the codon for the amino acid glutamic acid is both GAT and GAA. Consequently, it is clear that for the expression of a polypeptide with the amino acid sequence shown in SEQ ID NO: 2, 4 or 6 use can be made of a derivate nucleic acid sequence with such an alternative codon composition different from the nucleic acid sequence shown in SEQ ID NO: 1, 3 or 5, respectively.

Furthermore, also fragments of the nucleic acid sequences-encoding the specifically disclosed CCV spike protein or functional variants thereof as mentioned above are included in the present invention.

The term "fragment" as used herein means a DNA or amino acid sequence comprising a subsequence of the nucleic acid sequence or polypeptide of the invention. Said fragment is or encodes a polypeptide having one or more immunogenic determinants of a CCV spike protein, i.e. has one or more epitopes which are capable of eliciting a protective immune response in a dog. Methods for determining usable polypeptide fragments are outlined below. Fragments can inter alia be produced by enzymatic cleavage of precursor molecules, using restriction endonucleases for the DNA and proteases for the polypeptides. Other methods include chemical synthesis of the fragments or the expression of polypeptide fragments by DNA fragments.

Typical sequences encoding the CCV spike protein precursor are shown in SEQ ID NO: 1, 3 and 5. These cDNA sequences are about 4328, 4352 and 4358 nucleotides in length, respectively, and encode a polypeptide of 1443, 1451 and 1453 amino acids, respectively.

A preferred nucleic acid sequence according to the invention is characterized in that said sequence contains at least part of the DNA sequence disclosed in SEQ ID NO: 1, 3 or 5.

A nucleic acid sequence according to the invention may be isolated from a particular CCV strain and multiplied by recombinant DNA techniques including polymerase chain reaction (PCR) technology or may be chemically synthesized in vitro by techniques known in the art.

All modifications resulting in the above-mentioned functional variants of the specifically exemplified polypeptide are included within the scope of the present invention for as long as the resulting polypeptides retain one or more immunogenic determinants of a CCV spike protein.

A nucleic acid sequence according to the present invention can be ligated to various replication effecting DNA sequences with which it is not associated or linked in nature resulting in a so called recombinant vector molecule which can be used for the transformation of a suitable host. Useful recombinant vector molecules, are preferably derived from, for example plasmids, bacteriophages, cosmids or viruses.

Specific vectors or cloning vehicles which can be used to clone nucleic acid sequences according to the invention are known in the art and include inter alia plasmid vectors such as pBR322, the various pUC, pGEM and Bluescript plasmids, bacteriophages, e.g. kgt-Wes, Charon 28 and the M13 derived phages or viral vectors such as SV40, adenovirus or polyoma virus (see also Rodriquez, R. L. and D. T. Denhardt, ed., Vectors: A survey of molecular cloning vectors and their uses, Butterworths, 1988; Lenstra, J. A. et al., Arch. Virol. 110, 1–24, 1990). The methods to be used for the construction of a recombinant vector molecule according to the invention are known to those of ordinary skill in the art and are inter alia set forth in Maniatis, T. et al. (Molecular Cloning A Laboratory Manual, second edition; Cold Spring Harbor Laboratory, 1989).

For example, the insertion of the nucleic acid sequence according to .the invention into a cloning vector can easily be achieved when both the genes and the desired cloning vehicle have been cut with the same restriction enzyme(s) as complementary DNA termini are thereby produced.

Alternatively, it may be necessary to modify the restriction sites that are produced into blunt ends either by digesting the single-stranded DNA or by filling in the single-stranded termini with an appropriate DNA polymerase. Subsequently, blunt end ligation with an enzyme such as T4 DNA ligase may be carried out.

If desired, any restriction site may be produced by ligating linkers onto the DNA termini. Such linkers may comprise specific oligonucleotide sequences that encode restriction site sequences. The restriction enzyme cleaved vector and nucleic acid sequence may also be modified by homopolymeric tailing.

"Transformation", as used herein, refers to the introduction of a heterologous nucleic acid sequence into a host cell, irrespective of the method used, for example direct uptake or transduction. The heterologous nucleic acid sequence may be maintained through autonomous replication or alternatively, may be integrated into the host genome. If desired, the recombinant vector molecules are provided with appropriate control sequences compatible with the designated host which can regulate the expression of the inserted nucleic acid sequence. In addition to microorganisms, culture of cells derived from multicellular organisms may also be used as hosts.

The recombinant vector molecules according to the invention preferably contain one or more marker activities that may be used to select for desired transformants, such as ampicillin and tetracycline resistance in pBR322, ampicillin resistance and β-galactosidase activity inpUC8.

A suitable host cell is a microorganism or cell which can be transformed by a nucleic acid sequence encoding a polypeptide or by a recombinant vector molecule comprising such a nucleic acid sequence and which can if desired be used to express said polypeptide encoded by said nucleic acid sequence. The host cell can be of procaryotic origin, e.g. bacteria such as *Escherichia coli, Bacillus subtilis* and Pseudomonas species; or of eucaryotic origin such as yeasts, e.g. *Saccharomyces cerevisia* or higher eucaryotic cells such as insect, plant or mammalian cells, including HeLa cells and Chinese hamster ovary (CHO) cell. Insect cells include the Sf9 cell line of *Spodoptera frugiperda* (Luckow et al., Bio-technology 6, 47–55, 1988). Information with respect to the cloning and expression of the nucleic acid sequence of the present invention in eucaryotic cloning systems can be found in Esser, K. et al. (Plasmids of Eukaryotes, Springer-Verlag, 1986).

In general, prokaryotes are preferred for the construction of the recombinant vector molecules useful in the invention. For example *E. coli* K12 strains are particularly useful such as DH5α or JM101.

For expression nucleic acid sequences of the present invention are introduced into an expression vector, i.e. said sequences are operably linked to expression control sequences. Such control sequences may comprise promoters, enhancers, operators, inducers, ribosome.binding sites etc. Therefore, the present invention provides a recombinant vector molecule comprising a nucleic acid sequence encoding the CCV spike protein operably linked to expression control sequences, capable of expressing the DNA sequences contained therein in (a) transformed host cell(s).

It should, of course, be understood that the nucleotide sequences inserted at the selected site of the cloning vector may include nucleotides which are not part of the actual structural gene for the desired polypeptide or may include only a fragment of the complete structural gene for the desired protein as long as transformed host will produce a polypeptide having at least one or more immunogenic determinants of a CCV spike protein.

When the host cells are bacteria, illustrative useful expression control sequences include the Trp promoter and operator (Goeddel, et al., Nucl. Acids Res. 8, 4057, 1980); the lac promoter and operator (Chang, et al., Nature 275, 615, 1978); the outer membrane protein promoter (Nakamura, K. and Inouge, M., EMBO J. 1, 771–775, 1982); the bacteriophage promoters and operators (Remaut, E. et al., Nucl. Acids Res. 11, 4677–4688, 1983); the α-amylase (*B. subtilis*) promoter and operator, termination sequence and other expression enhancement and control sequences compatible with the selected host cell. When the host cell is yeast, illustrative useful expression control sequences include, e.g., α-mating factor. For insect cells the polyhedrin or p10 promoters of baculoviruses can be used (Smith, G. E. et al., Mol. Cell. Biol. 3, 2156–65, 1983). When the host cell is of mammalian origin illustrative useful expression control sequences include, e.g., the SV-40 promoter (Berman, P. W. et al., Science 222, 524–527, 1983) or, e.g. the metallothionein promoter (Brinster, R.L., Nature 296, 39–42, 1982) or a heat shock promoter (Voellmy et al., Proc. Natl. Acad. Sci. USA 82, 4949–53, 1985). For maximizing gene expression, see also Roberts and Lauer (Methods in Enzymology 68, 473, 1979).

Therefore, the invention also comprises (a) host cell(s) transformed with a nucleic acid sequence or recombinant expression vector molecule described above, capable of producing the CCV spike protein by expression of the nucieic acid sequence.

The present invention also provides a process for the preparation of a purified polypeptide displaying immunological characteristics of a CCV spike protein, i.e. the polypeptide has one or more immunogenic determinants of a CCV spike protein,. essentially free from whole viruses or other protein with which it is ordinarily associated.

More particularly, the invention provides a process for the preparation of a polypeptide comprising at least part of the amino acid sequence shown in SEQ ID NO: 2, 4 or 6 or a functional variant thereof.

In ·addition a polypeptide substantially comprising an immunogenic fragment of the CCV spike protein which can be used for immunization of dogs against CCV infection or diagnostic purposes, is prepared in the present invention. Various methods are known for detecting such usable immunogenic fragments within an amino acid sequence.

Suitable immunochemically active polypeptide fragments of a polypeptide according to the invention containing (an) epitope(s) can be found by means of the method described in Patent Application WO 86/06487, Geysen, H. M. et al. (Prod. Natl. Acad. Sci. 81, 3998–4002, 1984), Geysen, H. M. et al. (J. Immunol. Meth. 102, 259–274, 1987) based on the so-called pepscan method, wherein a series of partially overlapping peptides corresponding with partial sequences of the complete polypeptide under consideration, are synthesized and their reactivity with antibodies is investigated.

In addition, a number of regions of the polypeptide, with the stated amino acid sequence, can be designated epitopes on the basis of theoretical considerations and structural agreement with epitopes which are now known. The determination of these regions is based on a combination of the hydrophilicity criteria according to Hopp and Woods (Proc. Natl. Acad. Sci. 78, 3824–3828, 1981) and the secondary structure aspects according to Chou and Fasman (Advances in Enzymology 47, 45–148, 1987).

T-cell epitopes which may be necessary can likewise be derived on theoretical grounds, e.g. with the aid of Berzofsky's amphiphilicity criterion (Science 235, 1059–62, 1987).

In another embodiment of the invention a polypeptide having an amino acid sequence encoded by a nucleic acid sequence mentioned above is used.

Immunization of dogs against CCV infection can, for example be achieved by administering to the animals a polypeptide prepared according to the process mentioned above in an immunologically relevant context as a so-called subunit vaccine. The subunit vaccine according to the invention may comprise a polypeptide in a pure form, optionally in the presence of a pharmaceutically acceptable carrier. The polypeptide can optionally be covalently bound to a non-related protein, which, for example can be of advantage in the purification of the fusion product. Examples are β-galactosidase, protein A, prochymosine, blood clotting factor Xa, etc.

In some cases the ability to raise neutralizing antibodies against these polypeptides per se may be low. Small fragments are preferably conjugated to carrier molecules in order to raise their immuno-genicity. Suitable carriers for this purpose are macromolecules, such as natural polymers (proteins like key hole limpet hemocyanin, albumin, toxins), synthetic polymers like polyamino acids (polylysine, polyalanine), or micelles of amphiphilic compounds like saponins. Alternatively these fragments may be provided as polymers thereof, preferably linear polymers.

Polypeptides to be used in such subunit vaccines can be prepared by methods known in the art, e.g. by isolating said polypeptides from CCV, by recombinant DNA techniques or by chemical synthesis.

If required these polypeptides to be used in a vaccine can be modified in vitro or in vivo, for example by glycosylation, amidation, carboxylation or phosphorylation.

An alternative to subunit vaccines are live vector vaccines. A nucleic acid sequence according to the invention is introduced by recombinant DNA techniques into a micro-organism (e.g. a bacterium or virus) in such a way that the recombinant micro-organism is still able to replicate thereby expressing a polypeptide coded by the inserted nucleic acid sequence and eliciting an immune response in the infected host animal.

A preferred embodiment of the present invention is a recombinant vector virus comprising a heterologous nucleic acid sequence described above, capable of expressing the DNA sequence in (a) host cell(s) or host animal infected with the recombinant vector virus. The term "heterologous" indicates that the nucleic acid sequence according to the invention is not normally present in the vector virus.

Furthermore, the invention also comprises (a) host cell(s) or cell culture infected with the recombinant vector virus, capable of producing the CCV protein by expression of the nucleic acid sequence.

For example the well known technique of in vivo homologous recombination can be used to introduce a heterologous nucleic acid sequence, e.g. a nucleic acid sequence according to the invention into the genome of the vector virus.

First, a DNA fragment corresponding with an insertion region of the vector genome, i.e. a region which can be used for the incorporation of a heterologous sequence without disrupting essential functions of the vector such as those necessary for infection or replication, is inserted into a cloning vector according to standard recDNA techniques. Insertion-regions have been reported for a large number of micro-organisms (e.g. EP 80,806, EP 110,385, EP 83,286, U.S. Pat. No. 4,769,330 and U.S. Pat. No. 4,722,848).

Second, if desired, a deletion can be introduced into the insertion region present in the recombinant vector molecule obtained from the first step. This can be achieved for example by appropriate exonuclease III digestion or restriction enzyme treatment of the recombinant vector molecule from the first step.

Third, the heterologous nucleic acid sequence is inserted into the insertion-region present in the recombinant vector molecule of the first step or in place of the DNA deleted from said recombinant vector molecule. The insertion region DNA sequence should be of appropriate length as to allow homologous recombination with the vector genome to occur. Thereafter, suitable cells can be infected with wild-type vector virus or transformed with vector genomic DNA in the presence of the recombinant vector molecule containing the insertion flanked by appropriate vector DNA sequences whereby recombination occurs between the corresponding regions in the recombinant vector molecule and the vector genome. Recombinant vector progeny can now be produced in cell culture and can be selected for example genotypically or phenotypically, e.g. by hybridization, detecting enzyme activity encoded by a gene co-integrated along with the heterologous nucleic acid sequence, or detecting the antigenic heterologous polypeptide expressed by the recombinant vector immunologically.

Next, this recombinant micro-organism can be administered to the dogs for immunization whereafter it maintains itself for some time, or even replicates in the body of the inoculated animal, expressing in vivo a polypeptide coded for by the inserted nucleic acid sequence according to the invention resulting in the stimulation of the immune system of the inoculated animal. Suitable vectors for the incorporation of a nucleic acid sequence according to the invention can be derived from viruses such as pox viruses, e.g. vaccinia virus (EP 110,385, EP 83,286, U.S. Pat. No. 4,769,330 and U.S. Pat. No. 4,722,848), herpes viruses such as Feline Herpes virus, (canine) adeno virus (WO 91/11525) or influenza virus, or bacteria such as E. coli or specific Salmonella species. With recombinant microorganisms of this type, the polypeptide synthesized in the host can be exposed as a cell surface antigen. In this context fusion of the said polypeptide with OMP proteins, or pilus proteins of for example E. coli or synthetic provision of signal and anchor sequences which are recognized by the organism are conceivable. It is also possible that the said immunogenic polypeptide, if desired as part of a larger whole, is released inside the animal to be immunized. In all of these cases it is also possible that one or more immunogenic products will find expression which generate protection against various pathogens and/or against Various antigens of a given pathogen.

A vaccine according to the invention can be prepared by culturing a host cell infected with a recombinant vector virus comprising a nucleic acid sequence according to the invention, whereafter virus containing cells and/or recombinant vector viruses grown in the cells can be collected, optionally in a pure form, and formed to a vaccine optionally in a lyophilized form.

Host cells transformed with a recombinant vector molecule according to the invention can also be cultured under conditions which are favourable for the expression of a polypeptide coded by said nucleic acid sequence. Vaccines may be prepared using samples of the crude culture, host cell lysates or host cell extracts, although in another embodiment more purified polypeptides according to the invention are formed to a vaccine, depending on its intended use. In order to purify the polypeptides produced, host cells transformed with a recombinant vector according to the invention are cultured in an adequate volume and the polypeptides produced are isolated from such cells from the medium if the protein is excreted. Polypeptides excreted into the medium can be isolated and purified by standard techniques, e.g. salt fractionation, centrifugation, ultrafiltration, chromatography, gel filtration or immuno affinity chromatography, whereas intra cellular polypeptides can be isolated by first collecting said cells, disrupting the cells, for example by sonication or by other mechanically disruptive means such as French press followed by separation of the polypeptides from the other intra cellular components and forming the polypeptides to a vaccine. Cell disruption could also be accomplished by chemical (e.g. EDTA treatment) or enzymatic means such as lysozyme digestion.

The vaccine according to the invention can be administered in a convential active immunization scheme: single or repeated administration in a manner compatible with the dosage formulation and in such amount as will be prophylactically and/or therapeutically effective and immunogenic, i.e. the amount of immunizing antigen or recombinant micro-organism capable of expressing said antigen that will induce immunity in a dog against challenge by a virulent CCV. Immunity is defined as the induction of a significant level of protection in a population of dogs after vaccination compared to an unvaccinated group.

For live viral vector vaccines the dose rate per dog may range from $10^5$–$10^8$ pfu.

A typical subunit vaccine according to the invention comprises 10 µg–1 mg of the polypeptide according to the invention.

The administration of the vaccine can be done, e.g. intradermally, subcutaneously, intramuscularly, intraperitonially, intravenously, orally or intranasally.

Additionally the vaccine may also contain an aqueous medium or a water containing suspension, often mixed with other constituents, e.g. in order to increase the activity and/or shelf life. These constituents may be salts, pH buffers, stabilizers (such as skimmed milk or casein hydrolysate), emulsifiers adjuvants to improve the immune response (e.g. oils, muramyl dipeptide, aluminum hydroxide saponin, polyanions and amphipatic substances) and preservatives.

It is clear that a vaccine according to the invention may also contain immunogens related to other pathogens of dogs or may contain nucleic acid sequences encoding these immunogens, like antigens of Canine parvovirus (CPV), Canine Distemper virus, Canine Adenovirus I, Canine Adenovirus II, Canine Parainfluenza virus, Canine Rotavirus or *Lepotospira canicola* to produce a multivalent vaccine.

EXAMPLE 1

A.

1. Preparation of genomic viral RNA of CCV-6 and Liverpool C54 strain

Confluent A-72 cells grown in plastic tissue culture flasks using the Wellcome modification of minimal Eagle's medium (MEM) and 10% foetal bovine serum were infected with CCV (NVSL Challenge virus CCV-6 from the National Veterinary Service Laboratory, PO Box 844, Ames, Iowa 50010, USA) at a multiplicity of infection (MOI) of approximately 0.1. After 24 h the culture supernatant was harvested, chilled to 4° C. and cell debris removed by centrifugation at 3000×g for 15 min. Virus was pelletted from the supernatant at 53.000× g for 2 h in a Beckman type 19 rotor. The pellet was resuspended in 5 ml of TNE (10 mM Tris-Cl, 100 mM NaCl, 1 mM EDTA, pH 7.5) using a Dounce homogeniser and layered onto a 32 ml linear 20–60% gradient of sucrose in TNE. The virus was banded isopycnically by overnight centrifugation at 100.000 ×g in a Beckman SW28 rotor. The gradient was fractionated and the $A_{280}$'s and densities of the fractions determined. A peak was identified at the characteristic density of 1.18 g/cc. The peak fractions were pooled, diluted in TNE and the putative virus pelletted by centrifugation at 100.000×g for 2 h in the Beckman SW28 rotor. RNA was isolated from the virus pellet using two approaches:

A. The pellet was resuspended in 0.1M Tris Cl pH 8.0 containing 0.1% SDS and digested for 3 h at 50° C. with 20 µg/ml of proteinase K. The mixture was deproteinised using phenol:chloroform:isoamyl alcohol (50:49:1) saturated with TE (10 mM Tris-Cl 1 mM EDTA) and the nucleic acid recovered by precipitation with 2.5 volumes of ethanol/0.3M sodium acetate pH 5.2. The preparation was analysed on a Tris-borate EDTA 1% agarose gel containing 0.1% SDS; a high molecular weight RNA band was identified with the characteristic mobility of coronavirus genomic RNA.

B. The virus pellet was homogenised in 6M guanidinium isothiocyanate/5 mM sodium citrate (pH 7.0)/0.1M mercaptoethanol/0.5% N-lauroyl sarcosinate and 1 g/ml of CsCl added to each 2.5 ml of the homogenate. The mixture was then layered onto a 5.7 M CsCl/0.1M EDTA pad and centrifuged at 108.000×g for 12 h at 20° C. The pellet of RNA was dissolved in TE containing 0.1% SDS. The preparation was analysed as described above.

2. cDNA cloning of CCV genomic RNA

First strand synthesis from 2 µg of CCV genomic RNA prepared as described in 1A above was primed with 1 ng of a specific oligonucleotide (5' TTTTCAAATTGTCTTCTACTT 3') (SRQ ID NO:7) using 40 units of AMV reverse transcriptase in a reaction volume of 25 µl containing 20 mM Tris-Cl (pH 8.3 at 42° C.), 0.14M KCl, 10 mM $MgCl_2$, 1 mM dNTP's, 4 mM dithiothreitol, 25 units of human placental ribonuclease inhibitor. The reaction mixture was incubated for 1 h at 42 ° C. Second strand synthesis was achieved by addition of 46 µl of a reaction mixture containing 7.6 mM $MgCl_2$, 0.109M Tris-Cl pH 7.4 16.3 mM $(NH_4)_2SO_4$, 1000 units/ml RNaseH 10.000 units/ml *E. coli*

DNA polymerase 1 to the first strand reaction and incubation at 12° C. for 1 h followed by incubation at 22° C. for a further 1 h. The reaction products were deproteinised by two extractions with phenol: chloroform: isoamyl alcohol (50:49:1) saturated with TE and precipitated with 2 volumes of ethanol/0.3M sodium acetate pH 5.2. The cDNA was tailed with C residues using terminal deoxynucleotidyl transferase using the buffer and conditions supplied by the manufacturer (Bethesda Research Laboratories, Gaithersburg, Md. 20877, USA). It was then size fractionated on a 2 ml Sephacryl S-1000 column and cDNA of size greater than 500 base pairs pooled, ethanol precipitated and dissolved in TE 50 ng of this cDNA was annealed with 250 ng of detailed PstI cut pUC119. The mixture was transformed into E. coli TG-1. Ampicillin resistant transformants were picked and screened for CCV cDNA inserts using a cDNA probe produced by random priming of reverse transcription from CCV genomic RNA. Positive colonies were screened for size of cDNA inserts by PstI digestion of mini-prep DNA. The relationships between inserts were established by restriction enzyme analysis. The clone pBH1 was selected for sequence analysis. The size of the pBH1 insert (4.0 kb) was insufficient to cover the complete CCV spike coding region and a further round of cDNA synthesis and cloning was carried out using another specific primer (5' CTAGGTAGTAACAC 3') (SEQ ID NO:8). The RNA used was isolated as described in 1B above cDNA synthesis was achieved using a Boehringer Mannheim (Boehringer Mannheim UK, Bell Lane, Lewes, East Sussex BN7 1 LG) cDNA synthesis kit according to the manufacturer's instructions. In summary first strand synthesis was again achieved using AMV reverse transcriptase, second strand synthesis by the action of E. coli DNA polymerase 1 and RNaseH. The cDNA was blunt ended by the action of T4 DNA polymerase. The cDNA was ligated into SmaI-cut phosphatased pUC18 using T4 DNA ligase and the DNA transformed into E. coli TG1. Ampicillin resistant clones were initially screened for inserts using blue/white selection on X-gal (5-bromo-4-chloro-3-indolyl-β-D-galactopyranoside) plates. White colonies were picked and screened for the presence of CCV cDNA inserts as described above. Clone pBH2 (size 2.8 kb) was selected for sequence analysis. The same strategy as outlined in Example 1.1.B. and 1.2. for CCV strain CCV6 was carried out for the isolation of the spike gene of the CCV C54 strain. Three overlapping clones, pBH3, pBH4 and pBH11 covered the spike gene to the blunt end.

3. DNA sequencing

The cDNA inserts from clones pBH1, pBH2, and pBH3, pBH4 and pBH11 were sequenced using the Sanger dideoxy chain termination method. This shotgun approach was supplemented as necessary with sequencing from specific oligonucleotide primers on double stranded plasmid DNA templates. For the shotgun analysis insert DNA was excised from the vector sequences, circularised, sonicated, size selected on agarose gels and cloned into SmaI-cut, phosphatased M13mp8. Shotgun sequence data were assembled using the DBUTIL and DBAUTO programs of Staden and analysed using the ANALYSEQ/NIP packages of Staden. A VAX 8350 and micro VAX 3100 (Digital Equipment Corporation) were used. The sequence data are presented in SEQ ID NO: 1 and 5.

B.

1. Preparation of genomic viral RNA of Insavc-1 strain

Confluent A-72 cells grown in plastic tissue culture flasks using the Wellcome modification of minimal Eagle's medium (MEM) and 10% F.C.S. were infected with CCV strain Insavc-1 (Bert) (Intervet Labs.) at a m.o.i. of approximately 0.1. After 48 hours the culture supernatant was harvested, chilled to 4° and cell debris removed by Centrifugation at 3000×g for 15 minutes. Virus was pelleted from the supernatant at 53000×g for 2 hrs in a Beckman type 19 rotor. The virus pellet was homogenized in 3.5 mls of 6M guanidinium isothiocyanate/5 mM sodium citrate (pH 7.0), 0.1M mercaptoethanol, 0.5% N-lauroyl sarcosinate.

The homogenate was layered onto a 5.7M CsCl pad (1 ml) and Centrifuged at 108,000 g for 18 hours at 18° C. The pellet of RNA was dissolved in TE containing 0.1% SDS, then precipitated twice with 2.5 volumes of ethanol/0.3M NaOAc pH 5.2. The preparation was analysed as a Trisborate EDTA 1% agarose gel containing 0.1% SDS, high molecular weight RNA band was identified with the characteristic mobility of coronavirus genomic RNA.

2. cDNA and PCR cloning of CCV genomic RNA

First and second strand synthesis from 2 µg of CCV genomic. RNA prepared as aforementioned was primed with oligo dT and random pentanucleotides from the Boehringer cDNA synthesis kit under the conditions specified by the manufacturers protocol.

The resultant blunt ended EDNA produced from this reaction was ligated into SmaI-cut phosphatased pUC 119 using T4 DNA ligase and the DNA transformed into E. coli TG-1. Ampicillin resistant clones were initially screened for inserts using blue/white selection on x-gal (5-bromo-4-chloro-3-indetyl-B-D-galaclopyramoside) plates. White colonies were picked and screened for the presence of ccv cDNA inserts using randomly primed CCV RNA as a probe. Five positive clones were identified.

Plasmid pBH6 was generated using the polymerase chain reaction (PCR). Sequence information from the ends of pBH5 and pHB7 allowed the design of primers BH7 and BH8. A Not I site was incorporated into the oligo's to facilitate cloning. Briefly, approximately 1 ng of first-strand reaction as described previously was deproteinized by two extractions with phenol:chloroform:Isoramyl alcohol (50:49:1) saturated with TE, passed down a G50 spin column and precipitated with two volumes of ethanol/0.3M sodium acetate pH 5.2. The DNA:RNA hybrids were resuspended in 15 µl TE. The PCR reaction was carried out with the Techne programmable Dri-block PHC-1.

The generated fragment was phenol/chloroform ethanol precipitated as before and resuspended in 20 µl of TE. The DNA was cleaved with Not 1 under conditions recommended by the enzyme manufacturer, and gel eluted. The Not 1 fragment was then ligated to Not 1 cut phosphatased vector using T4 DNA ligase and the DNA transformed into E. coli TG-1. Clones containing inserts were identified as previously described.

3. DNA sequencing

The cDNA inserts from clones pBH5, pBH7, pBH8, pBH9, pBH10 and the PCR insert pBH6, were sequenced using the Sanger dideoxy chain terminations method as described by Barrell and Bankier (Methods in Enzymology 155, 51–93, 1987). This shotgun approach was supplemented as necessary with sequencing from specific oligonucleotide primers on double stranded or single stranded (fl origin in pUC 119) plasmid DNA. For shotgun analyses, insert DNA was excised from the vector sequences, self ligated, sonicated, end-repaired, size selected on 1% agarose gels, cloned into SmaI-cut phosphatased M13mp18. Shotgun sequence data were assembled and analysed using the SAP programmes of Standen. A Vax 8350 and MicroVax 3100 (Digital Equipment Corporations) were used. The sequence-data are presented SEQ ID NO.: 3.

EXAMPLE 2

2.1. Generation of vaccinia virus Vac4b-C6

2.1.1. Assembly of CCV6 full length spike protein gene.

The full length coding region of the S gene of CCV6 was reconstructed from 2 overlapping cDNA clones, BH1 and BH2. The cloning strategy is illustrated in FIG. 1. The 3.0 kb insert from pBH1 has identity to S and 1b. In order to express S, the polymerase coding sequence had to be removed. The sequence immediately 5' of the initiating methionine, CTAAACTTTGGTAATCACTTGG TTAAT-GTGCC ATG (SEQ ID NO:9) was modified by site directed mutagenesis. Four bases, ATCC were looped in between the TGG and TTA bases to create a unique BamHI site, GGATCC. Mutants were screened by restriction enzyme digestion. Positive clones were sequenced across this site as the Klenow fragment of E. coli DNA polymerase used in the mutagenesis reaction can introduce unspecified mutations at a very low frequency. A mutant which had the introduced BamHI site was selected and designated pBHI-bam. This plasmid overlapped pBH2 by approximately 300 bp. A unique AflII site was located in this region of overlap. The proximal S coding sequence was isolated from pBHI-bam as a 1.5 kb AflII-SphI fragment and ligated into HfIII-SPHI digested pBH2 generating pCCV6. The full length S coding sequence was isolated as a 4.4 kb BamHI fragment then ligated into the BAMHI site of the transfer vector RK19 to form pRKCCV6. Correct orientation of the gene was confirmed by restriction enzyme digestion. Thus, the plasmid RKCCV6 contains the CCV6 S gene downstream of the 4b promoter and flanked by TK coding sequences.

2.1.2. Isolation of recombinant virus

Recombinant vaccinia viruses were constructed by established procedures (Mackett & Smith, J.Gen. Virol. 67, 2067–2082, 1986). pRKCCV6 was transfected into vaccinia virus infected cells and recombinant viruses identified by dot-blot hybridisation using random primed $^{32}p$ labelled CCV6 spike gene as a probe. Plaque purification and screening were repeated 3 times before stocks were prepared. The recombinant derived from pRKCCV6 was named Vac4b-C6.

2.2 Generation of vaccinia virus Vac4b-IN

2.2.1. Assembly of CCV Insavc-1 full length spike protein gene

Figure 2A:
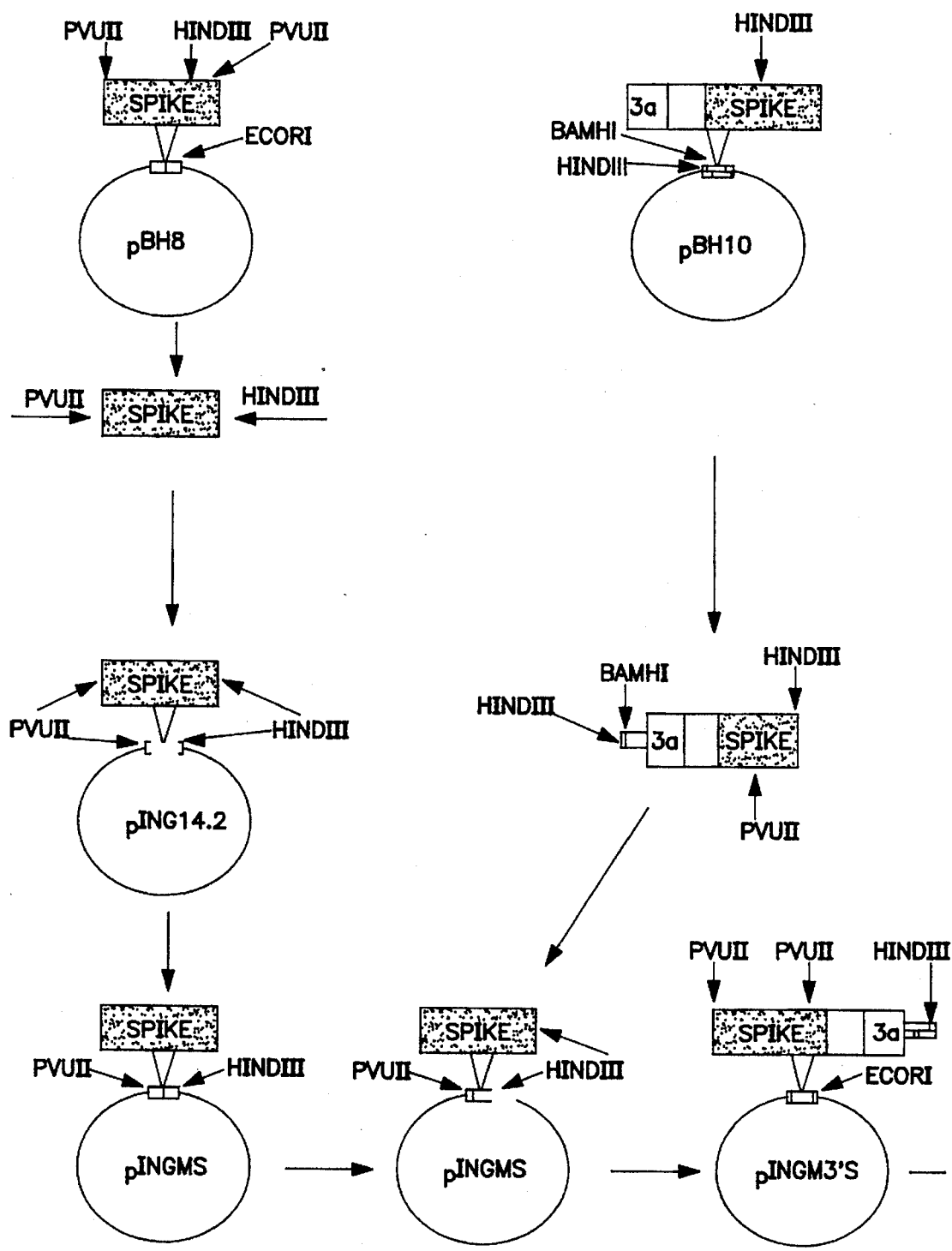
FIG. 2A and B shows the cloning strategy for the construction of plasmid pRKINSAVC-1 from plasmids pBH8, pBH10 and pBH9.
Figure 2B:
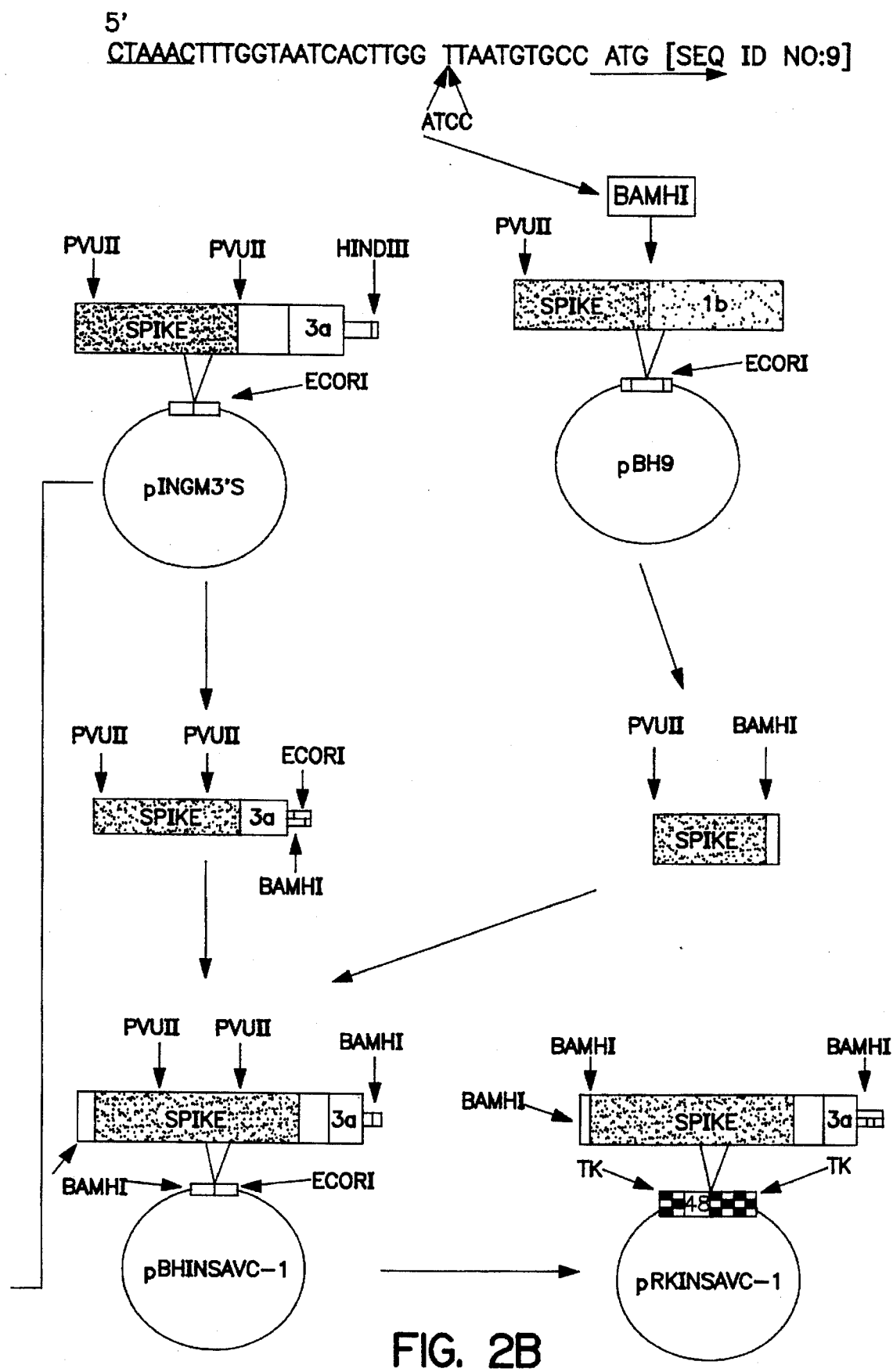

The Insavc-1 (Bert) S gene was assembled from 3 overlapping cDNA clones BH8, BH9 and BH10. The cloning strategy is illustrated in FIG. 2. Digesting pBH8, which spans the middle of the S gene with PvuII and HindIII yielded a 1.4 kb fragment. This fragment was ligated into a PvuII-HindIII cut vector, pING14.2 forming INGMS. This plasmid was linearized with HindIII phosphatased then gel eluted. The 3' S gene coding sequence isolated as a 1.1 kb HindIII fragment from pBH10, was subcloned into HindIII cut pINGMS generated pINGM3'S. Correct orientation of the cloned HindIII fragment was confirmed by restriction enzyme digestion. Before the remaining coding sequence was excised from pBH9 a unique BamHI site was introduced 10 bps upstream of the peplomer AUG start codon by site-directed mutagenesis (FIG. 2). The 5' coding sequence of the S gene was isolated as a 1.9 kb PvuII fragment and the remaining S gene coding sequence, which was isolated as a 2.5 kb partial-EcoRI fragment from pING3s, were ligated in a two fragment ligation to BamHI-EcoRI digested pUC118. The complete S protein gene coding sequence was isolated as 4.4 kb BamH1 fragment and subcloned into the BamHI cut transfer vector pRK19, generating pRKINSAVC-1. Correct orientation of the gene was confirmed by restriction enzyme digestion. Thus the plasmid RKINSAVC-1 contains the CCV-INSAVC-1 S gene downstream of the vaccinia 4b promoter and flanked by TK coding sequences.

2.2.2. Isolation of recombinant vaccinia virus

Plasmid RKINSAVC-1 was used to introduce the S gene coding sequence into vaccinia virus by transfection and selection for TK⁻ recombinants was as described by Mackett and Smith, (1986, ibid). Recombinant virus isolates identified by dot blot hybridisation with a $^{32}p$ labelled CCV6 S DNA probe were subjected to three rounds of plaque purification and virus stocks prepared. The recombinant derived from RKINSAVC-1 was named Vac4b-IN.

2.3. Generation of vaccinia virus Vac4b-C54

2.3.1. Assembly of CCV C54 full length S protein gene

Figure 3:
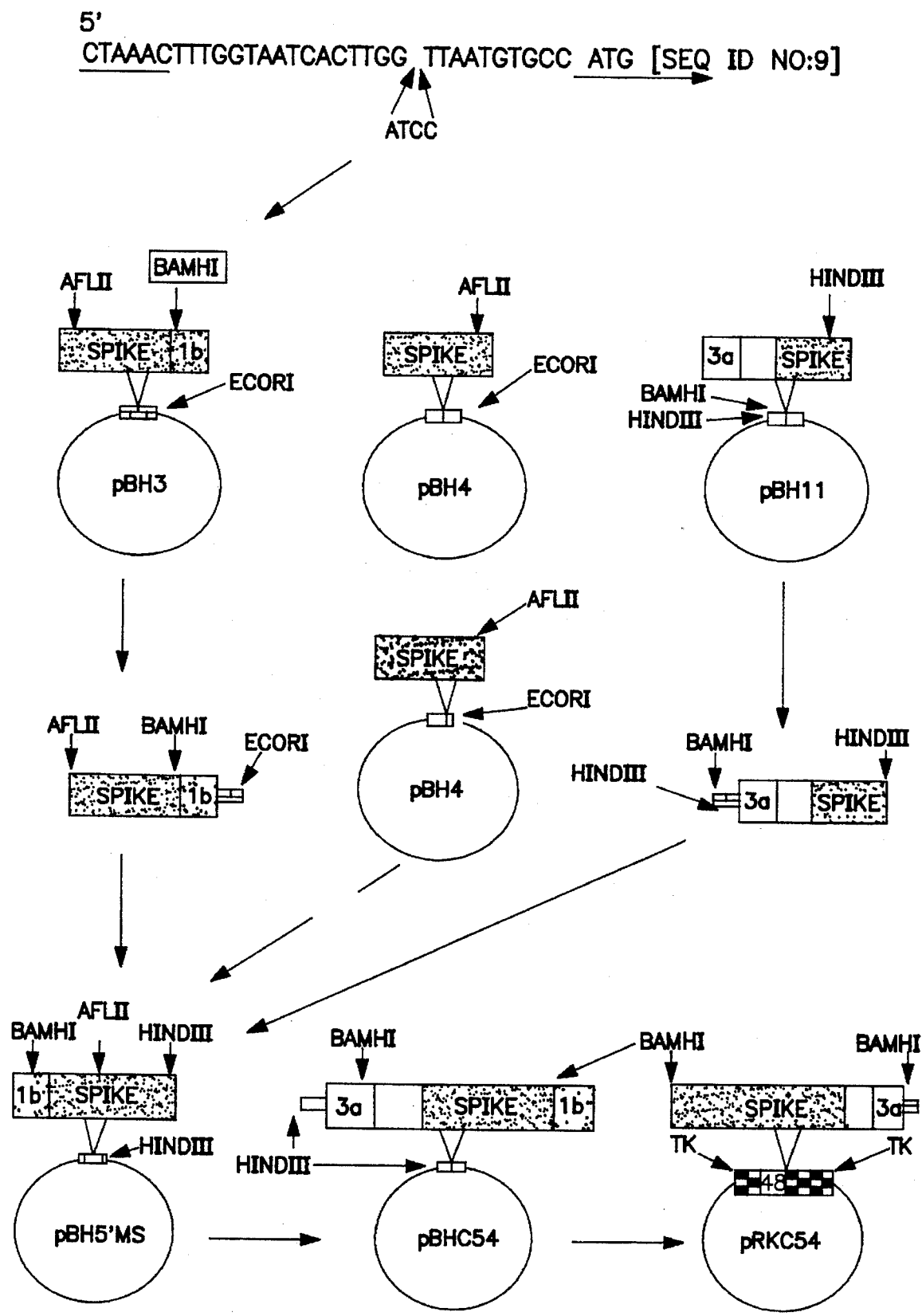
FIG. 3 shows the cloning strategy for the construction of plasmid pRKC54 from plasmids pBH3, pBH4 and pBH11.

The C54 S gene coding sequence was assembled from the 3 overlapping clones pBH3, pBH4 and pBH11. A unique BamH1 site was created 10' bps upstream of the peplomer AUG start codon by site-directed mutagenesis in the proximal clone, pBH3 generating pBH3-bam (FIG. 3). A 2.0 kb AftI-EcoRI fragment was isolated from this plasmid and ligated to AflI-EcoRI digested pBH4 forming pBH5'MS. This plasmid was cleaved with HindIII, phosphatased and gel eluted. The 3' coding sequence was excised as a 1.1 kb fragment from pBH11, then lighted to the HindIII digested pBH5'MS generating pBHC54. The correct orientation of the subcloned HindIII fragment was determined by restriction enzyme digestion. The full length C54 S gene was excised by digestion with BamHI from pBHC54 and ligated into the BamHI cut transverse vector RK19, forming pRKC54. Similarly, the orientation of the S gene was determined by restriction enzyme digestion. Thus the plasmid RKC54 contains the CCV C54 S gene downstream of the 4b promoter and flanked by TK coding sequences. The cloning strategy is illustrated in FIG. 3.

2.3.2. Isolation of recombinant vaccinia virus

Plasmid RKC54 was transfected into vaccinia virus infected cells. TK⁻ recombinants were selected using BUdR (Mackett and Smith, 1986, ibid). Recombinant virus isolates were identified by dot-blot hybridisation and subjected to three rounds of plaque purification before stocks were made. The recombinant derived from pRKC54 was named Vac4b-C54.

EXAMPLE 3

Immunization experiments with live recombinant Vaccinia vaccine

3.1. Immunization

Cats were vaccinated with the following vaccines ($10^7$ pfu/cat):

(a) 4 cats—Vac4b-IN (b) 4 cats—Vac4b-C6

(c) 2 cats—Vac4b-gB (Vac4b-gB is recombinant Vaccinia virus which expresses the Cytomegalovirus glycoprotein gB under control of the 4b promoter)

(d) 2 cats—unvaccinated.

All cats were bled prior to vaccination (Bleed A). 3 weeks after vaccination the cats were bled again (Bleed B) and subsequently re-vaccinated as above.

2 weeks after re-vaccination all cats were bled (Bleed C).

3.2. Immuno-precipitation

Canine A72 cells were infected at a m.o.i. of about 10 with the recombinant viruses or mock-infected, incubated for 16 hours and starved of methionine for 1 hour. Infected cells were labelled with $^{35}$S methionine and incubated for 30 min., washed and subsequently lysed in R.I.P.A. buffer. 1 μl cat antiserum (Bleed C) was added to the radiolabelled lysate and incubated on ice for 60 min. Protein G is added and incubated on ice for 60 min. After washing the protein G in R.I.P.A. buffer and PBS buffer, the bound proteins are recovered with 2% SDS 2% 2-mercapto-ethanol. The proteins are separated on 10% SDS polyacrylamide gel.

Sera from Bleed C precipitated the spike protein in the case of cats given Vac4b-C6 and Vac4b-IN. Thus, the cats immunized with the Vaccinia recombinant virus containing the spike genes responded with antibodies to the spike genes.

---

We claim:

1. An isolated and purified DNA molecule which corresponds to a subgenomic part of the Canine Coronavirus RNA and codes for a Canine Coronavirus spike protein comprising an amino acid sequence selected from the group consisting of SEQ ID Nos: 2, 4, and 6.

2. The DNA molecule according to claim 1, wherein the DNA molecule comprises a sequence selected from the group consisting of SEQ ID NO:1, 3 and 5.

3. A recombinant vector molecule comprising the DNA molecule according to claim 1.

4. A recombinant vector molecule according to claim 3, wherein the DNA molecule is operably linked to an expression control sequence.

5. A recombinant virus vector comprising the DNA molecule according to claim 1.

6. A host cell transformed with the vector of any one of claims 3–5.

7. A host cell transformed with a recombinant vector molecule according to claim 3.

8. A host cell infected with a recombinant virus vector according to claim 5.

9. A process for the preparation of a Canine Coronavirus spike protein, which process comprises:

(a) culturing the host cell according to claim 1 under conditions in which the DNA is expressed, and (b) isolating the Canine Coronavirus spike protein from the culture.

* * * * *

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
        ( A ) LENGTH: 4500 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Canine corona virus
        ( B ) STRAIN: CCV-6

( i x ) FEATURE:
        ( A ) NAME/KEY: CDS
        ( B ) LOCATION: 65..4393
        ( D ) OTHER INFORMATION: /label=CCV6_Spikegene ( x i ) SEQUENCE DESCRIPTION: SEQ ID NO:1:

```
GTAAGTTGCT  CATTAGAAAC  AATGGAAAAC  TACTAAACTT  TGGTAATCAC  TTGGTTAATG      60

TGCC ATG ATT GTG CTA ATA TTG TGC CTC CTC TTG TTT TCG TAC AAT AGT          109
     Met Ile Val Leu Ile Leu Cys Leu Leu Leu Phe Ser Tyr Asn Ser
     1               5                  10                  15

GTG ATT TGT ACA TCA AAC AAT GAC TGT GTA CAA GTT AAT GTG ACA CAA           157
Val Ile Cys Thr Ser Asn Asn Asp Cys Val Gln Val Asn Val Thr Gln
                 20                  25                  30

TTG CCT GGC AAT GAA AAC ATT ATT AAA GAT TTT CTA TTT CAC ACC TTC           205
Leu Pro Gly Asn Glu Asn Ile Ile Lys Asp Phe Leu Phe His Thr Phe
             35                  40                  45

AAA GAA GAA GGA AGT GTA GTT GTT GGT GGT TAT TAC CCT ACA GAG GTG           253
Lys Glu Glu Gly Ser Val Val Val Gly Gly Tyr Tyr Pro Thr Glu Val
         50                  55                  60

TGG TAT AAC TGC TCC AGA AGC GCA ACA ACC ACC GCT TAC AAG GAT TTT           301
Trp Tyr Asn Cys Ser Arg Ser Ala Thr Thr Thr Ala Tyr Lys Asp Phe
     65                  70                  75

AGT AAT ATA CAT GCA TTC TAT TTT GAT ATG GAA GAC ATG GAG AAA AGC           349
Ser Asn Ile His Ala Phe Tyr Phe Asp Met Glu Asp Met Glu Lys Ser
 80                  85                  90                  95

ACT GGC AAT GCA CGA GGA AAA CCT TTA CTA GTA CAT GTT CAT GGT GGA           397
Thr Gly Asn Ala Arg Gly Lys Pro Leu Leu Val His Val His Gly Gly
                 100                 105                 110
```

| | | | | | | | | | | | | | | | | |
|---|---|---|---|---|---|---|---|---|---|---|---|---|---|---|---|---|
| CCT | GTT | AGT | ATC | ATC | ATT | ATA | TGT | GCA | AGG | AAG | GCC | TCT | TTA | AAA | CAT | 445 |
| Pro | Val | Ser | Ile | Ile | Ile | Ile | Cys | Ala | Arg | Lys | Ala | Ser | Leu | Lys | His | |
| | | | 115 | | | | 120 | | | | | | 125 | | | |
| GGT | TTG | TTG | TGT | ATA | ACT | AAA | AAT | AAA | ATC | ATT | GAC | TAT | AAC | ACG | TTT | 493 |
| Gly | Leu | Leu | Cys | Ile | Thr | Lys | Asn | Lys | Ile | Ile | Asp | Tyr | Asn | Thr | Phe | |
| | | 130 | | | | | 135 | | | | | 140 | | | | |
| ACC | AGC | GCA | CAG | TGG | AGT | GCC | ATA | TGT | TTG | GGT | GAT | GAC | AGA | AAA | ATA | 541 |
| Thr | Ser | Ala | Gln | Trp | Ser | Ala | Ile | Cys | Leu | Gly | Asp | Asp | Arg | Lys | Ile | |
| | 145 | | | | | 150 | | | | | 155 | | | | | |
| CCA | TTC | TCT | GTC | ATA | CCC | ACA | GAT | AAT | GGT | ACA | AAA | ATA | TTT | GGT | CTT | 589 |
| Pro | Phe | Ser | Val | Ile | Pro | Thr | Asp | Asn | Gly | Thr | Lys | Ile | Phe | Gly | Leu | |
| 160 | | | | | 165 | | | | | 170 | | | | | 175 | |
| GAG | TGG | AAT | GAT | GAC | TAT | GTT | ACA | GCC | TAT | ATT | AGT | GAT | CGT | TCT | CAC | 637 |
| Glu | Trp | Asn | Asp | Asp | Tyr | Val | Thr | Ala | Tyr | Ile | Ser | Asp | Arg | Ser | His | |
| | | | | 180 | | | | | 185 | | | | | 190 | | |
| CAT | TTG | AAC | ATC | AAT | AAT | AAT | TGG | TTT | AAC | AAT | GTG | ACA | ATC | CTA | TAC | 685 |
| His | Leu | Asn | Ile | Asn | Asn | Asn | Trp | Phe | Asn | Asn | Val | Thr | Ile | Leu | Tyr | |
| | | | 195 | | | | | 200 | | | | | 205 | | | |
| TCT | CGA | TCA | AGC | ACT | GCT | ACG | TGG | CAG | AAG | AGT | GCT | GCA | TAT | GTT | TAT | 733 |
| Ser | Arg | Ser | Ser | Thr | Ala | Thr | Trp | Gln | Lys | Ser | Ala | Ala | Tyr | Val | Tyr | |
| | | 210 | | | | | 215 | | | | | 220 | | | | |
| CAA | GGT | GTT | TCA | AAT | TTT | ACT | TAT | TAC | AAG | TTA | AAT | AAC | ACC | AAT | GGC | 781 |
| Gln | Gly | Val | Ser | Asn | Phe | Thr | Tyr | Tyr | Lys | Leu | Asn | Asn | Thr | Asn | Gly | |
| | 225 | | | | | 230 | | | | | 235 | | | | | |
| TTG | AAA | AGC | TAT | GAA | TTG | TGT | GAA | GAT | TAT | GAA | TAC | TGC | ACT | GGC | TAT | 829 |
| Leu | Lys | Ser | Tyr | Glu | Leu | Cys | Glu | Asp | Tyr | Glu | Tyr | Cys | Thr | Gly | Tyr | |
| 240 | | | | | 245 | | | | | 250 | | | | | 255 | |
| GCT | ACC | AAC | GTA | TTT | GCC | CCG | ACA | GTG | GGC | GGT | TAT | ATA | CCT | GAT | GGC | 877 |
| Ala | Thr | Asn | Val | Phe | Ala | Pro | Thr | Val | Gly | Gly | Tyr | Ile | Pro | Asp | Gly | |
| | | | | 260 | | | | | 265 | | | | | 270 | | |
| TTC | AGT | TTT | AAC | AAT | TGG | TTT | ATG | CTT | ACA | AAC | AGT | TCC | ACG | TTT | GTT | 925 |
| Phe | Ser | Phe | Asn | Asn | Trp | Phe | Met | Leu | Thr | Asn | Ser | Ser | Thr | Phe | Val | |
| | | | 275 | | | | | 280 | | | | | 285 | | | |
| AGT | GGC | AGA | TTT | GTA | ACA | AAT | CAA | CCA | TTA | TTG | GTT | AAT | TGT | TTG | TGG | 973 |
| Ser | Gly | Arg | Phe | Val | Thr | Asn | Gln | Pro | Leu | Leu | Val | Asn | Cys | Leu | Trp | |
| | | 290 | | | | | 295 | | | | | 300 | | | | |
| CCA | GTG | CCC | AGT | TTT | GGT | GTC | GCA | GCA | CAA | GAA | TTT | TGT | TTT | GAA | GGT | 1021 |
| Pro | Val | Pro | Ser | Phe | Gly | Val | Ala | Ala | Gln | Glu | Phe | Cys | Phe | Glu | Gly | |
| | 305 | | | | | 310 | | | | | 315 | | | | | |
| GCG | CAG | TTT | AGC | CAA | TGT | AAT | GGT | GTG | TCT | TTA | AAC | AAT | ACA | GTG | GAT | 1069 |
| Ala | Gln | Phe | Ser | Gln | Cys | Asn | Gly | Val | Ser | Leu | Asn | Asn | Thr | Val | Asp | |
| 320 | | | | | 325 | | | | | 330 | | | | | 335 | |
| GTC | ATT | AGA | TTC | AAC | CTT | AAT | TTT | ACC | ACA | GAT | GTA | CAA | TCT | GGC | ATG | 1117 |
| Val | Ile | Arg | Phe | Asn | Leu | Asn | Phe | Thr | Thr | Asp | Val | Gln | Ser | Gly | Met | |
| | | | | 340 | | | | | 345 | | | | | 350 | | |
| GGT | GCT | ATA | GTA | TTT | TCA | CTG | AAT | ACA | ACA | GGT | GGT | GTC | ATT | CTT | GAG | 1165 |
| Gly | Ala | Ile | Val | Phe | Ser | Leu | Asn | Thr | Thr | Gly | Gly | Val | Ile | Leu | Glu | |
| | | | 355 | | | | | 360 | | | | | 365 | | | |
| ATT | TCT | TGT | TAT | AAT | GAT | ACA | GTG | AGT | GAG | TCA | AGT | TTC | TAC | AGT | TAT | 1213 |
| Ile | Ser | Cys | Tyr | Asn | Asp | Thr | Val | Ser | Glu | Ser | Ser | Phe | Tyr | Ser | Tyr | |
| | | 370 | | | | | 375 | | | | | 380 | | | | |
| GGT | GAA | ATT | TCA | ATC | GGC | GTA | ACT | GAT | GGA | CCG | CGT | TAC | TGT | TAC | GCC | 1261 |
| Gly | Glu | Ile | Ser | Ile | Gly | Val | Thr | Asp | Gly | Pro | Arg | Tyr | Cys | Tyr | Ala | |
| | 385 | | | | | 390 | | | | | 395 | | | | | |
| CTC | TAT | AAT | GGC | CAG | GCT | CTT | AAG | TGT | TTA | GGA | ACA | TTA | CCA | CCT | AGT | 1309 |
| Leu | Tyr | Asn | Gly | Gln | Ala | Leu | Lys | Cys | Leu | Gly | Thr | Leu | Pro | Pro | Ser | |
| 400 | | | | | 405 | | | | | 410 | | | | | 415 | |
| GTC | AAG | GAA | ATT | GCT | ATT | AGT | AAG | TGG | GGC | CAT | TTT | TAT | ATT | AAT | GGT | 1357 |
| Val | Lys | Glu | Ile | Ala | Ile | Ser | Lys | Trp | Gly | His | Phe | Tyr | Ile | Asn | Gly | |
| | | | | 420 | | | | | 425 | | | | | 430 | | |

| | | | | | | | | | | | | | | | | |
|---|---|---|---|---|---|---|---|---|---|---|---|---|---|---|---|---|
| TAC | AAT | TTC | TTT | AGC | ACT | TTT | CCT | ATT | GAT | TGT | ATA | TCT | TTT | AAT | TTA | 1405 |
| Tyr | Asn | Phe | Phe 435 | Ser | Thr | Phe | Pro | Ile 440 | Asp | Cys | Ile | Ser | Phe 445 | Asn | Leu | |
| ACC | ACT | GGT | GAT | AGT | GGA | GCA | TTT | TGG | ACA | ATT | GCT | TAC | ACA | TCG | TAC | 1453 |
| Thr | Thr | Gly 450 | Asp | Ser | Gly | Ala | Phe | Trp 455 | Thr | Ile | Ala | Tyr | Thr 460 | Ser | Tyr | |
| ACT | GAC | GCA | TTA | GTA | CAA | GTT | GAA | AAC | ACA | GCT | ATT | AAA | AAG | GTG | ACG | 1501 |
| Thr | Asp 465 | Ala | Leu | Val | Gln | Val 470 | Glu | Asn | Thr | Ala | Ile 475 | Lys | Lys | Val | Thr | |
| TAT | TGT | AAC | AGT | CAC | ATT | AAT | AAC | ATT | AAA | TGT | TCT | CAA | CTT | ACT | GCT | 1549 |
| Tyr 480 | Cys | Asn | Ser | His | Ile 485 | Asn | Asn | Ile | Lys | Cys 490 | Ser | Gln | Leu | Thr | Ala 495 | |
| AAT | TTG | CAA | AAT | GGA | TTT | TAT | CCT | GTT | GCT | TCA | AGT | GAA | GTT | GGT | CTT | 1597 |
| Asn | Leu | Gln | Asn | Gly 500 | Phe | Tyr | Pro | Val | Ala 505 | Ser | Ser | Glu | Val | Gly 510 | Leu | |
| GTC | AAT | AAG | AGT | GTT | GTG | TTA | CTA | CCT | AGT | TTC | TAT | TCA | CAT | ACC | AGT | 1645 |
| Val | Asn | Lys | Ser 515 | Val | Val | Leu | Leu | Pro 520 | Ser | Phe | Tyr | Ser | His 525 | Thr | Ser | |
| GTT | AAT | ATA | ACT | ATT | GAT | CTT | GGT | ATG | AAG | CGT | AGT | GTT | ATG | GTC | ACC | 1693 |
| Val | Asn | Ile | Thr 530 | Ile | Asp | Leu | Gly | Met 535 | Lys | Arg | Ser | Val | Met 540 | Val | Thr | |
| ATA | GCC | TCA | ACA | TTA | AGT | AAC | ATC | ACA | CTA | CCA | ATG | CAG | GAT | AAT | AAC | 1741 |
| Ile | Ala 545 | Ser | Thr | Leu | Ser | Asn 550 | Ile | Thr | Leu | Pro | Met 555 | Gln | Asp | Asn | Asn | |
| ACC | GAT | GTG | TAC | TGC | ATT | CGT | TCT | AAC | CAA | TTT | TCA | GTT | TAC | GTT | CAT | 1789 |
| Thr 560 | Asp | Val | Tyr | Cys | Ile 565 | Arg | Ser | Asn | Gln | Phe 570 | Ser | Val | Tyr | Val | His 575 | |
| TCC | ACT | TGT | AAA | AGT | TCT | TTA | TGG | GAC | GAT | GTG | TTT | AAT | TCC | GAC | TGC | 1837 |
| Ser | Thr | Cys | Lys | Ser 580 | Ser | Leu | Trp | Asp | Asp 585 | Val | Phe | Asn | Ser | Asp 590 | Cys | |
| ACA | GAT | GTT | TTA | TAT | GCT | ACA | GCT | GTT | ATA | AAA | ACT | GGT | ACT | TGT | CCT | 1885 |
| Thr | Asp | Val | Leu 595 | Tyr | Ala | Thr | Ala | Val 600 | Ile | Lys | Thr | Gly | Thr 605 | Cys | Pro | |
| TTC | TCG | TTT | GAT | AAA | TTG | AAC | AAT | TAC | TTA | ACT | TTT | AAC | AAG | TTC | TGT | 1933 |
| Phe | Ser | Phe 610 | Asp | Lys | Leu | Asn | Asn 615 | Tyr | Leu | Thr | Phe | Asn 620 | Lys | Phe | Cys | |
| TTG | TCA | TTG | AAT | CCT | GTT | GGT | GCC | AAC | TGC | AAG | TTT | GAT | GTT | GCC | GCT | 1981 |
| Leu | Ser 625 | Leu | Asn | Pro | Val | Gly 630 | Ala | Asn | Cys | Lys | Phe 635 | Asp | Val | Ala | Ala | |
| CGT | ACA | AGA | ACC | AAT | GAG | CAG | GTT | GTT | AGA | AGT | TTA | TAT | GTA | ATA | TAT | 2029 |
| Arg 640 | Thr | Arg | Thr | Asn | Glu 645 | Gln | Val | Val | Arg | Ser 650 | Leu | Tyr | Val | Ile | Tyr 655 | |
| GAA | GAA | GGA | GAC | AAC | ATA | GCG | GGT | GTG | CCG | TCT | GAC | AAT | AGT | GGT | CTT | 2077 |
| Glu | Glu | Gly | Asp | Asn 660 | Ile | Ala | Gly | Val | Pro 665 | Ser | Asp | Asn | Ser | Gly 670 | Leu | |
| CAC | GAC | TTG | TCA | GTG | CTA | CAC | TTA | GAC | TCC | TGT | ACA | GAT | TAT | AAT | ATA | 2125 |
| His | Asp | Leu | Ser 675 | Val | Leu | His | Leu | Asp 680 | Ser | Cys | Thr | Asp | Tyr 685 | Asn | Ile | |
| TAT | GGT | AGA | ACT | GGT | GTT | GGT | ATT | ATT | AGA | CAA | ACT | AAC | AGT | ACG | CTA | 2173 |
| Tyr | Gly | Arg 690 | Thr | Gly | Val | Gly | Ile 695 | Ile | Arg | Gln | Thr | Asn 700 | Ser | Thr | Leu | |
| CTT | AGT | GGC | TTA | TAT | TAC | ACA | TCA | CTA | TCA | GGT | GAC | TTG | TTA | GGG | TTT | 2221 |
| Leu | Ser 705 | Gly | Leu | Tyr | Tyr | Thr 710 | Ser | Leu | Ser | Gly | Asp 715 | Leu | Leu | Gly | Phe | |
| AAA | AAT | GTT | AGT | GAT | GGT | GTC | ATC | TAT | TCT | GTC | ACG | CCA | TGT | GAT | GTA | 2269 |
| Lys | Asn | Val 720 | Ser | Asp | Gly | Val | Ile 725 | Tyr | Ser | Val | Thr | Pro 730 | Cys | Asp | Val 735 | |
| AGC | GTA | CAA | GCT | GCT | GTT | ATT | GAT | GGC | GCC | ATA | GTT | GGA | GCT | ATG | ACT | 2317 |
| Ser | Val | Gln | Ala | Ala 740 | Val | Ile | Asp | Gly | Ala 745 | Ile | Val | Gly | Ala | Met 750 | Thr | |

| | | | | | | | | | | | | | | | | |
|---|---|---|---|---|---|---|---|---|---|---|---|---|---|---|---|---|
| TCC | ATT | AAT | AGT | GAA | CTG | TTA | GGT | CTA | ACA | CAT | TGG | ACA | ACA | ACA | CCT | 2365 |
| Ser | Ile | Asn | Ser 755 | Glu | Leu | Leu | Gly | Leu 760 | Thr | His | Trp | Thr | Thr 765 | Thr | Pro | |
| AAT | TTT | TAT | TAT | TAT | TCT | ATA | TAT | AAT | TAT | ACC | AAT | GAA | AGG | ACT | CGT | 2413 |
| Asn | Phe | Tyr 770 | Tyr | Tyr | Ser | Ile | Tyr 775 | Asn | Tyr | Thr | Asn | Glu 780 | Arg | Thr | Arg | |
| GGC | ACA | GCA | ATT | GAT | AGT | AAC | GAT | GTT | GAT | TGT | GAA | CCT | ATC | ATA | ACC | 2461 |
| Gly | Thr 785 | Ala | Ile | Asp | Ser | Asn 790 | Asp | Val | Asp | Cys | Glu 795 | Pro | Ile | Ile | Thr | |
| TAT | TCT | AAT | ATA | GGT | GTT | TGT | AAA | AAT | GGA | GCT | TTG | GTT | TTT | ATT | AAC | 2509 |
| Tyr 800 | Ser | Asn | Ile | Gly | Val 805 | Cys | Lys | Asn | Gly | Ala 810 | Leu | Val | Phe | Ile | Asn 815 | |
| GTC | ACA | CAT | TCT | GAT | GGA | GAC | GTT | CAA | CCA | ATT | AGC | ACC | GGT | AAT | GTC | 2557 |
| Val | Thr | His | Ser | Asp 820 | Gly | Asp | Val | Gln | Pro 825 | Ile | Ser | Thr | Gly | Asn 830 | Val | |
| ACG | ATA | CCT | ACA | AAT | TTT | ACC | ATA | TCT | GTG | CAA | GTT | GAA | TAC | ATT | CAG | 2605 |
| Thr | Ile | Pro | Thr 835 | Asn | Phe | Thr | Ile | Ser 840 | Val | Gln | Val | Glu | Tyr 845 | Ile | Gln | |
| GTT | TAC | ACT | ACA | CCG | GTG | TCA | ATA | GAT | TGT | TCA | AGG | TAC | GTT | TGC | AAT | 2653 |
| Val | Tyr | Thr 850 | Thr | Pro | Val | Ser | Ile 855 | Asp | Cys | Ser | Arg | Tyr 860 | Val | Cys | Asn | |
| GGT | AAC | CCT | AGA | TGC | AAT | AAA | TTG | TTA | ACG | CAA | TAC | GTT | TCT | GCA | TGT | 2701 |
| Gly | Asn 865 | Pro | Arg | Cys | Asn | Lys 870 | Leu | Leu | Thr | Gln | Tyr 875 | Val | Ser | Ala | Cys | |
| CAA | ACT | ATT | GAG | CAA | GCA | CTT | GCA | ATG | GGT | GCC | AGA | CTT | GAA | AAC | ATG | 2749 |
| Gln 880 | Thr | Ile | Glu | Gln | Ala 885 | Leu | Ala | Met | Gly | Ala 890 | Arg | Leu | Glu | Asn | Met 895 | |
| GAG | ATT | GAT | TCC | ATG | TTG | TTT | GTT | TCG | GAA | AAT | GCC | CTT | AAA | TTG | GCA | 2797 |
| Glu | Ile | Asp | Ser | Met 900 | Leu | Phe | Val | Ser | Glu 905 | Asn | Ala | Leu | Lys | Leu 910 | Ala | |
| TCT | GTT | GAA | GCA | TTA | ATA | GTA | GGA | AAT | TTA | GAT | CCT | ATT | TAC | AAA | GAA | 2845 |
| Ser | Val | Glu | Ala 915 | Leu | Ile | Val | Gly | Asn 920 | Leu | Asp | Pro | Ile | Tyr 925 | Lys | Glu | |
| TGG | CCT | AAC | ATT | GGT | GGT | TCT | TGG | CTA | GGA | GGT | TTA | AAA | GAC | ATA | TTG | 2893 |
| Trp | Pro | Asn 930 | Ile | Gly | Gly | Ser | Trp 935 | Leu | Gly | Gly | Leu | Lys 940 | Asp | Ile | Leu | |
| CCA | TCT | CAC | AAC | AGC | AAA | CGT | AAG | TAC | CGG | TCG | GCT | ATA | GAA | GAT | TTG | 2941 |
| Pro | Ser | His 945 | Asn | Ser | Lys | Arg | Lys 950 | Tyr | Arg | Ser | Ala | Ile 955 | Glu | Asp | Leu | |
| CTT | TTT | GAT | AAG | GTT | GTA | ACA | TCT | GGC | TTA | GGT | ACA | GTT | GAT | GAA | GAT | 2989 |
| Leu 960 | Phe | Asp | Lys | Val | Val 965 | Thr | Ser | Gly | Leu | Gly 970 | Thr | Val | Asp | Glu | Asp 975 | |
| TAT | AAA | CGT | TGT | ACA | GGT | GGT | TAT | GAC | ATA | GCT | GAC | TTA | GTG | TGT | GCA | 3037 |
| Tyr | Lys | Arg | Cys | Thr 980 | Gly | Gly | Tyr | Asp | Ile 985 | Ala | Asp | Leu | Val | Cys 990 | Ala | |
| CAA | TAT | TAC | AAT | GGC | ATC | ATG | GTG | CTA | CCT | GGT | GTA | GCT | AAT | GAT | GAC | 3085 |
| Gln | Tyr | Tyr | Asn 995 | Gly | Ile | Met | Val | Leu 1000 | Pro | Gly | Val | Ala | Asn 1005 | Asp | Asp | |
| AAG | ATG | GCT | ATG | TAC | ACT | GCA | TCT | CTT | GCA | GGT | GGT | ATA | ACA | TTA | GGT | 3133 |
| Lys | Met | Ala | Met 1010 | Tyr | Thr | Ala | Ser | Leu 1015 | Ala | Gly | Gly | Ile | Thr 1020 | Leu | Gly | |
| GCA | CTT | GGT | GGT | GGC | GCA | GTG | TCT | ATA | CCT | TTT | GCA | ATA | GCA | GTT | CAA | 3181 |
| Ala | Leu | Gly 1025 | Gly | Gly | Ala | Val | Ser 1030 | Ile | Pro | Phe | Ala | Ile 1035 | Ala | Val | Gln | |
| GCC | AGA | CTT | AAT | TAT | GTT | GCT | CTA | CAA | ACT | GAT | GTA | TTG | AAC | AAG | AAC | 3229 |
| Ala | Arg 1040 | Leu | Asn | Tyr | Val | Ala 1045 | Leu | Gln | Thr | Asp | Val 1050 | Leu | Asn | Lys | Asn 1055 | |
| CAG | CAG | ATC | CTG | GCT | AAT | GCT | TTC | AAT | CAA | GCT | ATT | GGT | AAC | ATT | ACA | 3277 |
| Gln | Gln | Ile | Leu | Ala 1060 | Asn | Ala | Phe | Asn | Gln 1065 | Ala | Ile | Gly | Asn | Ile 1070 | Thr | |

-continued

| | |
|---|---|
| CAG GCA TTT GGT AAG GTT AAT GAT GCT ATA CAT CAA ACG TCA CAA GGT<br>Gln Ala Phe Gly Lys Val Asn Asp Ala Ile His Gln Thr Ser Gln Gly<br>              1075                       1080                     1085 | 3325 |
| CTT GCT ACT GTT GCT AAA GCA TTG GCA AAA GTG CAA GAT GTT GTT AAC<br>Leu Ala Thr Val Ala Lys Ala Leu Ala Lys Val Gln Asp Val Val Asn<br>        1090                     1095                     1100 | 3373 |
| ACA CAA GGG CAA GCT TTA AGC CAC CTA ACA GTA CAA TTG CAA AAT AAT<br>Thr Gln Gly Gln Ala Leu Ser His Leu Thr Val Gln Leu Gln Asn Asn<br>1105                     1110                     1115 | 3421 |
| TTC CAA GCC ATT AGT AGT TCC ATT AGT GAC ATT TAT AAC AGG CTT GAT<br>Phe Gln Ala Ile Ser Ser Ser Ile Ser Asp Ile Tyr Asn Arg Leu Asp<br>1120                     1125                     1130                     1135 | 3469 |
| GAA TTG AGT GCT GAT GCA CAA GTT GAC AGG CTG ATT ACA GGA AGA CTT<br>Glu Leu Ser Ala Asp Ala Gln Val Asp Arg Leu Ile Thr Gly Arg Leu<br>              1140                       1145                     1150 | 3517 |
| ACA GCA CTT AAT GCA TTT GTG TCT CAG ACT TTA ACC AGA CAA GCA GAG<br>Thr Ala Leu Asn Ala Phe Val Ser Gln Thr Leu Thr Arg Gln Ala Glu<br>                     1155                     1160                     1165 | 3565 |
| GTT AGG GCT AGC AGA CAG CTT GCT AAA GAC AAG GTA AAT GAA TGC GTT<br>Val Arg Ala Ser Arg Gln Leu Ala Lys Asp Lys Val Asn Glu Cys Val<br>        1170                     1175                     1180 | 3613 |
| AGG TCT CAA TCT CAG AGA TTT GGA TTC TGT GGT AAT GGT ACA CAT TTA<br>Arg Ser Gln Ser Gln Arg Phe Gly Phe Cys Gly Asn Gly Thr His Leu<br>1185                     1190                     1195 | 3661 |
| TTT TCA CTT GCA AAT GCA GCA CCA AAT GGC ATG ATC TTC TTT CAC ACA<br>Phe Ser Leu Ala Asn Ala Ala Pro Asn Gly Met Ile Phe Phe His Thr<br>1200                     1205                     1210                     1215 | 3709 |
| GTG CTA TTA CCA ACA GCT TAT GAA ACC GTG ACA GCC TGG TCA GGT ATT<br>Val Leu Leu Pro Thr Ala Tyr Glu Thr Val Thr Ala Trp Ser Gly Ile<br>                     1220                     1225                     1230 | 3757 |
| TGT GCA TCA GAT GGC GAT CGT ACT TTT GGA CTT GTT GTT AAG GAT GTC<br>Cys Ala Ser Asp Gly Asp Arg Thr Phe Gly Leu Val Val Lys Asp Val<br>            1235                     1240                     1245 | 3805 |
| CAG TTG ACG CTG TTT CGC AAT CTA GAT GAC AAA TTC TAT TTG ACT CCC<br>Gln Leu Thr Leu Phe Arg Asn Leu Asp Asp Lys Phe Tyr Leu Thr Pro<br>        1250                     1255                     1260 | 3853 |
| AGA ACT ATG TAT CAG CCT AGA GTT GCA ACT AGT TCT GAT TTT GTT CAA<br>Arg Thr Met Tyr Gln Pro Arg Val Ala Thr Ser Ser Asp Phe Val Gln<br>1265                     1270                     1275 | 3901 |
| ATT GAA GGA TGT GAT GTG TTG TTT GTT AAT GCA ACT GTA ATT GAC TTG<br>Ile Glu Gly Cys Asp Val Leu Phe Val Asn Ala Thr Val Ile Asp Leu<br>1280                     1285                     1290                     1295 | 3949 |
| CCT AGT ATT ATA CCT GAC TAT ATT GAT ATT AAT CAA ACT GTT CAG GAC<br>Pro Ser Ile Ile Pro Asp Tyr Ile Asp Ile Asn Gln Thr Val Gln Asp<br>                     1300                     1305                     1310 | 3997 |
| ATA TTA GAA AAT TTC AGA CCA AAT TGG ACT GTA CCT GAG TTG CCA CTT<br>Ile Leu Glu Asn Phe Arg Pro Asn Trp Thr Val Pro Glu Leu Pro Leu<br>            1315                     1320                     1325 | 4045 |
| GAC ATT TTC AAT GCA ACC TAC TTA AAC CTG ACT GGT GAA ATT AAG TGC<br>Asp Ile Phe Asn Ala Thr Tyr Leu Asn Leu Thr Gly Glu Ile Lys Cys<br>        1330                     1335                     1340 | 4093 |
| TTA GAA TTT AGG TCA GAA AAG TTA CAT AAC ACC ACA GTA GAA CTT GCT<br>Leu Glu Phe Arg Ser Glu Lys Leu His Asn Thr Thr Val Glu Leu Ala<br>1345                     1350                     1355 | 4141 |
| ATT CTC ATT GAT AAT ATT AAT AAC ACA TTA TCA ATC TTA ATG CTC AAT<br>Ile Leu Ile Asp Asn Ile Asn Asn Thr Leu Ser Ile Leu Met Leu Asn<br>1360                     1365                     1370                     1375 | 4189 |
| AGA ATT GAA ACT TAT GTA AAA TGG CCT TGG TAT GTG TGG CTA CTA ATT<br>Arg Ile Glu Thr Tyr Val Lys Trp Pro Trp Tyr Val Trp Leu Leu Ile<br>            1380                     1385                     1390 | 4237 |

```
GGA TTA GTA GTA ATA TTC TGC ATA CCC ATA TTG CTA TTT TGT TGT TGT        4285
Gly Leu Val Val Ile Phe Cys Ile Pro Ile Leu Leu Phe Cys Cys Cys
            1395                1400                1405

AGT ACT GGT TGT TGT GGA TGT ATT GGG TGT TTA GGA AGC TGT TGT CAT        4333
Ser Thr Gly Cys Cys Gly Cys Ile Gly Cys Leu Gly Ser Cys Cys His
        1410                1415                1420

TCC ATA TGT AGT AGA AGG CAA TTT GAA AGT TAT GAA CCA ATT GAA AAA        4381
Ser Ile Cys Ser Arg Arg Gln Phe Glu Ser Tyr Glu Pro Ile Glu Lys
    1425                1430                1435

GTT CAT GTT CAC TGAATTCAAA ATGTTAAGTC TACTATTTTA ATTACACCCG            4433
Val His Val His
1440

TGGCCACACA AGTTATATAA TGGTGCTGTC GTAAGTTCGA TACCAGTCAA CTATTAGCAT      4493

TAATAAA                                                                4500
```

( 2 ) INFORMATION FOR SEQ ID NO:2:

( i ) SEQUENCE CHARACTERISTICS:
        ( A ) LENGTH: 1443 amino acids
        ( B ) TYPE: amino acid
        ( C ) STRANDEDNESS: single
        ( D ) TOPOLOGY: linear ( i i ) MOLECULE TYPE: protein ( v i ) ORIGINAL SOURCE:
        ( A ) ORGANISM: Canina corona virus
        ( B ) STRAIN: CCV-6

( i x ) FEATURE:
        ( A ) NAME/KEY: Protein
        ( B ) LOCATION: 1..1443
        ( D ) OTHER INFORMATION: /label=CCV6_Spike ( x i ) SEQUENCE DESCRIPTION: SEQ ID NO:2:

```
Met Ile Val Leu Ile Leu Cys Leu Leu Leu Phe Ser Tyr Asn Ser Val
1               5                   10                  15

Ile Cys Thr Ser Asn Asn Asp Cys Val Gln Val Asn Val Thr Gln Leu
            20                  25                  30

Pro Gly Asn Glu Asn Ile Ile Lys Asp Phe Leu Phe His Thr Phe Lys
        35                  40                  45

Glu Glu Gly Ser Val Val Val Gly Gly Tyr Tyr Pro Thr Glu Val Trp
50                  55                  60

Tyr Asn Cys Ser Arg Ser Ala Thr Thr Ala Tyr Lys Asp Phe Ser
65                  70                  75                  80

Asn Ile His Ala Phe Tyr Phe Asp Met Glu Asp Met Glu Lys Ser Thr
            85                  90                  95

Gly Asn Ala Arg Gly Lys Pro Leu Leu Val His Val His Gly Gly Pro
        100                 105                 110

Val Ser Ile Ile Ile Ile Cys Ala Arg Lys Ala Ser Leu Lys His Gly
            115                 120                 125

Leu Leu Cys Ile Thr Lys Asn Lys Ile Ile Asp Tyr Asn Thr Phe Thr
        130                 135                 140

Ser Ala Gln Trp Ser Ala Ile Cys Leu Gly Asp Asp Arg Lys Ile Pro
145                 150                 155                 160

Phe Ser Val Ile Pro Thr Asp Asn Gly Thr Lys Ile Phe Gly Leu Glu
                165                 170                 175

Trp Asn Asp Asp Tyr Val Thr Ala Tyr Ile Ser Asp Arg Ser His His
            180                 185                 190

Leu Asn Ile Asn Asn Asn Trp Phe Asn Asn Val Thr Ile Leu Tyr Ser
        195                 200                 205
```

```
Arg  Ser  Ser  Thr  Ala  Thr  Trp  Gln  Lys  Ser  Ala  Ala  Tyr  Val  Tyr  Gln
     210                      215                 220

Gly  Val  Ser  Asn  Phe  Thr  Tyr  Tyr  Lys  Leu  Asn  Asn  Thr  Asn  Gly  Leu
225                      230                      235                      240

Lys  Ser  Tyr  Glu  Leu  Cys  Glu  Asp  Tyr  Glu  Tyr  Cys  Thr  Gly  Tyr  Ala
                    245                      250                      255

Thr  Asn  Val  Phe  Ala  Pro  Thr  Val  Gly  Gly  Tyr  Ile  Pro  Asp  Gly  Phe
               260                      265                      270

Ser  Phe  Asn  Asn  Trp  Phe  Met  Leu  Thr  Asn  Ser  Ser  Thr  Phe  Val  Ser
          275                      280                      285

Gly  Arg  Phe  Val  Thr  Asn  Gln  Pro  Leu  Leu  Val  Asn  Cys  Leu  Trp  Pro
     290                      295                      300

Val  Pro  Ser  Phe  Gly  Val  Ala  Ala  Gln  Glu  Phe  Cys  Phe  Glu  Gly  Ala
305                      310                      315                      320

Gln  Phe  Ser  Gln  Cys  Asn  Gly  Val  Ser  Leu  Asn  Asn  Thr  Val  Asp  Val
               325                      330                      335

Ile  Arg  Phe  Asn  Leu  Asn  Phe  Thr  Thr  Asp  Val  Gln  Ser  Gly  Met  Gly
          340                      345                      350

Ala  Ile  Val  Phe  Ser  Leu  Asn  Thr  Thr  Gly  Gly  Val  Ile  Leu  Glu  Ile
          355                      360                      365

Ser  Cys  Tyr  Asn  Asp  Thr  Val  Ser  Glu  Ser  Ser  Phe  Tyr  Ser  Tyr  Gly
     370                      375                      380

Glu  Ile  Ser  Ile  Gly  Val  Thr  Asp  Gly  Pro  Arg  Tyr  Cys  Tyr  Ala  Leu
385                      390                      395                      400

Tyr  Asn  Gly  Gln  Ala  Leu  Lys  Cys  Leu  Gly  Thr  Leu  Pro  Pro  Ser  Val
                    405                      410                      415

Lys  Glu  Ile  Ala  Ile  Ser  Lys  Trp  Gly  His  Phe  Tyr  Ile  Asn  Gly  Tyr
               420                      425                      430

Asn  Phe  Phe  Ser  Thr  Phe  Pro  Ile  Asp  Cys  Ile  Ser  Phe  Asn  Leu  Thr
          435                      440                      445

Thr  Gly  Asp  Ser  Gly  Ala  Phe  Trp  Thr  Ile  Ala  Tyr  Thr  Ser  Tyr  Thr
     450                      455                      460

Asp  Ala  Leu  Val  Gln  Val  Glu  Asn  Thr  Ala  Ile  Lys  Lys  Val  Thr  Tyr
465                      470                      475                      480

Cys  Asn  Ser  His  Ile  Asn  Asn  Ile  Lys  Cys  Ser  Gln  Leu  Thr  Ala  Asn
               485                      490                      495

Leu  Gln  Asn  Gly  Phe  Tyr  Pro  Val  Ala  Ser  Ser  Glu  Val  Gly  Leu  Val
               500                      505                      510

Asn  Lys  Ser  Val  Val  Leu  Leu  Pro  Ser  Phe  Tyr  Ser  His  Thr  Ser  Val
          515                      520                      525

Asn  Ile  Thr  Ile  Asp  Leu  Gly  Met  Lys  Arg  Ser  Val  Met  Val  Thr  Ile
530                      535                      540

Ala  Ser  Thr  Leu  Ser  Asn  Ile  Thr  Leu  Pro  Met  Gln  Asp  Asn  Asn  Thr
545                      550                      555                      560

Asp  Val  Tyr  Cys  Ile  Arg  Ser  Asn  Gln  Phe  Ser  Val  Tyr  Val  His  Ser
               565                      570                      575

Thr  Cys  Lys  Ser  Ser  Leu  Trp  Asp  Asp  Val  Phe  Asn  Ser  Asp  Cys  Thr
               580                      585                      590

Asp  Val  Leu  Tyr  Ala  Thr  Ala  Val  Ile  Lys  Thr  Gly  Thr  Cys  Pro  Phe
          595                      600                      605

Ser  Phe  Asp  Lys  Leu  Asn  Asn  Tyr  Leu  Thr  Phe  Asn  Lys  Phe  Cys  Leu
     610                      615                      620

Ser  Leu  Asn  Pro  Val  Gly  Ala  Asn  Cys  Lys  Phe  Asp  Val  Ala  Ala  Arg
```

|     |     |     |     |
| --- | --- | --- | --- |
| 625 | 630 | 635 | 640 |

Thr Arg Thr Asn Glu Gln Val Val Arg Ser Leu Tyr Val Ile Tyr Glu
                645                 650                 655

Glu Gly Asp Asn Ile Ala Gly Val Pro Ser Asp Asn Ser Gly Leu His
                660                 665                 670

Asp Leu Ser Val Leu His Leu Asp Ser Cys Thr Asp Tyr Asn Ile Tyr
            675                 680                 685

Gly Arg Thr Gly Val Gly Ile Ile Arg Gln Thr Asn Ser Thr Leu Leu
        690                 695                 700

Ser Gly Leu Tyr Tyr Thr Ser Leu Ser Gly Asp Leu Leu Gly Phe Lys
705                 710                 715                 720

Asn Val Ser Asp Gly Val Ile Tyr Ser Val Thr Pro Cys Asp Val Ser
            725                 730                 735

Val Gln Ala Ala Val Ile Asp Gly Ala Ile Val Gly Ala Met Thr Ser
                740                 745                 750

Ile Asn Ser Glu Leu Leu Gly Leu Thr His Trp Thr Thr Thr Pro Asn
            755                 760                 765

Phe Tyr Tyr Tyr Ser Ile Tyr Asn Tyr Thr Asn Glu Arg Thr Arg Gly
        770                 775                 780

Thr Ala Ile Asp Ser Asn Asp Val Asp Cys Glu Pro Ile Ile Thr Tyr
785                 790                 795                 800

Ser Asn Ile Gly Val Cys Lys Asn Gly Ala Leu Val Phe Ile Asn Val
                805                 810                 815

Thr His Ser Asp Gly Asp Val Gln Pro Ile Ser Thr Gly Asn Val Thr
            820                 825                 830

Ile Pro Thr Asn Phe Thr Ile Ser Val Gln Val Glu Tyr Ile Gln Val
        835                 840                 845

Tyr Thr Thr Pro Val Ser Ile Asp Cys Ser Arg Tyr Val Cys Asn Gly
850                 855                 860

Asn Pro Arg Cys Asn Lys Leu Leu Thr Gln Tyr Val Ser Ala Cys Gln
865                 870                 875                 880

Thr Ile Glu Gln Ala Leu Ala Met Gly Ala Arg Leu Glu Asn Met Glu
            885                 890                 895

Ile Asp Ser Met Leu Phe Val Ser Glu Asn Ala Leu Lys Leu Ala Ser
        900                 905                 910

Val Glu Ala Leu Ile Val Gly Asn Leu Asp Pro Ile Tyr Lys Glu Trp
        915                 920                 925

Pro Asn Ile Gly Gly Ser Trp Leu Gly Gly Leu Lys Asp Ile Leu Pro
    930                 935                 940

Ser His Asn Ser Lys Arg Lys Tyr Arg Ser Ala Ile Glu Asp Leu Leu
945                 950                 955                 960

Phe Asp Lys Val Val Thr Ser Gly Leu Gly Thr Val Asp Glu Asp Tyr
            965                 970                 975

Lys Arg Cys Thr Gly Gly Tyr Asp Ile Ala Asp Leu Val Cys Ala Gln
            980                 985                 990

Tyr Tyr Asn Gly Ile Met Val Leu Pro Gly Val Ala Asn Asp Asp Lys
        995                 1000                1005

Met Ala Met Tyr Thr Ala Ser Leu Ala Gly Gly Ile Thr Leu Gly Ala
    1010                1015                1020

Leu Gly Gly Gly Ala Val Ser Ile Pro Phe Ala Ile Ala Val Gln Ala
1025                1030                1035                1040

Arg Leu Asn Tyr Val Ala Leu Gln Thr Asp Val Leu Asn Lys Asn Gln
            1045                1050                1055

```
Gln Ile Leu Ala Asn Ala Phe Asn Gln Ala Ile Gly Asn Ile Thr Gln
                1060                1065                1070

Ala Phe Gly Lys Val Asn Asp Ala Ile His Gln Thr Ser Gln Gly Leu
            1075                1080                1085

Ala Thr Val Ala Lys Ala Leu Ala Lys Val Gln Asp Val Val Asn Thr
            1090                1095                1100

Gln Gly Gln Ala Leu Ser His Leu Thr Val Gln Leu Gln Asn Asn Phe
1105                1110                1115                1120

Gln Ala Ile Ser Ser Ser Ile Ser Asp Ile Tyr Asn Arg Leu Asp Glu
                1125                1130                1135

Leu Ser Ala Asp Ala Gln Val Asp Arg Leu Ile Thr Gly Arg Leu Thr
            1140                1145                1150

Ala Leu Asn Ala Phe Val Ser Gln Thr Leu Thr Arg Gln Ala Glu Val
            1155                1160                1165

Arg Ala Ser Arg Gln Leu Ala Lys Asp Lys Val Asn Glu Cys Val Arg
            1170                1175                1180

Ser Gln Ser Gln Arg Phe Gly Phe Cys Gly Asn Gly Thr His Leu Phe
1185                1190                1195                1200

Ser Leu Ala Asn Ala Ala Pro Asn Gly Met Ile Phe Phe His Thr Val
            1205                1210                1215

Leu Leu Pro Thr Ala Tyr Glu Thr Val Thr Ala Trp Ser Gly Ile Cys
            1220                1225                1230

Ala Ser Asp Gly Asp Arg Thr Phe Gly Leu Val Val Lys Asp Val Gln
            1235                1240                1245

Leu Thr Leu Phe Arg Asn Leu Asp Asp Lys Phe Tyr Leu Thr Pro Arg
            1250                1255                1260

Thr Met Tyr Gln Pro Arg Val Ala Thr Ser Ser Asp Phe Val Gln Ile
1265                1270                1275                1280

Glu Gly Cys Asp Val Leu Phe Val Asn Ala Thr Val Ile Asp Leu Pro
            1285                1290                1295

Ser Ile Ile Pro Asp Tyr Ile Asp Ile Asn Gln Thr Val Gln Asp Ile
            1300                1305                1310

Leu Glu Asn Phe Arg Pro Asn Trp Thr Val Pro Glu Leu Pro Leu Asp
            1315                1320                1325

Ile Phe Asn Ala Thr Tyr Leu Asn Leu Thr Gly Glu Ile Lys Cys Leu
            1330                1335                1340

Glu Phe Arg Ser Glu Lys Leu His Asn Thr Thr Val Glu Leu Ala Ile
1345                1350                1355                1360

Leu Ile Asp Asn Ile Asn Asn Thr Leu Ser Ile Leu Met Leu Asn Arg
            1365                1370                1375

Ile Glu Thr Tyr Val Lys Trp Pro Trp Tyr Val Trp Leu Leu Ile Gly
            1380                1385                1390

Leu Val Val Ile Phe Cys Ile Pro Ile Leu Leu Phe Cys Cys Cys Ser
            1395                1400                1405

Thr Gly Cys Cys Gly Cys Ile Gly Cys Leu Gly Ser Cys Cys His Ser
            1410                1415                1420

Ile Cys Ser Arg Arg Gln Phe Glu Ser Tyr Glu Pro Ile Glu Lys Val
1425                1430                1435                1440

His Val His
```

( 2 ) INFORMATION FOR SEQ ID NO:3:

( i ) SEQUENCE CHARACTERISTICS:
     ( A ) LENGTH: 4429 base pairs
     ( B ) TYPE: nucleic acid (C) STRANDEDNESS: single
(D) TOPOLOGY: linear (ii) MOLECULE TYPE: cDNA (vi) ORIGINAL SOURCE:
(A) ORGANISM: Canina corona virus
(B) STRAIN: CCVInSAVC-1

(ix) FEATURE:
(A) NAME/KEY: CDS
(B) LOCATION: 60..4412
(D) OTHER INFORMATION: /label=CCVInSAVC-1_Spikegene (xi) SEQUENCE DESCRIPTION: SEQ ID NO:3:

```
TTGCTCATTA GAAACAATGG TAAACTACTA AACTTTGGTA ATCACTTGGT TAATGTGCC                 59

ATG ATT GTG CTT ACA TTG TGC CTT TTC TTG TTT TTG TAC AGT AGT GTG               107
Met Ile Val Leu Thr Leu Cys Leu Phe Leu Phe Leu Tyr Ser Ser Val
 1           5                  10                  15

AGC TGT ACA TCA AAC AAT GAC TGT GTA CAA GTT AAT GTG ACA CAA CTG               155
Ser Cys Thr Ser Asn Asn Asp Cys Val Gln Val Asn Val Thr Gln Leu
             20                  25                  30

CCT GGC AAT GAA AAT ATT ATC AAA GAT TTT CTA TTT CAG AAC TTT AAA               203
Pro Gly Asn Glu Asn Ile Ile Lys Asp Phe Leu Phe Gln Asn Phe Lys
         35                  40                  45

GAA GAA GGA AGT TTA GTT GTT GGT GGT TAT TAC CCC ACA GAG GTG TGG               251
Glu Glu Gly Ser Leu Val Val Gly Gly Tyr Tyr Pro Thr Glu Val Trp
     50                  55                  60

TAT AAC TGT TCC ACA ACT CAA CAA ACT ACC GCT TAT AAG TAT TTT AGT               299
Tyr Asn Cys Ser Thr Thr Gln Gln Thr Thr Ala Tyr Lys Tyr Phe Ser
 65                  70                  75                  80

AAT ATA CAT GCA TTT TAT TTT GAT ATG GAA GCC ATG GAG AAT AGT ACT               347
Asn Ile His Ala Phe Tyr Phe Asp Met Glu Ala Met Glu Asn Ser Thr
                 85                  90                  95

GGC AAT GCA CGT GGT AAA CCT TTA CTA GTA CAT GTT CAT GGT AAT CCT               395
Gly Asn Ala Arg Gly Lys Pro Leu Leu Val His Val His Gly Asn Pro
            100                 105                 110

GTT AGT ATC ATT GTT TAC ATA TCA GCT TAT AGA GAT GAT GTG CAA TTT               443
Val Ser Ile Ile Val Tyr Ile Ser Ala Tyr Arg Asp Asp Val Gln Phe
        115                 120                 125

AGG CCG CTT TTA AAG CAT GGT TTA TTG TGT ATA ACT AAA AAT GAC ACC               491
Arg Pro Leu Leu Lys His Gly Leu Leu Cys Ile Thr Lys Asn Asp Thr
    130                 135                 140

GTT GAC TAT AAT AGC TTT ACA ATT AAC CAA TGG CGA GAC ATA TGT TTG               539
Val Asp Tyr Asn Ser Phe Thr Ile Asn Gln Trp Arg Asp Ile Cys Leu
145                 150                 155                 160

GGT GAC GAC AGA AAA ATA CCA TTC TCT GTA GTA CCC ACA GAT AAT GGT               587
Gly Asp Asp Arg Lys Ile Pro Phe Ser Val Val Pro Thr Asp Asn Gly
                165                 170                 175

ACG AAA TTA TTT GGT CTT GAG TGG AAT GAT GAC TAT GTT ACA GCC TAT               635
Thr Lys Leu Phe Gly Leu Glu Trp Asn Asp Asp Tyr Val Thr Ala Tyr
            180                 185                 190

ATT AGT GAT GAG TCT CAC CGT TTG AAT ATC AAT AAT AAT TGG TTT AAC               683
Ile Ser Asp Glu Ser His Arg Leu Asn Ile Asn Asn Asn Trp Phe Asn
        195                 200                 205

AAT GTT ACA CTC CTA TAC TCA CGT ACA AGC ACC GCC ACG TGG CAA CAC               731
Asn Val Thr Leu Leu Tyr Ser Arg Thr Ser Thr Ala Thr Trp Gln His
210                 215                 220

AGT GCT GCA TAT GTT TAT CAA GGT GTT TCA AAT TTT ACT TAT TAC AAG               779
Ser Ala Ala Tyr Val Tyr Gln Gly Val Ser Asn Phe Thr Tyr Tyr Lys
225                 230                 235                 240

TTA AAT AAA ACC GCT GGC TTA AAA AGC TAT GAA TTG TGT GAA GAT TAT               827
Leu Asn Lys Thr Ala Gly Leu Lys Ser Tyr Glu Leu Cys Glu Asp Tyr
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     |     |     | 245 |     |     |     |     | 250 |     |     |     |     | 255 |     |      |
| GAA | TAC | TGC | ACT | GGC | TAT | GCA | ACC | AAT | GTG | TTT | GCT | CCG | ACA | TCA | GGT | 875  |
| Glu | Tyr | Cys | Thr | Gly | Tyr | Ala | Thr | Asn | Val | Phe | Ala | Pro | Thr | Ser | Gly |      |
|     |     | 260 |     |     |     |     | 265 |     |     |     |     | 270 |     |     |     |      |
| GGT | TAT | ATA | CCT | GAT | GGA | TTC | AGT | TTT | AAC | AAT | TGG | TTT | ATG | CTT | ACA | 923  |
| Gly | Tyr | Ile | Pro | Asp | Gly | Phe | Ser | Phe | Asn | Asn | Trp | Phe | Met | Leu | Thr |      |
|     |     | 275 |     |     |     |     | 280 |     |     |     |     | 285 |     |     |     |      |
| AAC | AGC | TCC | ACT | TTT | GTT | AGT | GGC | AGA | TTT | GTA | ACA | AAT | CAA | CCG | CTG | 971  |
| Asn | Ser | Ser | Thr | Phe | Val | Ser | Gly | Arg | Phe | Val | Thr | Asn | Gln | Pro | Leu |      |
|     | 290 |     |     |     |     | 295 |     |     |     |     | 300 |     |     |     |     |      |
| CTA | GTT | AAT | TGC | TTG | TGG | CCA | GTG | CCC | AGT | TTT | GGC | GTC | GCA | GCA | CAA | 1019 |
| Leu | Val | Asn | Cys | Leu | Trp | Pro | Val | Pro | Ser | Phe | Gly | Val | Ala | Ala | Gln |      |
| 305 |     |     |     | 310 |     |     |     |     | 315 |     |     |     |     | 320 |     |      |
| GAA | TTT | TGT | TTT | GAA | GGT | GCT | CAG | TTT | AGC | CAA | TGT | AAC | GGT | GTT | TCT | 1067 |
| Glu | Phe | Cys | Phe | Glu | Gly | Ala | Gln | Phe | Ser | Gln | Cys | Asn | Gly | Val | Ser |      |
|     |     |     |     | 325 |     |     |     |     | 330 |     |     |     |     | 335 |     |      |
| TTA | AAT | AAT | ACA | GTA | GAT | GTT | ATT | AGA | TTT | AAC | CTT | AAT | TTC | ACT | ACA | 1115 |
| Leu | Asn | Asn | Thr | Val | Asp | Val | Ile | Arg | Phe | Asn | Leu | Asn | Phe | Thr | Thr |      |
|     |     |     | 340 |     |     |     |     | 345 |     |     |     |     | 350 |     |     |      |
| GAT | GTA | CAA | TCT | GGC | ATG | GGT | GCT | ACA | GTA | TTT | TCA | CTG | AAT | ACA | ACA | 1163 |
| Asp | Val | Gln | Ser | Gly | Met | Gly | Ala | Thr | Val | Phe | Ser | Leu | Asn | Thr | Thr |      |
|     |     | 355 |     |     |     |     | 360 |     |     |     |     | 365 |     |     |     |      |
| GGC | GGT | GTC | ATT | CTT | GAG | ATT | TCT | TGT | TAT | AAT | GAC | ACA | GTG | AGT | GAG | 1211 |
| Gly | Gly | Val | Ile | Leu | Glu | Ile | Ser | Cys | Tyr | Asn | Asp | Thr | Val | Ser | Glu |      |
| 370 |     |     |     |     | 375 |     |     |     |     | 380 |     |     |     |     |     |      |
| TCG | AGT | TTC | TAC | AGT | TAT | GGT | GAA | ATT | CCA | TTC | GGC | GTA | ACT | GAT | GGA | 1259 |
| Ser | Ser | Phe | Tyr | Ser | Tyr | Gly | Glu | Ile | Pro | Phe | Gly | Val | Thr | Asp | Gly |      |
| 385 |     |     |     |     | 390 |     |     |     |     | 395 |     |     |     |     | 400 |      |
| CCA | CGT | TAC | TGT | TAT | GTA | CTC | TAC | AAT | GGC | ACA | GCT | CTT | AAG | TAT | TTA | 1307 |
| Pro | Arg | Tyr | Cys | Tyr | Val | Leu | Tyr | Asn | Gly | Thr | Ala | Leu | Lys | Tyr | Leu |      |
|     |     |     |     | 405 |     |     |     |     | 410 |     |     |     |     | 415 |     |      |
| GGA | ACA | TTA | CCA | CCT | AGT | GTC | AAG | GAA | ATT | GCT | ATT | AGT | AAG | TGG | GGA | 1355 |
| Gly | Thr | Leu | Pro | Pro | Ser | Val | Lys | Glu | Ile | Ala | Ile | Ser | Lys | Trp | Gly |      |
|     |     |     | 420 |     |     |     |     | 425 |     |     |     |     | 430 |     |     |      |
| CAT | TTT | TAT | ATT | AAT | GGT | TAC | AAT | TTC | TTT | AGC | ACG | TTT | CCT | ATT | GAT | 1403 |
| His | Phe | Tyr | Ile | Asn | Gly | Tyr | Asn | Phe | Phe | Ser | Thr | Phe | Pro | Ile | Asp |      |
|     |     | 435 |     |     |     |     | 440 |     |     |     |     | 445 |     |     |     |      |
| TGT | ATA | GCT | TTT | AAT | TTA | ACC | ACT | GGT | GCT | AGT | GGA | GCA | TTT | TGG | ACA | 1451 |
| Cys | Ile | Ala | Phe | Asn | Leu | Thr | Thr | Gly | Ala | Ser | Gly | Ala | Phe | Trp | Thr |      |
| 450 |     |     |     |     | 455 |     |     |     |     | 460 |     |     |     |     |     |      |
| ATT | GCT | TAT | ACG | TCG | TAC | ACA | GAA | GCA | TTA | GTA | CAA | GTT | GAA | AAC | ACA | 1499 |
| Ile | Ala | Tyr | Thr | Ser | Tyr | Thr | Glu | Ala | Leu | Val | Gln | Val | Glu | Asn | Thr |      |
| 465 |     |     |     |     | 470 |     |     |     |     | 475 |     |     |     |     | 480 |      |
| GCT | ATT | AAA | AAG | GTG | ACG | TAT | TGT | AAC | AGT | CAC | ATT | AAT | AAC | ATC | AAA | 1547 |
| Ala | Ile | Lys | Lys | Val | Thr | Tyr | Cys | Asn | Ser | His | Ile | Asn | Asn | Ile | Lys |      |
|     |     |     |     | 485 |     |     |     |     | 490 |     |     |     |     | 495 |     |      |
| TGT | TCT | CAA | CTT | ACT | GCT | AAT | TTG | CAA | AAT | GGT | TTT | TAC | CCT | GTT | GCT | 1595 |
| Cys | Ser | Gln | Leu | Thr | Ala | Asn | Leu | Gln | Asn | Gly | Phe | Tyr | Pro | Val | Ala |      |
|     |     |     | 500 |     |     |     |     | 505 |     |     |     |     | 510 |     |     |      |
| TCA | AGT | GAA | GTT | GGT | CTT | GTC | AAT | AAG | AGT | GTT | GTG | TTA | CTA | CCT | AGT | 1643 |
| Ser | Ser | Glu | Val | Gly | Leu | Val | Asn | Lys | Ser | Val | Val | Leu | Leu | Pro | Ser |      |
|     |     | 515 |     |     |     |     | 520 |     |     |     |     | 525 |     |     |     |      |
| TTC | TAT | TCA | CAT | ACC | AGT | GTT | AAT | ATA | ACT | ATT | GAT | CTT | GGT | ATG | AAG | 1691 |
| Phe | Tyr | Ser | His | Thr | Ser | Val | Asn | Ile | Thr | Ile | Asp | Leu | Gly | Met | Lys |      |
|     | 530 |     |     |     |     | 535 |     |     |     |     | 540 |     |     |     |     |      |
| CGT | AGT | GTT | ACG | GTC | ACC | ATA | GCC | TCA | CCA | TTA | AGT | AAC | ATC | ACA | CTA | 1739 |
| Arg | Ser | Val | Thr | Val | Thr | Ile | Ala | Ser | Pro | Leu | Ser | Asn | Ile | Thr | Leu |      |
| 545 |     |     |     |     | 550 |     |     |     |     | 555 |     |     |     |     | 560 |      |
| CCA | ATG | CAG | GAT | AAT | AAC | ATA | GAC | GTG | TAC | TGT | ATT | CGT | TCT | AAC | CAA | 1787 |
| Pro | Met | Gln | Asp | Asn | Asn | Ile | Asp | Val | Tyr | Cys | Ile | Arg | Ser | Asn | Gln |      |

-continued

|  |  |  | 565 |  |  |  |  | 570 |  |  |  |  | 575 |  |  |
|---|---|---|---|---|---|---|---|---|---|---|---|---|---|---|---|
| TTC | TCA | GTT | TAT | GTT | CAT | TCC | ACT | TGC | AAA | AGT | TCT | TTA | TGG | GAT | AAC | 1835 |
| Phe | Ser | Val | Tyr | Val | His | Ser | Thr | Cys | Lys | Ser | Ser | Leu | Trp | Asp | Asn |  |
|  |  |  | 580 |  |  |  |  | 585 |  |  |  |  | 590 |  |  |  |
| AAT | TTT | AAT | TCA | GCA | TGT | ACC | GAC | GTT | TTA | GAC | GCC | ACA | GCT | GTT | ATA | 1883 |
| Asn | Phe | Asn | Ser | Ala | Cys | Thr | Asp | Val | Leu | Asp | Ala | Thr | Ala | Val | Ile |  |
|  |  | 595 |  |  |  |  | 600 |  |  |  |  | 605 |  |  |  |  |
| AAA | ACT | GGT | ACT | TGT | CCT | TTC | TCA | TTT | GAT | AAA | TTG | AAT | AAT | TAC | TTA | 1931 |
| Lys | Thr | Gly | Thr | Cys | Pro | Phe | Ser | Phe | Asp | Lys | Leu | Asn | Asn | Tyr | Leu |  |
|  | 610 |  |  |  |  | 615 |  |  |  |  | 620 |  |  |  |  |  |
| ACT | TTT | AAC | AAG | TTC | TGT | TTG | TCG | TTG | AAT | CCC | GTT | GGT | GCC | AAC | TGT | 1979 |
| Thr | Phe | Asn | Lys | Phe | Cys | Leu | Ser | Leu | Asn | Pro | Val | Gly | Ala | Asn | Cys |  |
| 625 |  |  |  |  | 630 |  |  |  |  | 635 |  |  |  |  | 640 |  |
| AAG | TTA | GAT | GTT | GCC | GCC | CGT | ACA | AGA | ACC | AAT | GAG | CAG | GTT | TTT | GGA | 2027 |
| Lys | Leu | Asp | Val | Ala | Ala | Arg | Thr | Arg | Thr | Asn | Glu | Gln | Val | Phe | Gly |  |
|  |  |  |  | 645 |  |  |  |  | 650 |  |  |  |  | 655 |  |  |
| AGT | TTA | TAT | GTA | ATA | TAT | GAA | GAA | GGA | GAC | AAC | ATA | GTG | GGT | GTA | CCG | 2075 |
| Ser | Leu | Tyr | Val | Ile | Tyr | Glu | Glu | Gly | Asp | Asn | Ile | Val | Gly | Val | Pro |  |
|  |  |  | 660 |  |  |  |  | 665 |  |  |  |  | 670 |  |  |  |
| TCT | GAT | AAT | AGT | GGT | TTG | CAC | GAT | TTG | TCA | GTG | TTG | CAC | TTA | GAC | TCT | 2123 |
| Ser | Asp | Asn | Ser | Gly | Leu | His | Asp | Leu | Ser | Val | Leu | His | Leu | Asp | Ser |  |
|  |  | 675 |  |  |  |  | 680 |  |  |  |  | 685 |  |  |  |  |
| TGT | ACA | GAT | TAC | AAT | ATA | TAT | GGT | AGA | ACT | GGT | GTT | GGT | ATT | ATT | AGA | 2171 |
| Cys | Thr | Asp | Tyr | Asn | Ile | Tyr | Gly | Arg | Thr | Gly | Val | Gly | Ile | Ile | Arg |  |
|  | 690 |  |  |  |  | 695 |  |  |  |  | 700 |  |  |  |  |  |
| AAA | ACT | AAC | AGC | ACA | CTA | CTT | AGT | GGC | TTA | TAT | TAC | ACA | TCA | CTA | TCA | 2219 |
| Lys | Thr | Asn | Ser | Thr | Leu | Leu | Ser | Gly | Leu | Tyr | Tyr | Thr | Ser | Leu | Ser |  |
| 705 |  |  |  |  | 710 |  |  |  |  | 715 |  |  |  |  | 720 |  |
| GGT | GAT | TTG | TTA | GGT | TTT | AAA | AAT | GTT | AGT | GAT | GGT | GTT | GTC | TAC | TCT | 2267 |
| Gly | Asp | Leu | Leu | Gly | Phe | Lys | Asn | Val | Ser | Asp | Gly | Val | Val | Tyr | Ser |  |
|  |  |  |  | 725 |  |  |  |  | 730 |  |  |  |  | 735 |  |  |
| GTA | ACG | CCA | TGT | GAT | GTA | AGT | GCA | CAA | GCT | GCT | GTT | ATT | GAT | GGT | GCC | 2315 |
| Val | Thr | Pro | Cys | Asp | Val | Ser | Ala | Gln | Ala | Ala | Val | Ile | Asp | Gly | Ala |  |
|  |  |  | 740 |  |  |  |  | 745 |  |  |  |  | 750 |  |  |  |
| ATA | GTT | GGA | GCT | ATG | ACT | TCC | ATT | AAT | AGT | GAA | CTG | TTA | GGT | CTA | ACT | 2363 |
| Ile | Val | Gly | Ala | Met | Thr | Ser | Ile | Asn | Ser | Glu | Leu | Leu | Gly | Leu | Thr |  |
|  |  | 755 |  |  |  |  | 760 |  |  |  |  | 765 |  |  |  |  |
| CAT | TGG | ACA | ACA | ACA | CCT | AAT | TTT | TAT | TAC | TAC | TCC | ATA | TAT | AAT | TAT | 2411 |
| His | Trp | Thr | Thr | Thr | Pro | Asn | Phe | Tyr | Tyr | Tyr | Ser | Ile | Tyr | Asn | Tyr |  |
|  | 770 |  |  |  |  | 775 |  |  |  |  | 780 |  |  |  |  |  |
| ACA | AAT | GTG | ATG | AAT | CGT | GGC | ACG | GCA | ATT | GAT | AAT | GAT | ATT | GAT | TGT | 2459 |
| Thr | Asn | Val | Met | Asn | Arg | Gly | Thr | Ala | Ile | Asp | Asn | Asp | Ile | Asp | Cys |  |
| 785 |  |  |  |  | 790 |  |  |  |  | 795 |  |  |  |  | 800 |  |
| GAA | CCT | ATC | ATA | ACA | TAT | TCT | AAT | ATA | GGT | GTT | TGT | AAA | AAT | GGA | GCT | 2507 |
| Glu | Pro | Ile | Ile | Thr | Tyr | Ser | Asn | Ile | Gly | Val | Cys | Lys | Asn | Gly | Ala |  |
|  |  |  |  | 805 |  |  |  |  | 810 |  |  |  |  | 815 |  |  |
| TTG | GTT | TTT | ATT | AAC | GTC | ACA | CAT | TCT | GAT | GGA | GAC | GTT | CAA | CCA | ATT | 2555 |
| Leu | Val | Phe | Ile | Asn | Val | Thr | His | Ser | Asp | Gly | Asp | Val | Gln | Pro | Ile |  |
|  |  |  | 820 |  |  |  |  | 825 |  |  |  |  | 830 |  |  |  |
| AGC | ACC | GGT | AAT | GTC | ACG | ATA | CCC | ACA | AAT | TTT | ACT | ATA | TCT | GTG | CAA | 2603 |
| Ser | Thr | Gly | Asn | Val | Thr | Ile | Pro | Thr | Asn | Phe | Thr | Ile | Ser | Val | Gln |  |
|  |  | 835 |  |  |  |  | 840 |  |  |  |  | 845 |  |  |  |  |
| GTC | GAA | TAT | ATT | CAG | GTT | TAC | ACT | ACA | CCA | GTT | TCA | ATA | GAC | TGT | GCA | 2651 |
| Val | Glu | Tyr | Ile | Gln | Val | Tyr | Thr | Thr | Pro | Val | Ser | Ile | Asp | Cys | Ala |  |
|  | 850 |  |  |  |  | 855 |  |  |  |  | 860 |  |  |  |  |  |
| AGA | TAC | GTT | TGC | AAT | GGT | AAC | CCA | AGA | TGC | AAT | AAG | TTA | TTA | ACA | CAA | 2699 |
| Arg | Tyr | Val | Cys | Asn | Gly | Asn | Pro | Arg | Cys | Asn | Lys | Leu | Leu | Thr | Gln |  |
| 865 |  |  |  |  | 870 |  |  |  |  | 875 |  |  |  |  | 880 |  |
| TAC | GTT | TCT | GCA | TGT | CAA | ACT | ATT | GAG | CAA | GCG | CTT | GCA | ATG | GGT | GCC | 2747 |
| Tyr | Val | Ser | Ala | Cys | Gln | Thr | Ile | Glu | Gln | Ala | Leu | Ala | Met | Gly | Ala |  |

|  |  |  |  |  |  |  |  |  |  |  |  |  |  |  |  |  |
|---|---|---|---|---|---|---|---|---|---|---|---|---|---|---|---|---|
|  |  |  |  | 885 |  |  |  |  |  | 890 |  |  |  |  | 895 |  |
| AGA | CTT | GAA | AAC | ATG | GAG | ATT | GAT | TCC | ATG | TTA | TTT | GTT | TCG | GAA | AAT | 2795 |
| Arg | Leu | Glu | Asn | Met | Glu | Ile | Asp | Ser | Met | Leu | Phe | Val | Ser | Glu | Asn |  |
|  |  |  |  | 900 |  |  |  | 905 |  |  |  |  | 910 |  |  |  |
| GCC | CTT | AAA | TTG | GCA | TCT | GTT | GAA | GCA | TTC | AAT | AGT | ACG | GAA | AAT | TTA | 2843 |
| Ala | Leu | Lys | Leu | Ala | Ser | Val | Glu | Ala | Phe | Asn | Ser | Thr | Glu | Asn | Leu |  |
|  |  | 915 |  |  |  | 920 |  |  |  |  | 925 |  |  |  |  |  |
| GAC | CCT | ATT | TAT | AAA | GAA | TGG | CCT | AAC | ATT | GGT | GGT | TCT | TGG | CTA | GGA | 2891 |
| Asp | Pro | Ile | Tyr | Lys | Glu | Trp | Pro | Asn | Ile | Gly | Gly | Ser | Trp | Leu | Gly |  |
|  | 930 |  |  |  |  | 935 |  |  |  |  | 940 |  |  |  |  |  |
| GGT | TTA | AAA | GAT | ATA | TTG | CCA | TCT | CAT | AAT | AGC | AAA | CGT | AAG | TAC | CGC | 2939 |
| Gly | Leu | Lys | Asp | Ile | Leu | Pro | Ser | His | Asn | Ser | Lys | Arg | Lys | Tyr | Arg |  |
| 945 |  |  |  | 950 |  |  |  | 955 |  |  |  | 960 |  |  |  |  |
| TCG | GCT | ATA | GAA | GAC | TTG | CTT | TTT | GAT | AAG | GTT | GTA | ACA | TCT | GGC | TTA | 2987 |
| Ser | Ala | Ile | Glu | Asp | Leu | Leu | Phe | Asp | Lys | Val | Val | Thr | Ser | Gly | Leu |  |
|  |  |  |  | 965 |  |  |  | 970 |  |  |  |  | 975 |  |  |  |
| GGT | ACA | GTT | GAC | GAA | GAT | TAC | AAA | CGT | TCT | GCA | GGT | GGT | TAT | GAC | ATA | 3035 |
| Gly | Thr | Val | Asp | Glu | Asp | Tyr | Lys | Arg | Ser | Ala | Gly | Gly | Tyr | Asp | Ile |  |
|  |  |  | 980 |  |  |  |  | 985 |  |  |  |  | 990 |  |  |  |
| GCT | GAC | TTA | GTG | TGT | GCA | CGA | TAT | TAC | AAT | GGC | ATC | ATG | GTG | CTA | CCT | 3083 |
| Ala | Asp | Leu | Val | Cys | Ala | Arg | Tyr | Tyr | Asn | Gly | Ile | Met | Val | Leu | Pro |  |
|  |  | 995 |  |  |  |  | 1000 |  |  |  |  | 1005 |  |  |  |  |
| GGT | GTA | GCT | AAT | GAT | GAC | AAG | ATG | ACT | ATG | TAC | ACT | GCA | TCT | CTT | ACA | 3131 |
| Gly | Val | Ala | Asn | Asp | Asp | Lys | Met | Thr | Met | Tyr | Thr | Ala | Ser | Leu | Thr |  |
|  | 1010 |  |  |  |  | 1015 |  |  |  |  | 1020 |  |  |  |  |  |
| GGT | GGT | ATA | ACA | TTA | GGT | GCA | CTT | AGT | GGT | GGC | GCA | GTG | GCT | ATA | CCT | 3179 |
| Gly | Gly | Ile | Thr | Leu | Gly | Ala | Leu | Ser | Gly | Gly | Ala | Val | Ala | Ile | Pro |  |
| 1025 |  |  |  |  | 1030 |  |  |  |  | 1035 |  |  |  |  | 1040 |  |
| TTT | GCA | GTA | GCA | GTT | CAG | GCT | AGA | CTT | AAT | TAT | GTT | GCT | CTA | CAA | ACT | 3227 |
| Phe | Ala | Val | Ala | Val | Gln | Ala | Arg | Leu | Asn | Tyr | Val | Ala | Leu | Gln | Thr |  |
|  |  |  |  | 1045 |  |  |  |  | 1050 |  |  |  |  | 1055 |  |  |
| GAT | GTA | TTG | AAC | AAA | AAC | CAA | CAA | ATC | TTG | GCT | AAT | GCT | TTC | AAT | CAA | 3275 |
| Asp | Val | Leu | Asn | Lys | Asn | Gln | Gln | Ile | Leu | Ala | Asn | Ala | Phe | Asn | Gln |  |
|  |  |  | 1060 |  |  |  |  | 1065 |  |  |  |  | 1070 |  |  |  |
| GCT | ATT | GGT | AAC | ATT | ACA | CAG | GCA | TTT | GGT | AAG | GTT | AAT | GAC | GCT | ATA | 3323 |
| Ala | Ile | Gly | Asn | Ile | Thr | Gln | Ala | Phe | Gly | Lys | Val | Asn | Asp | Ala | Ile |  |
|  |  | 1075 |  |  |  |  | 1080 |  |  |  |  | 1085 |  |  |  |  |
| CAT | CAA | ACA | TCA | AAA | GGT | CTT | GCT | ACT | GTT | GCT | AAA | GCA | TTG | GCA | AAG | 3371 |
| His | Gln | Thr | Ser | Lys | Gly | Leu | Ala | Thr | Val | Ala | Lys | Ala | Leu | Ala | Lys |  |
|  | 1090 |  |  |  |  | 1095 |  |  |  |  | 1100 |  |  |  |  |  |
| GTG | CAA | GAT | GTT | GTT | AAC | ACG | CAA | GGT | CAA | GCT | TTA | AGC | CAC | CTA | ACA | 3419 |
| Val | Gln | Asp | Val | Val | Asn | Thr | Gln | Gly | Gln | Ala | Leu | Ser | His | Leu | Thr |  |
| 1105 |  |  |  |  | 1110 |  |  |  |  | 1115 |  |  |  |  | 1120 |  |
| GTA | CAA | TTG | CAA | AAC | AAT | TTT | CAA | GCC | ATT | AGC | AGT | TCT | ATT | AGT | GAC | 3467 |
| Val | Gln | Leu | Gln | Asn | Asn | Phe | Gln | Ala | Ile | Ser | Ser | Ser | Ile | Ser | Asp |  |
|  |  |  |  | 1125 |  |  |  |  | 1130 |  |  |  |  | 1135 |  |  |
| ATT | TAT | AAC | AGG | CTT | GAT | GAA | TTG | AGT | GCT | GAT | GCA | CAA | GTT | GAC | AGG | 3515 |
| Ile | Tyr | Asn | Arg | Leu | Asp | Glu | Leu | Ser | Ala | Asp | Ala | Gln | Val | Asp | Arg |  |
|  |  |  | 1140 |  |  |  |  | 1145 |  |  |  |  | 1150 |  |  |  |
| CTG | ATT | ACA | GGA | CGA | CTT | ACA | GCA | CTT | AAT | GCA | TTT | GTG | TCT | CAG | ACT | 3563 |
| Leu | Ile | Thr | Gly | Arg | Leu | Thr | Ala | Leu | Asn | Ala | Phe | Val | Ser | Gln | Thr |  |
|  |  | 1155 |  |  |  |  | 1160 |  |  |  |  | 1165 |  |  |  |  |
| TTA | ACC | AGA | CAA | GCA | GAG | GTT | AGG | GCT | AGT | AGA | CAA | CTT | GCT | AAA | GAC | 3611 |
| Leu | Thr | Arg | Gln | Ala | Glu | Val | Arg | Ala | Ser | Arg | Gln | Leu | Ala | Lys | Asp |  |
|  | 1170 |  |  |  |  | 1175 |  |  |  |  | 1180 |  |  |  |  |  |
| AAG | GTT | AAT | GAA | TGC | GTT | AGG | TCT | CAA | TCC | CAG | AGA | TTT | GGA | TTC | TGT | 3659 |
| Lys | Val | Asn | Glu | Cys | Val | Arg | Ser | Gln | Ser | Gln | Arg | Phe | Gly | Phe | Cys |  |
| 1185 |  |  |  |  | 1190 |  |  |  |  | 1195 |  |  |  |  | 1200 |  |
| GGT | AAT | GGT | ACA | CAT | TTG | TTT | TCA | CTT | GCA | AAT | GCG | GCA | CCA | AAT | GGC | 3707 |
| Gly | Asn | Gly | Thr | His | Leu | Phe | Ser | Leu | Ala | Asn | Ala | Ala | Pro | Asn | Gly |  |

-continued

```
                 1205                      1210                      1215
ATG ATT TTC TTT CAC ACA GTG CTA TTA CCA ACA GCT TAT GAA ACT GTG              3755
Met Ile Phe Phe His Thr Val Leu Leu Pro Thr Ala Tyr Glu Thr Val
            1220              1225              1230

ACG GCC TGG TCA GGT ATT TGT GCG TCA GAT GGC AGT CGC ACT TTT GGA              3803
Thr Ala Trp Ser Gly Ile Cys Ala Ser Asp Gly Ser Arg Thr Phe Gly
        1235              1240              1245

CTT GTT GTT GAG GAT GTC CAG CTG ACG CTA TTT CGC AAT TTA GAT GAA              3851
Leu Val Val Glu Asp Val Gln Leu Thr Leu Phe Arg Asn Leu Asp Glu
1250              1255              1260

AAA TTT TAT TTG ACG CCC AGA ACT ATG TAT CAG CCC AGA GTT GCA ACT              3899
Lys Phe Tyr Leu Thr Pro Arg Thr Met Tyr Gln Pro Arg Val Ala Thr
1265              1270              1275              1280

AGT TCT GAT TTT GTT CAA ATA GAA GGC TGT GAT GTG TTG TTT GTT AAT              3947
Ser Ser Asp Phe Val Gln Ile Glu Gly Cys Asp Val Leu Phe Val Asn
                1285              1290              1295

GGA ACT GTA ATT GAA TTG CCT AGT ATC ATA CCT GAC TAT ATC GAT ATT              3995
Gly Thr Val Ile Glu Leu Pro Ser Ile Ile Pro Asp Tyr Ile Asp Ile
            1300              1305              1310

AAT CAA ACT GTT CAG GAC ATA TTA GAA AAT TTC AGA CCA AAT TGG ACT              4043
Asn Gln Thr Val Gln Asp Ile Leu Glu Asn Phe Arg Pro Asn Trp Thr
        1315              1320              1325

GTA CCC GAG TTG CCA CTT GAC ATT TTT CAT GCA ACC TAC TTA AAC CTG              4091
Val Pro Glu Leu Pro Leu Asp Ile Phe His Ala Thr Tyr Leu Asn Leu
1330              1335              1340

ACT GGT GAA ATT AAT GAC TTA GAA TTT AGG TCA GAA AAG TTA CAT AAC              4139
Thr Gly Glu Ile Asn Asp Leu Glu Phe Arg Ser Glu Lys Leu His Asn
1345              1350              1355              1360

ACC ACA GTA GAA CTT GCT ATT CTC ATT GAT AAT ATT AAT AAC ACA TTA              4187
Thr Thr Val Glu Leu Ala Ile Leu Ile Asp Asn Ile Asn Asn Thr Leu
                1365              1370              1375

GTC AAT CTT GAA TGG CTC AAC AGA ATT GAA ACT TAT GTA AAA TGG CCT              4235
Val Asn Leu Glu Trp Leu Asn Arg Ile Glu Thr Tyr Val Lys Trp Pro
            1380              1385              1390

TGG TAT GTT TGG CTA CTA ATT GGA TTA GTA GTA ATA TTC TGC ATA CCC              4283
Trp Tyr Val Trp Leu Leu Ile Gly Leu Val Val Ile Phe Cys Ile Pro
        1395              1400              1405

ATA TTG CTA TTT TGT TGT TGT AGT ACT GGT TGT TGT GGA TGT ATC GGG              4331
Ile Leu Leu Phe Cys Cys Cys Ser Thr Gly Cys Cys Gly Cys Ile Gly
1410              1415              1420

TGT TTA GGA AGC TGT TGT CAT TCC ATA TGT AGT AGA GGC CAA TTT GAA              4379
Cys Leu Gly Ser Cys Cys His Ser Ile Cys Ser Arg Gly Gln Phe Glu
1425              1430              1435              1440

AGT TAT GAA CCT ATT GAA AAA GTT CAT GTT CAC TGAATTCAAA ATGTTAA               4429
Ser Tyr Glu Pro Ile Glu Lys Val His Val His
                1445              1450
```

( 2 ) INFORMATION FOR SEQ ID NO:4:

( i ) SEQUENCE CHARACTERISTICS:
        ( A ) LENGTH: 1451 amino acids
        ( B ) TYPE: amino acid
        ( C ) STRANDEDNESS: single
        ( D ) TOPOLOGY: linear ( i i ) MOLECULE TYPE: protein ( v i ) ORIGINAL SOURCE:
        ( A ) ORGANISM: Canine corona virus
        ( B ) STRAIN: CCVInSAVC-1

( i x ) FEATURE:
        ( A ) NAME/KEY: Protein
        ( B ) LOCATION: 1..1451

( D ) OTHER INFORMATION: /label=CCVInSAVC-1_Spike ( x i ) SEQUENCE DESCRIPTION: SEQ ID NO:4:

```
Met Ile Val Leu Thr Leu Cys Leu Phe Leu Phe Leu Tyr Ser Ser Val
1               5                   10                  15

Ser Cys Thr Ser Asn Asn Asp Cys Val Gln Val Asn Val Thr Gln Leu
            20                  25                  30

Pro Gly Asn Glu Asn Ile Ile Lys Asp Phe Leu Phe Gln Asn Phe Lys
        35                  40                  45

Glu Glu Gly Ser Leu Val Gly Gly Tyr Tyr Pro Thr Glu Val Trp
    50                  55                  60

Tyr Asn Cys Ser Thr Thr Gln Gln Thr Thr Ala Tyr Lys Tyr Phe Ser
65              70                  75                      80

Asn Ile His Ala Phe Tyr Phe Asp Met Glu Ala Met Glu Asn Ser Thr
                85                  90                  95

Gly Asn Ala Arg Gly Lys Pro Leu Leu Val His Val His Gly Asn Pro
            100                 105                 110

Val Ser Ile Ile Val Tyr Ile Ser Ala Tyr Arg Asp Asp Val Gln Phe
        115                 120                 125

Arg Pro Leu Leu Lys His Gly Leu Leu Cys Ile Thr Lys Asn Asp Thr
    130                 135                 140

Val Asp Tyr Asn Ser Phe Thr Ile Asn Gln Trp Arg Asp Ile Cys Leu
145                 150                 155                 160

Gly Asp Asp Arg Lys Ile Pro Phe Ser Val Val Pro Thr Asp Asn Gly
                165                 170                 175

Thr Lys Leu Phe Gly Leu Glu Trp Asn Asp Asp Tyr Val Thr Ala Tyr
            180                 185                 190

Ile Ser Asp Glu Ser His Arg Leu Asn Ile Asn Asn Asn Trp Phe Asn
        195                 200                 205

Asn Val Thr Leu Leu Tyr Ser Arg Thr Ser Thr Ala Thr Trp Gln His
    210                 215                 220

Ser Ala Ala Tyr Val Tyr Gln Gly Val Ser Asn Phe Thr Tyr Tyr Lys
225                 230                 235                 240

Leu Asn Lys Thr Ala Gly Leu Lys Ser Tyr Glu Leu Cys Glu Asp Tyr
                245                 250                 255

Glu Tyr Cys Thr Gly Tyr Ala Thr Asn Val Phe Ala Pro Thr Ser Gly
            260                 265                 270

Gly Tyr Ile Pro Asp Gly Phe Ser Phe Asn Asn Trp Phe Met Leu Thr
        275                 280                 285

Asn Ser Ser Thr Phe Val Ser Gly Arg Phe Val Thr Asn Gln Pro Leu
    290                 295                 300

Leu Val Asn Cys Leu Trp Pro Val Pro Ser Phe Gly Val Ala Ala Gln
305                 310                 315                 320

Glu Phe Cys Phe Glu Gly Ala Gln Phe Ser Gln Cys Asn Gly Val Ser
                325                 330                 335

Leu Asn Asn Thr Val Asp Val Ile Arg Phe Asn Leu Asn Phe Thr Thr
            340                 345                 350

Asp Val Gln Ser Gly Met Gly Ala Thr Val Phe Ser Leu Asn Thr Thr
        355                 360                 365

Gly Gly Val Ile Leu Glu Ile Ser Cys Tyr Asn Asp Thr Val Ser Glu
    370                 375                 380

Ser Ser Phe Tyr Ser Tyr Gly Glu Ile Pro Phe Gly Val Thr Asp Gly
385                 390                 395                 400

Pro Arg Tyr Cys Tyr Val Leu Tyr Asn Gly Thr Ala Leu Lys Tyr Leu
```

-continued

|     |     |     | 405 |     |     |     |     | 410 |     |     |     |     | 415 |     |
| --- | --- | --- | --- | --- | --- | --- | --- | --- | --- | --- | --- | --- | --- | --- |

Gly Thr Leu Pro Pro Ser Val Lys Glu Ile Ala Ile Ser Lys Trp Gly
            420             425             430

His Phe Tyr Ile Asn Gly Tyr Asn Phe Phe Ser Thr Phe Pro Ile Asp
            435             440             445

Cys Ile Ala Phe Asn Leu Thr Thr Gly Ala Ser Gly Ala Phe Trp Thr
        450             455             460

Ile Ala Tyr Thr Ser Tyr Thr Glu Ala Leu Val Gln Val Glu Asn Thr
465             470             475             480

Ala Ile Lys Lys Val Thr Tyr Cys Asn Ser His Ile Asn Asn Ile Lys
                485             490             495

Cys Ser Gln Leu Thr Ala Asn Leu Gln Asn Gly Phe Tyr Pro Val Ala
            500             505             510

Ser Ser Glu Val Gly Leu Val Asn Lys Ser Val Val Leu Leu Pro Ser
        515             520             525

Phe Tyr Ser His Thr Ser Val Asn Ile Thr Ile Asp Leu Gly Met Lys
    530             535             540

Arg Ser Val Thr Val Thr Ile Ala Ser Pro Leu Ser Asn Ile Thr Leu
545             550             555             560

Pro Met Gln Asp Asn Asn Ile Asp Val Tyr Cys Ile Arg Ser Asn Gln
                565             570             575

Phe Ser Val Tyr Val His Ser Thr Cys Lys Ser Ser Leu Trp Asp Asn
            580             585             590

Asn Phe Asn Ser Ala Cys Thr Asp Val Leu Asp Ala Thr Ala Val Ile
        595             600             605

Lys Thr Gly Thr Cys Pro Phe Ser Phe Asp Lys Leu Asn Asn Tyr Leu
610             615             620

Thr Phe Asn Lys Phe Cys Leu Ser Leu Asn Pro Val Gly Ala Asn Cys
625             630             635             640

Lys Leu Asp Val Ala Ala Arg Thr Arg Thr Asn Glu Gln Val Phe Gly
                645             650             655

Ser Leu Tyr Val Ile Tyr Glu Glu Gly Asp Asn Ile Val Gly Val Pro
            660             665             670

Ser Asp Asn Ser Gly Leu His Asp Leu Ser Val Leu His Leu Asp Ser
        675             680             685

Cys Thr Asp Tyr Asn Ile Tyr Gly Arg Thr Gly Val Gly Ile Ile Arg
    690             695             700

Lys Thr Asn Ser Thr Leu Leu Ser Gly Leu Tyr Tyr Thr Ser Leu Ser
705             710             715             720

Gly Asp Leu Leu Gly Phe Lys Asn Val Ser Asp Gly Val Val Tyr Ser
                725             730             735

Val Thr Pro Cys Asp Val Ser Ala Gln Ala Ala Val Ile Asp Gly Ala
            740             745             750

Ile Val Gly Ala Met Thr Ser Ile Asn Ser Glu Leu Leu Gly Leu Thr
        755             760             765

His Trp Thr Thr Thr Pro Asn Phe Tyr Tyr Tyr Ser Ile Tyr Asn Tyr
    770             775             780

Thr Asn Val Met Asn Arg Gly Thr Ala Ile Asp Asn Asp Ile Asp Cys
785             790             795             800

Glu Pro Ile Ile Thr Tyr Ser Asn Ile Gly Val Cys Lys Asn Gly Ala
                805             810             815

Leu Val Phe Ile Asn Val Thr His Ser Asp Gly Asp Val Gln Pro Ile
            820             825             830

```
Ser  Thr  Gly  Asn  Val  Thr  Ile  Pro  Thr  Asn  Phe  Thr  Ile  Ser  Val  Gln
          835                 840                 845

Val  Glu  Tyr  Ile  Gln  Val  Tyr  Thr  Thr  Pro  Val  Ser  Ile  Asp  Cys  Ala
850                      855                      860

Arg  Tyr  Val  Cys  Asn  Gly  Asn  Pro  Arg  Cys  Asn  Lys  Leu  Leu  Thr  Gln
865                      870                      875                      880

Tyr  Val  Ser  Ala  Cys  Gln  Thr  Ile  Glu  Gln  Ala  Leu  Ala  Met  Gly  Ala
                    885                      890                      895

Arg  Leu  Glu  Asn  Met  Glu  Ile  Asp  Ser  Met  Leu  Phe  Val  Ser  Glu  Asn
               900                 905                 910

Ala  Leu  Lys  Leu  Ala  Ser  Val  Glu  Ala  Phe  Asn  Ser  Thr  Glu  Asn  Leu
          915                 920                      925

Asp  Pro  Ile  Tyr  Lys  Glu  Trp  Pro  Asn  Ile  Gly  Gly  Ser  Trp  Leu  Gly
930                      935                      940

Gly  Leu  Lys  Asp  Ile  Leu  Pro  Ser  His  Asn  Ser  Lys  Arg  Lys  Tyr  Arg
945                 950                      955                           960

Ser  Ala  Ile  Glu  Asp  Leu  Leu  Phe  Asp  Lys  Val  Val  Thr  Ser  Gly  Leu
               965                 970                      975

Gly  Thr  Val  Asp  Glu  Asp  Tyr  Lys  Arg  Ser  Ala  Gly  Gly  Tyr  Asp  Ile
               980                 985                      990

Ala  Asp  Leu  Val  Cys  Ala  Arg  Tyr  Tyr  Asn  Gly  Ile  Met  Val  Leu  Pro
          995                      1000                     1005

Gly  Val  Ala  Asn  Asp  Asp  Lys  Met  Thr  Met  Tyr  Thr  Ala  Ser  Leu  Thr
1010                     1015                     1020

Gly  Gly  Ile  Thr  Leu  Gly  Ala  Leu  Ser  Gly  Gly  Ala  Val  Ala  Ile  Pro
1025                     1030                     1035                     1040

Phe  Ala  Val  Ala  Val  Gln  Ala  Arg  Leu  Asn  Tyr  Val  Ala  Leu  Gln  Thr
                    1045                     1050                     1055

Asp  Val  Leu  Asn  Lys  Asn  Gln  Gln  Ile  Leu  Ala  Asn  Ala  Phe  Asn  Gln
                    1060                     1065                     1070

Ala  Ile  Gly  Asn  Ile  Thr  Gln  Ala  Phe  Gly  Lys  Val  Asn  Asp  Ala  Ile
                    1075                     1080                     1085

His  Gln  Thr  Ser  Lys  Gly  Leu  Ala  Thr  Val  Ala  Lys  Ala  Leu  Ala  Lys
     1090                     1095                     1100

Val  Gln  Asp  Val  Val  Asn  Thr  Gln  Gly  Gln  Ala  Leu  Ser  His  Leu  Thr
1105                     1110                     1115                     1120

Val  Gln  Leu  Gln  Asn  Asn  Phe  Gln  Ala  Ile  Ser  Ser  Ser  Ile  Ser  Asp
                    1125                     1130                     1135

Ile  Tyr  Asn  Arg  Leu  Asp  Glu  Leu  Ser  Ala  Asp  Ala  Gln  Val  Asp  Arg
               1140                     1145                     1150

Leu  Ile  Thr  Gly  Arg  Leu  Thr  Ala  Leu  Asn  Ala  Phe  Val  Ser  Gln  Thr
               1155                     1160                     1165

Leu  Thr  Arg  Gln  Ala  Glu  Val  Arg  Ala  Ser  Arg  Gln  Leu  Ala  Lys  Asp
     1170                     1175                     1180

Lys  Val  Asn  Glu  Cys  Val  Arg  Ser  Gln  Ser  Gln  Arg  Phe  Gly  Phe  Cys
1185                     1190                     1195                     1200

Gly  Asn  Gly  Thr  His  Leu  Phe  Ser  Leu  Ala  Asn  Ala  Ala  Pro  Asn  Gly
                    1205                     1210                     1215

Met  Ile  Phe  Phe  His  Thr  Val  Leu  Leu  Pro  Thr  Ala  Tyr  Glu  Thr  Val
                    1220                     1225                     1230

Thr  Ala  Trp  Ser  Gly  Ile  Cys  Ala  Ser  Asp  Gly  Ser  Arg  Thr  Phe  Gly
               1235                     1240                     1245

Leu  Val  Val  Glu  Asp  Val  Gln  Leu  Thr  Leu  Phe  Arg  Asn  Leu  Asp  Glu
1250                     1255                     1260
```

| | | | | | | | | | | | | | | |
|---|---|---|---|---|---|---|---|---|---|---|---|---|---|---|
| Lys | Phe | Tyr | Leu | Thr | Pro | Arg | Thr | Met | Tyr | Gln | Pro | Arg | Val | Ala | Thr |
| 1265 | | | | 1270 | | | | 1275 | | | | | | 1280 |

Ser Ser Asp Phe Val Gln Ile Glu Gly Cys Asp Val Leu Phe Val Asn
                            1285                         1290                         1295

Gly Thr Val Ile Glu Leu Pro Ser Ile Ile Pro Asp Tyr Ile Asp Ile
              1300                       1305                     1310

Asn Gln Thr Val Gln Asp Ile Leu Glu Asn Phe Arg Pro Asn Trp Thr
           1315                     1320                    1325

Val Pro Glu Leu Pro Leu Asp Ile Phe His Ala Thr Tyr Leu Asn Leu
    1330                     1335                     1340

Thr Gly Glu Ile Asn Asp Leu Glu Phe Arg Ser Glu Lys Leu His Asn
 1345                   1350                  1355               1360

Thr Thr Val Glu Leu Ala Ile Leu Ile Asp Asn Ile Asn Asn Thr Leu
              1365                     1370                   1375

Val Asn Leu Glu Trp Leu Asn Arg Ile Glu Thr Tyr Val Lys Trp Pro
         1380                     1385                     1390

Trp Tyr Val Trp Leu Leu Ile Gly Leu Val Val Ile Phe Cys Ile Pro
             1395                     1400                   1405

Ile Leu Leu Phe Cys Cys Cys Ser Thr Gly Cys Cys Gly Cys Ile Gly
 1410                   1415                     1420

Cys Leu Gly Ser Cys Cys His Ser Ile Cys Ser Arg Gly Gln Phe Glu
 1425                   1430                  1435               1440

Ser Tyr Glu Pro Ile Glu Lys Val His Val His
              1445                     1450

( 2 ) INFORMATION FOR SEQ ID NO:5:

( i ) SEQUENCE CHARACTERISTICS:
        ( A ) LENGTH: 4435 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Canine corona virus
        ( B ) STRAIN: CCV-V54

( i x ) FEATURE:
        ( A ) NAME/KEY: CDS
        ( B ) LOCATION: 60..4418
        ( D ) OTHER INFORMATION: /label=CCV-C54_Spikegene ( x i ) SEQUENCE DESCRIPTION: SEQ ID NO:5:

TTGCTCATTA GAAACAATGG AAAACTACTA AACTTCGGTA ATCACTTGGT TAATGTGCC      59

ATG ATT GTG CTT ACA TTG TGC CTT CTC TTG TTT TCA TAC AAT AGT GTG      107
Met Ile Val Leu Thr Leu Cys Leu Leu Leu Phe Ser Tyr Asn Ser Val
 1              5                 10               15

ATT TGT ACA TCA AAT AAT GAT TGT GTA CAA GTT AAT GTG ACA CAA TTG      155
Ile Cys Thr Ser Asn Asn Asp Cys Val Gln Val Asn Val Thr Gln Leu
          20                  25                  30

CCT GGC AAT GAA AAT ATC ATT AAA GAT TTT CTA TTT CAG AAT TTT AAA      203
Pro Gly Asn Glu Asn Ile Ile Lys Asp Phe Leu Phe Gln Asn Phe Lys
        35                    40                  45

GAA GAA GGA AGT GTA GTT GTT GGT GGC TAC TAC CCC ACA GAG GTG TGG      251
Glu Glu Gly Ser Val Val Val Gly Gly Tyr Tyr Pro Thr Glu Val Trp
    50                    55                  60

TAC AAC TGT TCC AGA ACA GCA ACA ACT ACA GCT TAC CAT TAT TTT AGT      299
Tyr Asn Cys Ser Arg Thr Ala Thr Thr Thr Ala Tyr His Tyr Phe Ser
 65              70                75               80

| | | | | | | | | | | | | | | | | |
|---|---|---|---|---|---|---|---|---|---|---|---|---|---|---|---|---|
| AAC | ATA | CAT | GCA | TTT | TAT | TTT | GAT | ATG | GAA | GCT | ATG | GCG | AAT | AGT | ACT | 347 |
| Asn | Ile | His | Ala | Phe | Tyr | Phe | Asp | Met | Glu | Ala | Met | Ala | Asn | Ser | Thr | |
| | | | | 85 | | | | 90 | | | | | 95 | | | |
| GGC | AAT | GCA | AGA | GGT | AAA | CCT | TTA | CTA | GTA | CAT | GTT | CAT | GGT | AGT | CCT | 395 |
| Gly | Asn | Ala | Arg | Gly | Lys | Pro | Leu | Leu | Val | His | Val | His | Gly | Ser | Pro | |
| | | | 100 | | | | | 105 | | | | | 110 | | | |
| GTT | AGT | ATC | ATT | GTT | TAC | ATA | TCA | GCC | TAT | AGA | GAT | GAT | GTG | CAA | AAT | 443 |
| Val | Ser | Ile | Ile | Val | Tyr | Ile | Ser | Ala | Tyr | Arg | Asp | Asp | Val | Gln | Asn | |
| | | | 115 | | | | 120 | | | | | 125 | | | | |
| AGG | CCG | CTC | TTA | AAA | CAT | GGT | TTG | TTG | TGT | ATA | ACT | AAA | AAC | AGC | ACC | 491 |
| Arg | Pro | Leu | Leu | Lys | His | Gly | Leu | Leu | Cys | Ile | Thr | Lys | Asn | Ser | Thr | |
| | 130 | | | | | 135 | | | | | | 140 | | | | |
| ATT | GAT | TAT | AAC | AGT | TTT | ACC | TCT | GCT | CAG | TGG | CGT | GAC | ATA | TGT | TTG | 539 |
| Ile | Asp | Tyr | Asn | Ser | Phe | Thr | Ser | Ala | Gln | Trp | Arg | Asp | Ile | Cys | Leu | |
| 145 | | | | | 150 | | | | | 155 | | | | | 160 | |
| GGT | ACT | GAC | AGA | AAA | ATA | CCA | TTC | TCC | GTC | GTA | CCC | ACA | GAT | AAT | GGC | 587 |
| Gly | Thr | Asp | Arg | Lys | Ile | Pro | Phe | Ser | Val | Val | Pro | Thr | Asp | Asn | Gly | |
| | | | | 165 | | | | | 170 | | | | | 175 | | |
| ACA | AAA | CTA | TTT | GGT | CTT | GAG | TGG | ACT | GAT | GAC | TAT | GTT | ACA | GCC | TAT | 635 |
| Thr | Lys | Leu | Phe | Gly | Leu | Glu | Trp | Thr | Asp | Asp | Tyr | Val | Thr | Ala | Tyr | |
| | | | 180 | | | | | 185 | | | | | 190 | | | |
| ATT | AGT | GAT | GAT | TCC | CAC | CGT | TTG | AAT | ATC | AAT | ACT | AAT | TGG | TTT | AAC | 683 |
| Ile | Ser | Asp | Asp | Ser | His | Arg | Leu | Asn | Ile | Asn | Thr | Asn | Trp | Phe | Asn | |
| | | | 195 | | | | | 200 | | | | | 205 | | | |
| AAT | GTT | ACA | ATC | CTA | TAC | TCC | CGC | TCA | AGT | ACT | GCC | ACG | TGG | CAA | AAG | 731 |
| Asn | Val | Thr | Ile | Leu | Tyr | Ser | Arg | Ser | Ser | Thr | Ala | Thr | Trp | Gln | Lys | |
| | 210 | | | | | 215 | | | | | | 220 | | | | |
| AGT | GCC | GCA | TAT | GTT | TAT | CAA | GGT | GTT | TCA | AAT | TTT | ACG | TAT | TAT | AAG | 779 |
| Ser | Ala | Ala | Tyr | Val | Tyr | Gln | Gly | Val | Ser | Asn | Phe | Thr | Tyr | Tyr | Lys | |
| 225 | | | | | 230 | | | | | 235 | | | | | 240 | |
| TTA | AAC | AAC | ACC | AAT | GGC | TTA | AAA | AGC | TAT | GAA | TTG | TGT | GAA | GAT | TAT | 827 |
| Leu | Asn | Asn | Thr | Asn | Gly | Leu | Lys | Ser | Tyr | Glu | Leu | Cys | Glu | Asp | Tyr | |
| | | | | 245 | | | | | 250 | | | | | 255 | | |
| GAA | TAC | TGC | ACT | GGC | TAT | GCC | ACC | AAT | GTG | TTT | GCT | CCG | ACA | TCA | GGT | 875 |
| Glu | Tyr | Cys | Thr | Gly | Tyr | Ala | Thr | Asn | Val | Phe | Ala | Pro | Thr | Ser | Gly | |
| | | | 260 | | | | | 265 | | | | | 270 | | | |
| GGT | TAC | ATA | CCT | GAT | GGA | TTC | AGT | TTT | AAC | AAT | TGG | TTT | ATG | CTT | ACA | 923 |
| Gly | Tyr | Ile | Pro | Asp | Gly | Phe | Ser | Phe | Asn | Asn | Trp | Phe | Met | Leu | Thr | |
| | | | 275 | | | | | 280 | | | | | 285 | | | |
| AAC | AGC | TCC | ACT | TTT | GTT | AGT | GGT | AGG | TTT | GTA | ACA | AAT | CAA | CCG | CTG | 971 |
| Asn | Ser | Ser | Thr | Phe | Val | Ser | Gly | Arg | Phe | Val | Thr | Asn | Gln | Pro | Leu | |
| | 290 | | | | | 295 | | | | | | 300 | | | | |
| TTA | GTT | AAT | TGC | TTG | GTG | CCA | GTG | CCC | AGT | TTT | GGT | GTT | GCA | GCA | CAA | 1019 |
| Leu | Val | Asn | Cys | Leu | Val | Pro | Val | Pro | Ser | Phe | Gly | Val | Ala | Ala | Gln | |
| 305 | | | | | 310 | | | | | 315 | | | | | 320 | |
| GAA | TTT | TGT | TTT | GAA | GGT | GCG | CAG | TTT | AGC | CAA | TGT | AAC | GGT | GTT | TCT | 1067 |
| Glu | Phe | Cys | Phe | Glu | Gly | Ala | Gln | Phe | Ser | Gln | Cys | Asn | Gly | Val | Ser | |
| | | | | 325 | | | | | 330 | | | | | 335 | | |
| TTA | AAT | AAC | ACA | GTA | GAT | GTC | ATT | AGA | TTT | AAC | CTT | AAT | TTT | ACT | ACA | 1115 |
| Leu | Asn | Asn | Thr | Val | Asp | Val | Ile | Arg | Phe | Asn | Leu | Asn | Phe | Thr | Thr | |
| | | | 340 | | | | | 345 | | | | | 350 | | | |
| AAT | GTA | CAA | TCT | GGC | ATG | GGT | GCT | ACA | GTA | TTT | TCA | CTG | AAT | ACA | ACA | 1163 |
| Asn | Val | Gln | Ser | Gly | Met | Gly | Ala | Thr | Val | Phe | Ser | Leu | Asn | Thr | Thr | |
| | | | 355 | | | | | 360 | | | | | 365 | | | |
| GGT | GGT | GTC | ATT | CTT | GAG | ATT | TCT | TGT | TAT | AAT | GAT | ACA | GTG | AGT | GAG | 1211 |
| Gly | Gly | Val | Ile | Leu | Glu | Ile | Ser | Cys | Tyr | Asn | Asp | Thr | Val | Ser | Glu | |
| | | | 370 | | | | | 375 | | | | | 380 | | | |
| TCG | AGT | TTC | TAC | AGT | TAT | GGT | GAA | ATT | CCA | TTC | GGC | GTA | ACT | GAT | GGA | 1259 |
| Ser | Ser | Phe | Tyr | Ser | Tyr | Gly | Glu | Ile | Pro | Phe | Gly | Val | Thr | Asp | Gly | |
| 385 | | | | | 390 | | | | | 395 | | | | | 400 | |

```
CCG CGT TAC TGT TAT GTA CTC TAT AAT GGC ACG GCT CTT AAG TAT TTA        1307
Pro Arg Tyr Cys Tyr Val Leu Tyr Asn Gly Thr Ala Leu Lys Tyr Leu
            405                 410                 415

GGA ACA TTA CCA CCT AGT GTC AAG GAA ATT GCT ATT AGT AAG TGG GGC        1355
Gly Thr Leu Pro Pro Ser Val Lys Glu Ile Ala Ile Ser Lys Trp Gly
        420                 425                 430

CAT TTT TAT ATT AAT GGT TAC AAT TTC TTT AGC ACT TTT CCT ATT GAT        1403
His Phe Tyr Ile Asn Gly Tyr Asn Phe Phe Ser Thr Phe Pro Ile Asp
            435                 440                 445

TGT ATA TCT TTT AAT TTA ACC ACT GGT GAT AGT GGA GCA TTT TGG ACA        1451
Cys Ile Ser Phe Asn Leu Thr Thr Gly Asp Ser Gly Ala Phe Trp Thr
        450                 455                 460

ATT GCT TAC ACA TCG TAC ACT GAA GCA TTA GTA CAA GTT GAA AAC ACA        1499
Ile Ala Tyr Thr Ser Tyr Thr Glu Ala Leu Val Gln Val Glu Asn Thr
465                 470                 475                 480

GCT ATT AAA AAG GTG ACG TAT TGT AAC AGT CAC ATT AAT AAC ATC AAA        1547
Ala Ile Lys Lys Val Thr Tyr Cys Asn Ser His Ile Asn Asn Ile Lys
            485                 490                 495

TGT TCT CAA CTT ACT GCT AAC TTG CAA AAT GGA TTT TAT CCT GTT GCT        1595
Cys Ser Gln Leu Thr Ala Asn Leu Gln Asn Gly Phe Tyr Pro Val Ala
        500                 505                 510

TCA AGT GAA GTT GGT CTT GTC AAT AAG AGT GTT GTG TTA CTA CCT AGT        1643
Ser Ser Glu Val Gly Leu Val Asn Lys Ser Val Val Leu Leu Pro Ser
            515                 520                 525

TTC TAT TCA CAT ACC AGT GTT AAT ATA ACT ATT GAT CTT GGT ATG AAG        1691
Phe Tyr Ser His Thr Ser Val Asn Ile Thr Ile Asp Leu Gly Met Lys
        530                 535                 540

CGT AGT GGT TAT GGT CAA CCC ATA GCA TCA ACA CTA AGT AAC ATC ACA        1739
Arg Ser Gly Tyr Gly Gln Pro Ile Ala Ser Thr Leu Ser Asn Ile Thr
545                 550                 555                 560

CTA CCA ATG CAG GAT AAT AAC ACC GAT GTG TAC TGT ATT CGT TCC AAC        1787
Leu Pro Met Gln Asp Asn Asn Thr Asp Val Tyr Cys Ile Arg Ser Asn
            565                 570                 575

CAA TTT TCA GTC TAC GTG CAT TCC ACT TGC AAA AGC TCT TTA TGG GAC        1835
Gln Phe Ser Val Tyr Val His Ser Thr Cys Lys Ser Ser Leu Trp Asp
        580                 585                 590

AAT ATT TTT AAT TCA GAC TGT ACA GAT GTT TTA CAT GCC ACA GCT GTT        1883
Asn Ile Phe Asn Ser Asp Cys Thr Asp Val Leu His Ala Thr Ala Val
            595                 600                 605

ATA AAA ACT GGT ACT TGT CCT TTT TCA TTT GAT AAA TTG AAT AAT TAC        1931
Ile Lys Thr Gly Thr Cys Pro Phe Ser Phe Asp Lys Leu Asn Asn Tyr
        610                 615                 620

TTA ACT TTT AAC AAG TTC TGT TTG TCG TTG AAT CCT GTT GGT GCC AAC        1979
Leu Thr Phe Asn Lys Phe Cys Leu Ser Leu Asn Pro Val Gly Ala Asn
625                 630                 635                 640

TGT AAG TTT GAT GTT GCC GCC CGT ACA AGA ACC AAT GAG CAG GTT GTT        2027
Cys Lys Phe Asp Val Ala Ala Arg Thr Arg Thr Asn Glu Gln Val Val
            645                 650                 655

AGA AGT TTA TAT GTA ATG TAT GAA GAA GGA GAT AAC ATA GCG GGT GAC        2075
Arg Ser Leu Tyr Val Met Tyr Glu Glu Gly Asp Asn Ile Ala Gly Asp
        660                 665                 670

CGT CCT GAT AAT AGT GGT CTT CAC GAT TTG TCA GTG CTA CAC TTA GAT        2123
Arg Pro Asp Asn Ser Gly Leu His Asp Leu Ser Val Leu His Leu Asp
            675                 680                 685

TCC TGT ACA GAT TAC AAT ATA TAT GGT AGA ACT GGT GTT GGT ATT ATT        2171
Ser Cys Thr Asp Tyr Asn Ile Tyr Gly Arg Thr Gly Val Gly Ile Ile
        690                 695                 700

AGA CAA ACT AAC AGC ACA ATA TTT AGT GGC TTA TAT TAC ACA TCA CTA        2219
Arg Gln Thr Asn Ser Thr Ile Phe Ser Gly Leu Tyr Tyr Thr Ser Leu
705                 710                 715                 720
```

| | | | | | | | | | | | | | | | | |
|---|---|---|---|---|---|---|---|---|---|---|---|---|---|---|---|---|
| TCA | GGT | GAT | TTG | TTA | GGT | TTT | AAA | AAT | GTT | AGT | GAT | GGT | GTC | GTC | TAT | 2267 |
| Ser | Gly | Asp | Leu | Leu | Gly | Phe | Lys | Asn | Val | Ser | Asp | Gly | Val | Val | Tyr | |
| | | | 725 | | | | | 730 | | | | | 735 | | | |
| TCT | GTA | ACG | CCA | TGT | GAT | GTA | AGC | GCA | CAA | GCT | GCT | GTT | ATT | GAT | GGT | 2315 |
| Ser | Val | Thr | Pro | Cys | Asp | Val | Ser | Ala | Gln | Ala | Ala | Val | Ile | Asp | Gly | |
| | | | 740 | | | | | 745 | | | | | 750 | | | |
| GCC | ATA | GTT | GGA | GCT | ATG | ACT | TCC | ATT | AAT | AGC | GAA | CTG | TTA | GGT | CTA | 2363 |
| Ala | Ile | Val | Gly | Ala | Met | Thr | Ser | Ile | Asn | Ser | Glu | Leu | Leu | Gly | Leu | |
| | | 755 | | | | | 760 | | | | | 765 | | | | |
| ACT | CAT | TGG | ACA | ACA | ACA | CCT | AAT | TTT | TAT | TAT | TAC | TCC | ATA | TAT | AAT | 2411 |
| Thr | His | Trp | Thr | Thr | Thr | Pro | Asn | Phe | Tyr | Tyr | Tyr | Ser | Ile | Tyr | Asn | |
| | | 770 | | | | 775 | | | | | 780 | | | | | |
| TAT | ACA | AGT | GTG | AGA | ACT | CGT | GGC | ACT | GCA | ATT | GAT | AGT | AAC | GAT | GTT | 2459 |
| Tyr | Thr | Ser | Val | Arg | Thr | Arg | Gly | Thr | Ala | Ile | Asp | Ser | Asn | Asp | Val | |
| 785 | | | | | 790 | | | | | 795 | | | | | 800 | |
| GAT | TGT | GAA | CCT | ATC | ATA | ACC | TAT | TCT | AAT | ATA | GGT | GTT | TGT | AAA | AAT | 2507 |
| Asp | Cys | Glu | Pro | Ile | Ile | Thr | Tyr | Ser | Asn | Ile | Gly | Val | Cys | Lys | Asn | |
| | | | | 805 | | | | | 810 | | | | | 815 | | |
| GGA | GCT | TTG | GTT | TTT | ATT | AAC | GTC | ACA | CAT | TCT | GAT | GGA | GAC | GTT | CAA | 2555 |
| Gly | Ala | Leu | Val | Phe | Ile | Asn | Val | Thr | His | Ser | Asp | Gly | Asp | Val | Gln | |
| | | | 820 | | | | | 825 | | | | | 830 | | | |
| CCA | ATT | AGC | ACC | GGT | AAT | GTC | ACG | ATA | CCT | ACA | AAT | TTT | ACC | ATA | TCT | 2603 |
| Pro | Ile | Ser | Thr | Gly | Asn | Val | Thr | Ile | Pro | Thr | Asn | Phe | Thr | Ile | Ser | |
| | | 835 | | | | | 840 | | | | | 845 | | | | |
| GTG | CAA | GTT | GAA | TAC | ATT | CAG | GTT | TAC | ACT | ACA | CCA | GTG | TCA | ATA | GAC | 2651 |
| Val | Gln | Val | Glu | Tyr | Ile | Gln | Val | Tyr | Thr | Thr | Pro | Val | Ser | Ile | Asp | |
| | | 850 | | | | | 855 | | | | | 860 | | | | |
| TGT | GCA | AGA | TAC | GTT | TGC | AAT | GGT | AAC | CCT | AGA | TGC | AAT | AAA | TTG | TTA | 2699 |
| Cys | Ala | Arg | Tyr | Val | Cys | Asn | Gly | Asn | Pro | Arg | Cys | Asn | Lys | Leu | Leu | |
| 865 | | | | | 870 | | | | | 875 | | | | | 880 | |
| ACA | CAA | TAT | GTT | TCT | GCA | TGT | CAA | ACT | ATT | GAG | CAA | GCA | CTT | GCA | ATG | 2747 |
| Thr | Gln | Tyr | Val | Ser | Ala | Cys | Gln | Thr | Ile | Glu | Gln | Ala | Leu | Ala | Met | |
| | | | | 885 | | | | 890 | | | | | 895 | | | |
| GGT | GCC | AGA | CTT | GAA | AAC | ATG | GAG | ATT | GAT | TCC | ATG | TTG | TTT | GTT | TCG | 2795 |
| Gly | Ala | Arg | Leu | Glu | Asn | Met | Glu | Ile | Asp | Ser | Met | Leu | Phe | Val | Ser | |
| | | | 900 | | | | | 905 | | | | | 910 | | | |
| GAA | AAT | GCC | CTT | AAA | TTG | GCG | TCT | GTT | GAA | GCA | TTC | AAT | AGT | ACG | GAA | 2843 |
| Glu | Asn | Ala | Leu | Lys | Leu | Ala | Ser | Val | Glu | Ala | Phe | Asn | Ser | Thr | Glu | |
| | | 915 | | | | | 920 | | | | | 925 | | | | |
| ACT | CTA | GAT | CCT | ATT | TAC | AAA | GAA | TGG | CCC | AAT | ATT | GGT | GGT | TCT | TGG | 2891 |
| Thr | Leu | Asp | Pro | Ile | Tyr | Lys | Glu | Trp | Pro | Asn | Ile | Gly | Gly | Ser | Trp | |
| | | 930 | | | | | 935 | | | | | 940 | | | | |
| CTA | GGA | GGT | TTA | AAA | GAT | ATA | TTG | CCA | TCT | CAT | AAT | AGC | AAA | CGT | AAG | 2939 |
| Leu | Gly | Gly | Leu | Lys | Asp | Ile | Leu | Pro | Ser | His | Asn | Ser | Lys | Arg | Lys | |
| 945 | | | | | 950 | | | | | 955 | | | | | 960 | |
| TAC | CGT | TCA | GCT | ATA | GAA | GAC | TTG | CTT | TTT | GAT | AAG | GTT | GTA | ACA | TCT | 2987 |
| Tyr | Arg | Ser | Ala | Ile | Glu | Asp | Leu | Leu | Phe | Asp | Lys | Val | Val | Thr | Ser | |
| | | | | 965 | | | | | 970 | | | | | 975 | | |
| GGC | TTA | GGT | ACA | GTT | GAT | GAA | GAT | TAT | AAG | CGT | TGT | ACA | GGT | GGT | TAT | 3035 |
| Gly | Leu | Gly | Thr | Val | Asp | Glu | Asp | Tyr | Lys | Arg | Cys | Thr | Gly | Gly | Tyr | |
| | | | 980 | | | | | 985 | | | | | 990 | | | |
| GAT | ATA | GCT | GAC | TTA | GTG | TGT | GCA | CAA | TAT | TAT | AAT | GGC | ATC | ATG | GTG | 3083 |
| Asp | Ile | Ala | Asp | Leu | Val | Cys | Ala | Gln | Tyr | Tyr | Asn | Gly | Ile | Met | Val | |
| | | 995 | | | | | 1000 | | | | | 1005 | | | | |
| CTA | CCT | GGT | GTA | GCT | AAT | GAT | GAC | AAG | ATG | GCT | ATG | TAC | ACT | GCA | TCT | 3131 |
| Leu | Pro | Gly | Val | Ala | Asn | Asp | Asp | Lys | Met | Ala | Met | Tyr | Thr | Ala | Ser | |
| | 1010 | | | | | 1015 | | | | | 1020 | | | | | |
| CTT | GCA | GGT | GGT | ATA | ACA | TTA | GGT | GCA | CTA | GGT | GGT | GGC | GCC | GTG | GCT | 3179 |
| Leu | Ala | Gly | Gly | Ile | Thr | Leu | Gly | Ala | Leu | Gly | Gly | Gly | Ala | Val | Ala | |
| 1025 | | | | | 1030 | | | | | 1035 | | | | | 1040 | |

-continued

| | | | | | | | | | | | | | | | | |
|---|---|---|---|---|---|---|---|---|---|---|---|---|---|---|---|---|
| ATA | CCT | TTT | GCA | GTA | GCA | GTT | CAG | GCT | AGA | CTT | AAT | TAT | GTT | GCT | CTA | 3227 |
| Ile | Pro | Phe | Ala | Val | Ala | Val | Gln | Ala | Arg | Leu | Asn | Tyr | Val | Ala | Leu | |
| | | | | 1045 | | | | 1050 | | | | | 1055 | | | |
| CAA | ACT | GAT | GTA | TTG | AAC | AAA | AAC | CAA | CAG | ATC | CTG | GCT | AAT | GCT | TTC | 3275 |
| Gln | Thr | Asp | Val | Leu | Asn | Lys | Asn | Gln | Gln | Ile | Leu | Ala | Asn | Ala | Phe | |
| | | | | 1060 | | | | 1065 | | | | | 1070 | | | |
| AAC | CAA | GCT | ATT | GGT | AAC | ATT | ACA | CAG | GCA | TTT | GGT | AAG | GTT | AAT | GAC | 3323 |
| Asn | Gln | Ala | Ile | Gly | Asn | Ile | Thr | Gln | Ala | Phe | Gly | Lys | Val | Asn | Asp | |
| | | | | 1075 | | | | 1080 | | | | | 1085 | | | |
| GCA | ATA | CAT | CAA | ACA | TCA | CAA | GGT | CTT | GCC | ACT | GTT | GCT | AAA | GCA | TTG | 3371 |
| Ala | Ile | His | Gln | Thr | Ser | Gln | Gly | Leu | Ala | Thr | Val | Ala | Lys | Ala | Leu | |
| | | | | 1090 | | | | 1095 | | | | | 1100 | | | |
| GCA | AAA | GTG | CAA | GAT | GTT | GTT | AAC | ACA | CAA | GGT | CAA | GCT | TTA | AGC | CAC | 3419 |
| Ala | Lys | Val | Gln | Asp | Val | Val | Asn | Thr | Gln | Gly | Gln | Ala | Leu | Ser | His | |
| 1105 | | | | 1110 | | | | 1115 | | | | 1120 | | | | |
| CTA | ACA | GTA | CAA | TTG | CAA | AAC | AAT | TTT | CAA | GCC | ATT | AGT | AGT | TCC | ATT | 3467 |
| Leu | Thr | Val | Gln | Leu | Gln | Asn | Asn | Phe | Gln | Ala | Ile | Ser | Ser | Ser | Ile | |
| | | | | 1125 | | | | 1130 | | | | | 1135 | | | |
| AGT | GAC | ATT | TAC | AAC | AGG | CTT | GAT | GAA | TTG | AGT | GCT | GAT | GCA | CAA | GTT | 3515 |
| Ser | Asp | Ile | Tyr | Asn | Arg | Leu | Asp | Glu | Leu | Ser | Ala | Asp | Ala | Gln | Val | |
| | | | | 1140 | | | | 1145 | | | | | 1150 | | | |
| GAC | AGG | CTT | ATT | ACA | GGA | AGA | CTT | ACA | GCA | CTT | AAT | GCA | TTT | GTG | TCT | 3563 |
| Asp | Arg | Leu | Ile | Thr | Gly | Arg | Leu | Thr | Ala | Leu | Asn | Ala | Phe | Val | Ser | |
| | | | | 1155 | | | | 1160 | | | | | 1165 | | | |
| CAG | ACT | TTA | ACC | AGA | CAA | GCA | GAG | GTT | AGG | GCT | AGT | AGA | CAA | CTT | GCT | 3611 |
| Gln | Thr | Leu | Thr | Arg | Gln | Ala | Glu | Val | Arg | Ala | Ser | Arg | Gln | Leu | Ala | |
| | | | | 1170 | | | | 1175 | | | | | 1180 | | | |
| AAA | GAC | AAA | GTT | AAT | GAA | TGC | GTT | AGG | TCT | CAA | TCC | CAG | AGA | TTT | GGA | 3659 |
| Lys | Asp | Lys | Val | Asn | Glu | Cys | Val | Arg | Ser | Gln | Ser | Gln | Arg | Phe | Gly | |
| 1185 | | | | 1190 | | | | 1195 | | | | 1200 | | | | |
| TTC | TGT | GGT | AAT | GGT | ACA | CAT | TTG | TTT | TCA | CTT | GCA | AAT | GCA | GCA | CCA | 3707 |
| Phe | Cys | Gly | Asn | Gly | Thr | His | Leu | Phe | Ser | Leu | Ala | Asn | Ala | Ala | Pro | |
| | | | | 1205 | | | | 1210 | | | | | 1215 | | | |
| AAT | GGC | ATG | ATT | TTC | TTT | CAC | ACA | GTG | CTA | TTA | CCA | ACA | GCT | TAT | GAA | 3755 |
| Asn | Gly | Met | Ile | Phe | Phe | His | Thr | Val | Leu | Leu | Pro | Thr | Ala | Tyr | Glu | |
| | | | | 1220 | | | | 1225 | | | | | 1230 | | | |
| ACT | GTG | ACG | GCC | TGG | TCA | GGT | ATT | TGT | GCA | TCA | GAT | GGC | GAT | CGC | ACT | 3803 |
| Thr | Val | Thr | Ala | Trp | Ser | Gly | Ile | Cys | Ala | Ser | Asp | Gly | Asp | Arg | Thr | |
| | | | | 1235 | | | | 1240 | | | | | 1245 | | | |
| TTT | GGA | CTT | GTT | GTT | AAG | GAT | GTT | CAG | CTG | ACG | CTA | TTT | CGC | AAT | TTA | 3851 |
| Phe | Gly | Leu | Val | Val | Lys | Asp | Val | Gln | Leu | Thr | Leu | Phe | Arg | Asn | Leu | |
| | | | | 1250 | | | | 1255 | | | | | 1260 | | | |
| GAT | GAC | AAA | TTC | TAT | TTG | ACT | CCC | AGA | ACT | ATG | TAT | CAG | CCT | AGA | GTT | 3899 |
| Asp | Asp | Lys | Phe | Tyr | Leu | Thr | Pro | Arg | Thr | Met | Tyr | Gln | Pro | Arg | Val | |
| 1265 | | | | 1270 | | | | 1275 | | | | 1280 | | | | |
| GCA | ACT | AGT | TCT | GAT | TTT | GTT | CAA | ATA | GAA | GGT | TGT | GAT | GTG | TTG | TTT | 3947 |
| Ala | Thr | Ser | Ser | Asp | Phe | Val | Gln | Ile | Glu | Gly | Cys | Asp | Val | Leu | Phe | |
| | | | | 1285 | | | | 1290 | | | | | 1295 | | | |
| GTC | AAT | GCA | ACT | GTA | ATT | GAC | TTG | CCT | AGT | ATC | ATA | CCT | GAC | TAT | ATT | 3995 |
| Val | Asn | Ala | Thr | Val | Ile | Asp | Leu | Pro | Ser | Ile | Ile | Pro | Asp | Tyr | Ile | |
| | | | | 1300 | | | | 1305 | | | | | 1310 | | | |
| GAT | ATT | AAT | CAA | ACT | GTT | CAG | GAT | ATA | TTA | GAA | AAT | TTT | AGA | CCA | AAT | 4043 |
| Asp | Ile | Asn | Gln | Thr | Val | Gln | Asp | Ile | Leu | Glu | Asn | Phe | Arg | Pro | Asn | |
| | | | | 1315 | | | | 1320 | | | | | 1325 | | | |
| TGG | ACT | GTA | CCT | GAG | TTG | ACA | CTT | GAC | ATT | TTC | AAC | GCA | ACC | TAC | TTA | 4091 |
| Trp | Thr | Val | Pro | Glu | Leu | Thr | Leu | Asp | Ile | Phe | Asn | Ala | Thr | Tyr | Leu | |
| | | | | 1330 | | | | 1335 | | | | | 1340 | | | |
| AAC | CTG | ACT | GGT | GAA | ATT | AAT | GAC | TTA | GAA | TTT | AGG | TCG | GAA | AAG | TTA | 4139 |
| Asn | Leu | Thr | Gly | Glu | Ile | Asn | Asp | Leu | Glu | Phe | Arg | Ser | Glu | Lys | Leu | |
| 1345 | | | | 1350 | | | | 1355 | | | | 1360 | | | | |

```
CAT AAC ACC ACA GTA GAA CTT GCT GTT CTC ATT GAT AAT ATT AAT AAC        4187
His Asn Thr Thr Val Glu Leu Ala Val Leu Ile Asp Asn Ile Asn Asn
            1365            1370             1375

ACA TTA GTC AAT CTT GAA TGG CTC AAT AGA ATT GAA ACT TAT GTA AAA        4235
Thr Leu Val Asn Leu Glu Trp Leu Asn Arg Ile Glu Thr Tyr Val Lys
        1380            1385             1390

TGG CCT TGG TAT GTG TGG CTA CTA ATT GGA TTA GTA GTA ATA TTC TGC        4283
Trp Pro Trp Tyr Val Trp Leu Leu Ile Gly Leu Val Val Ile Phe Cys
        1395            1400             1405

ATA CCA TTA CTG CTA TTT TGC TGT TGT AGT ACA GGT TGC TGT GGA TGC        4331
Ile Pro Leu Leu Leu Phe Cys Cys Cys Ser Thr Gly Cys Cys Gly Cys
        1410            1415             1420

ATA GGT TGC TTA GGA AGT TGT TGT CAC TCT ATG TGT AGT AGA AGA CAA        4379
Ile Gly Cys Leu Gly Ser Cys Cys His Ser Met Cys Ser Arg Arg Gln
1425            1430            1435                    1440

TTT GAA AGT TAT GAA CCA ACC GAA AAA GTG CAC GTC CAC TAAATTCAAA        4428
Phe Glu Ser Tyr Glu Pro Thr Glu Lys Val His Val His
                1445            1450

ACTAATA                                                                 4435
```

( 2 ) INFORMATION FOR SEQ ID NO:6:

( i ) SEQUENCE CHARACTERISTICS:
        ( A ) LENGTH: 1453 amino acids
        ( B ) TYPE: amino acid
        ( C ) STRANDEDNESS: single
        ( D ) TOPOLOGY: linear ( i i ) MOLECULE TYPE: protein ( v i ) ORIGINAL SOURCE:
        ( A ) ORGANISM: Canine corona virus
        ( B ) STRAIN: CCV-C54

( i x ) FEATURE:
        ( A ) NAME/KEY: Protein
        ( B ) LOCATION: 1..1453
        ( D ) OTHER INFORMATION: /label=CCV-C54_spike ( x i ) SEQUENCE DESCRIPTION: SEQ ID NO:6:

```
Met Ile Val Leu Thr Leu Cys Leu Leu Leu Phe Ser Tyr Asn Ser Val
1               5                   10                  15

Ile Cys Thr Ser Asn Asn Asp Cys Val Gln Val Asn Val Thr Gln Leu
            20                  25                  30

Pro Gly Asn Glu Asn Ile Ile Lys Asp Phe Leu Phe Gln Asn Phe Lys
        35                  40                  45

Glu Glu Gly Ser Val Val Val Gly Gly Tyr Tyr Pro Thr Glu Val Trp
    50                  55                  60

Tyr Asn Cys Ser Arg Thr Ala Thr Thr Ala Tyr His Tyr Phe Ser
65              70                  75                  80

Asn Ile His Ala Phe Tyr Phe Asp Met Glu Ala Met Ala Asn Ser Thr
                85                  90                  95

Gly Asn Ala Arg Gly Lys Pro Leu Leu Val His Val His Gly Ser Pro
            100                 105                 110

Val Ser Ile Ile Val Tyr Ile Ser Ala Tyr Arg Asp Asp Val Gln Asn
        115                 120                 125

Arg Pro Leu Leu Lys His Gly Leu Leu Cys Ile Thr Lys Asn Ser Thr
    130                 135                 140

Ile Asp Tyr Asn Ser Phe Thr Ser Ala Gln Trp Arg Asp Ile Cys Leu
145                 150                 155                 160

Gly Thr Asp Arg Lys Ile Pro Phe Ser Val Val Pro Thr Asp Asn Gly
```

|     |     |     |     |     |     |     |     | 165 |     |     |     |     | 170 |     |     |     |     | 175 |     |
| --- | --- | --- | --- | --- | --- | --- | --- | --- | --- | --- | --- | --- | --- | --- | --- | --- | --- | --- | --- |

```
       Thr  Lys  Leu  Phe  Gly  Leu  Glu  Trp  Thr  Asp  Asp  Tyr  Val  Thr  Ala  Tyr
                      180                      185                     190
       Ile  Ser  Asp  Asp  Ser  His  Arg  Leu  Asn  Ile  Asn  Thr  Asn  Trp  Phe  Asn
                      195                      200                     205
       Asn  Val  Thr  Ile  Leu  Tyr  Ser  Arg  Ser  Ser  Thr  Ala  Thr  Trp  Gln  Lys
            210                      215                     220
       Ser  Ala  Ala  Tyr  Val  Tyr  Gln  Gly  Val  Ser  Asn  Phe  Thr  Tyr  Tyr  Lys
       225                      230                      235                     240
       Leu  Asn  Asn  Thr  Asn  Gly  Leu  Lys  Ser  Tyr  Glu  Leu  Cys  Glu  Asp  Tyr
                           245                      250                     255
       Glu  Tyr  Cys  Thr  Gly  Tyr  Ala  Thr  Asn  Val  Phe  Ala  Pro  Thr  Ser  Gly
                      260                      265                     270
       Gly  Tyr  Ile  Pro  Asp  Gly  Phe  Ser  Phe  Asn  Asn  Trp  Phe  Met  Leu  Thr
                      275                      280                     285
       Asn  Ser  Ser  Thr  Phe  Val  Ser  Gly  Arg  Phe  Val  Thr  Asn  Gln  Pro  Leu
            290                      295                     300
       Leu  Val  Asn  Cys  Leu  Val  Pro  Val  Pro  Ser  Phe  Gly  Val  Ala  Ala  Gln
       305                      310                      315                     320
       Glu  Phe  Cys  Phe  Glu  Gly  Ala  Gln  Phe  Ser  Gln  Cys  Asn  Gly  Val  Ser
                           325                      330                     335
       Leu  Asn  Asn  Thr  Val  Asp  Val  Ile  Arg  Phe  Asn  Leu  Asn  Phe  Thr  Thr
                      340                      345                     350
       Asn  Val  Gln  Ser  Gly  Met  Gly  Ala  Thr  Val  Phe  Ser  Leu  Asn  Thr  Thr
                      355                      360                     365
       Gly  Gly  Val  Ile  Leu  Glu  Ile  Ser  Cys  Tyr  Asn  Asp  Thr  Val  Ser  Glu
            370                      375                     380
       Ser  Ser  Phe  Tyr  Ser  Tyr  Gly  Glu  Ile  Pro  Phe  Gly  Val  Thr  Asp  Gly
       385                      390                      395                     400
       Pro  Arg  Tyr  Cys  Tyr  Val  Leu  Tyr  Asn  Gly  Thr  Ala  Leu  Lys  Tyr  Leu
                           405                      410                     415
       Gly  Thr  Leu  Pro  Pro  Ser  Val  Lys  Glu  Ile  Ala  Ile  Ser  Lys  Trp  Gly
                      420                      425                     430
       His  Phe  Tyr  Ile  Asn  Gly  Tyr  Asn  Phe  Phe  Ser  Thr  Phe  Pro  Ile  Asp
                 435                      440                     445
       Cys  Ile  Ser  Phe  Asn  Leu  Thr  Thr  Gly  Asp  Ser  Gly  Ala  Phe  Trp  Thr
            450                      455                     460
       Ile  Ala  Tyr  Thr  Ser  Tyr  Thr  Glu  Ala  Leu  Val  Gln  Val  Glu  Asn  Thr
       465                      470                      475                     480
       Ala  Ile  Lys  Lys  Val  Thr  Tyr  Cys  Asn  Ser  His  Ile  Asn  Asn  Ile  Lys
                      485                      490                     495
       Cys  Ser  Gln  Leu  Thr  Ala  Asn  Leu  Gln  Asn  Gly  Phe  Tyr  Pro  Val  Ala
                      500                      505                     510
       Ser  Ser  Glu  Val  Gly  Leu  Val  Asn  Lys  Ser  Val  Val  Leu  Leu  Pro  Ser
                 515                      520                     525
       Phe  Tyr  Ser  His  Thr  Ser  Val  Asn  Ile  Thr  Ile  Asp  Leu  Gly  Met  Lys
            530                      535                     540
       Arg  Ser  Gly  Tyr  Gly  Gln  Pro  Ile  Ala  Ser  Thr  Leu  Ser  Asn  Ile  Thr
       545                      550                      555                     560
       Leu  Pro  Met  Gln  Asp  Asn  Asn  Thr  Asp  Val  Tyr  Cys  Ile  Arg  Ser  Asn
                      565                      570                     575
       Gln  Phe  Ser  Val  Tyr  Val  His  Ser  Thr  Cys  Lys  Ser  Ser  Leu  Trp  Asp
                 580                      585                     590
```

-continued

| | | | | | | | | | | | | | | |
|---|---|---|---|---|---|---|---|---|---|---|---|---|---|---|
| Asn | Ile | Phe | Asn | Ser | Asp | Cys | Thr | Asp | Val | Leu | His | Ala | Thr | Ala | Val |
| | | 595 | | | | 600 | | | | 605 | | | | | |
| Ile | Lys | Thr | Gly | Thr | Cys | Pro | Phe | Ser | Phe | Asp | Lys | Leu | Asn | Asn | Tyr |
| 610 | | | | | 615 | | | | | 620 | | | | | |
| Leu | Thr | Phe | Asn | Lys | Phe | Cys | Leu | Ser | Leu | Asn | Pro | Val | Gly | Ala | Asn |
| 625 | | | | | 630 | | | | 635 | | | | | 640 | |
| Cys | Lys | Phe | Asp | Val | Ala | Ala | Arg | Thr | Arg | Thr | Asn | Glu | Gln | Val | Val |
| | | | | 645 | | | | | 650 | | | | | 655 | |
| Arg | Ser | Leu | Tyr | Val | Met | Tyr | Glu | Glu | Gly | Asp | Asn | Ile | Ala | Gly | Asp |
| | | | 660 | | | | | 665 | | | | 670 | | | |
| Arg | Pro | Asp | Asn | Ser | Gly | Leu | His | Asp | Leu | Ser | Val | Leu | His | Leu | Asp |
| | | 675 | | | | | 680 | | | | | 685 | | | |
| Ser | Cys | Thr | Asp | Tyr | Asn | Ile | Tyr | Gly | Arg | Thr | Gly | Val | Gly | Ile | Ile |
| | 690 | | | | | 695 | | | | | 700 | | | | |
| Arg | Gln | Thr | Asn | Ser | Thr | Ile | Phe | Ser | Gly | Leu | Tyr | Tyr | Thr | Ser | Leu |
| 705 | | | | | 710 | | | | | 715 | | | | | 720 |
| Ser | Gly | Asp | Leu | Leu | Gly | Phe | Lys | Asn | Val | Ser | Asp | Gly | Val | Val | Tyr |
| | | | | 725 | | | | | 730 | | | | | 735 | |
| Ser | Val | Thr | Pro | Cys | Asp | Val | Ser | Ala | Gln | Ala | Ala | Val | Ile | Asp | Gly |
| | | | 740 | | | | | 745 | | | | | 750 | | |
| Ala | Ile | Val | Gly | Ala | Met | Thr | Ser | Ile | Asn | Ser | Glu | Leu | Leu | Gly | Leu |
| | | 755 | | | | | 760 | | | | | 765 | | | |
| Thr | His | Trp | Thr | Thr | Thr | Pro | Asn | Phe | Tyr | Tyr | Tyr | Ser | Ile | Tyr | Asn |
| | 770 | | | | | 775 | | | | | 780 | | | | |
| Tyr | Thr | Ser | Val | Arg | Thr | Arg | Gly | Thr | Ala | Ile | Asp | Ser | Asn | Asp | Val |
| 785 | | | | | 790 | | | | | 795 | | | | | 800 |
| Asp | Cys | Glu | Pro | Ile | Ile | Thr | Tyr | Ser | Asn | Ile | Gly | Val | Cys | Lys | Asn |
| | | | | 805 | | | | | 810 | | | | | 815 | |
| Gly | Ala | Leu | Val | Phe | Ile | Asn | Val | Thr | His | Ser | Asp | Gly | Asp | Val | Gln |
| | | | | 820 | | | | | 825 | | | | | 830 | |
| Pro | Ile | Ser | Thr | Gly | Asn | Val | Thr | Ile | Pro | Thr | Asn | Phe | Thr | Ile | Ser |
| | | 835 | | | | | 840 | | | | | 845 | | | |
| Val | Gln | Val | Glu | Tyr | Ile | Gln | Val | Tyr | Thr | Thr | Pro | Val | Ser | Ile | Asp |
| | 850 | | | | | 855 | | | | | 860 | | | | |
| Cys | Ala | Arg | Tyr | Val | Cys | Asn | Gly | Asn | Pro | Arg | Cys | Asn | Lys | Leu | Leu |
| 865 | | | | | 870 | | | | | 875 | | | | | 880 |
| Thr | Gln | Tyr | Val | Ser | Ala | Cys | Gln | Thr | Ile | Glu | Gln | Ala | Leu | Ala | Met |
| | | | | 885 | | | | | 890 | | | | | 895 | |
| Gly | Ala | Arg | Leu | Glu | Asn | Met | Glu | Ile | Asp | Ser | Met | Leu | Phe | Val | Ser |
| | | | 900 | | | | | 905 | | | | | 910 | | |
| Glu | Asn | Ala | Leu | Lys | Leu | Ala | Ser | Val | Glu | Ala | Phe | Asn | Ser | Thr | Glu |
| | | | 915 | | | | | 920 | | | | | 925 | | |
| Thr | Leu | Asp | Pro | Ile | Tyr | Lys | Glu | Trp | Pro | Asn | Ile | Gly | Gly | Ser | Trp |
| | | 930 | | | | | 935 | | | | | 940 | | | |
| Leu | Gly | Gly | Leu | Lys | Asp | Ile | Leu | Pro | Ser | His | Asn | Ser | Lys | Arg | Lys |
| 945 | | | | | 950 | | | | | 955 | | | | | 960 |
| Tyr | Arg | Ser | Ala | Ile | Glu | Asp | Leu | Leu | Phe | Asp | Lys | Val | Val | Thr | Ser |
| | | | | 965 | | | | | 970 | | | | | 975 | |
| Gly | Leu | Gly | Thr | Val | Asp | Glu | Asp | Tyr | Lys | Arg | Cys | Thr | Gly | Gly | Tyr |
| | | | 980 | | | | | 985 | | | | | 990 | | |
| Asp | Ile | Ala | Asp | Leu | Val | Cys | Ala | Gln | Tyr | Tyr | Asn | Gly | Ile | Met | Val |
| | | 995 | | | | | 1000 | | | | | 1005 | | | |
| Leu | Pro | Gly | Val | Ala | Asn | Asp | Asp | Lys | Met | Ala | Met | Tyr | Thr | Ala | Ser |
| | | 1010 | | | | | 1015 | | | | | 1020 | | | |

```
Leu Ala Gly Gly Ile Thr Leu Gly Ala Leu Gly Gly Gly Ala Val Ala
1025                1030                1035                1040

Ile Pro Phe Ala Val Ala Val Gln Ala Arg Leu Asn Tyr Val Ala Leu
                1045                1050                1055

Gln Thr Asp Val Leu Asn Lys Asn Gln Gln Ile Leu Ala Asn Ala Phe
                1060                1065                1070

Asn Gln Ala Ile Gly Asn Ile Thr Gln Ala Phe Gly Lys Val Asn Asp
            1075                1080                1085

Ala Ile His Gln Thr Ser Gln Gly Leu Ala Thr Val Ala Lys Ala Leu
1090                1095                1100

Ala Lys Val Gln Asp Val Val Asn Thr Gln Gly Gln Ala Leu Ser His
1105                1110                1115                1120

Leu Thr Val Gln Leu Gln Asn Asn Phe Gln Ala Ile Ser Ser Ser Ile
            1125                1130                1135

Ser Asp Ile Tyr Asn Arg Leu Asp Glu Leu Ser Ala Asp Ala Gln Val
            1140                1145                1150

Asp Arg Leu Ile Thr Gly Arg Leu Thr Ala Leu Asn Ala Phe Val Ser
            1155                1160                1165

Gln Thr Leu Thr Arg Gln Ala Glu Val Arg Ala Ser Arg Gln Leu Ala
1170                1175                1180

Lys Asp Lys Val Asn Glu Cys Val Arg Ser Gln Ser Gln Arg Phe Gly
1185                1190                1195                1200

Phe Cys Gly Asn Gly Thr His Leu Phe Ser Leu Ala Asn Ala Ala Pro
                1205                1210                1215

Asn Gly Met Ile Phe Phe His Thr Val Leu Leu Pro Thr Ala Tyr Glu
            1220                1225                1230

Thr Val Thr Ala Trp Ser Gly Ile Cys Ala Ser Asp Gly Asp Arg Thr
            1235                1240                1245

Phe Gly Leu Val Val Lys Asp Val Gln Leu Thr Leu Phe Arg Asn Leu
1250                1255                1260

Asp Asp Lys Phe Tyr Leu Thr Pro Arg Thr Met Tyr Gln Pro Arg Val
1265                1270                1275                1280

Ala Thr Ser Ser Asp Phe Val Gln Ile Glu Gly Cys Asp Val Leu Phe
                1285                1290                1295

Val Asn Ala Thr Val Ile Asp Leu Pro Ser Ile Ile Pro Asp Tyr Ile
            1300                1305                1310

Asp Ile Asn Gln Thr Val Gln Asp Ile Leu Glu Asn Phe Arg Pro Asn
        1315                1320                1325

Trp Thr Val Pro Glu Leu Thr Leu Asp Ile Phe Asn Ala Thr Tyr Leu
        1330                1335                1340

Asn Leu Thr Gly Glu Ile Asn Asp Leu Glu Phe Arg Ser Glu Lys Leu
1345                1350                1355                1360

His Asn Thr Thr Val Glu Leu Ala Val Leu Ile Asp Asn Ile Asn Asn
                1365                1370                1375

Thr Leu Val Asn Leu Glu Trp Leu Asn Arg Ile Glu Thr Tyr Val Lys
                1380                1385                1390

Trp Pro Trp Tyr Val Trp Leu Leu Ile Gly Leu Val Val Ile Phe Cys
            1395                1400                1405

Ile Pro Leu Leu Leu Phe Cys Cys Cys Ser Thr Gly Cys Cys Gly Cys
        1410                1415                1420

Ile Gly Cys Leu Gly Ser Cys Cys His Ser Met Cys Ser Arg Arg Gln
1425                1430                1435                1440

Phe Glu Ser Tyr Glu Pro Thr Glu Lys Val His Val His
```

-continued (2) INFORMATION FOR SEQ ID NO:7:

(i) SEQUENCE CHARACTERISTICS:
       (A) LENGTH: 21 bases
       (B) TYPE: nucleic acid
       (C) STRANDEDNESS: single
       (D) TOPOLOGY: linear (ii) MOLECULE TYPE: DNA primer (xi) SEQUENCE DESCRIPTION: SEQ ID NO:7:

TTTCAAATT GTCTTCTACT T                                                    21

(2) INFORMATION FOR SEQ ID NO:8:

(i) SEQUENCE CHARACTERISTICS:
       (A) LENGTH: 14 bases
       (B) TYPE: nucleic acid
       (C) STRANDEDNESS: single
       (D) TOPOLOGY: linear (ii) MOLECULE TYPE: DNA primer (xi) SEQUENCE DESCRIPTION: SEQ ID NO:8:

CTAGGTAGTA ACAC                                                           14

(2) INFORMATION FOR SEQ ID NO:9:

(i) SEQUENCE CHARACTERISTICS:
       (A) LENGTH: 35 bases
       (B) TYPE: nucleic acid
       (C) STRANDEDNESS: single
       (D) TOPOLOGY: linear (ii) MOLECULE TYPE: cDNA (vi) ORIGINAL SOURCE:
       (A) ORGANISM: Canine corona virus
       (B) STRAIN: CCV-C54

(xi) SEQUENCE DESCRIPTION: SEQ ID NO:9:

CTAAACTTTG GTAATCACTT GGTTAATGTG CCATG                                    35